(12) United States Patent
Metzger et al.

(10) Patent No.: US 9,968,376 B2
(45) Date of Patent: May 15, 2018

(54) PATIENT-SPECIFIC ORTHOPEDIC INSTRUMENTS

(71) Applicant: Biomet Manufacturing, LLC, Warsaw, IN (US)

(72) Inventors: Robert Metzger, Wakarusa, IN (US); Joshua B. Catanzarite, Warsaw, IN (US); Brian M. May, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days. days.

(21) Appl. No.: 15/618,331

(22) Filed: Jun. 9, 2017

(65) Prior Publication Data

US 2017/0273718 A1    Sep. 28, 2017

Related U.S. Application Data

(60) Continuation of application No. 15/352,721, filed on Nov. 16, 2016, now Pat. No. 9,700,329, which is a
(Continued)

(51) Int. Cl.
*A61B 17/58*    (2006.01)
*A61B 17/60*    (2006.01)
(Continued)

(52) U.S. Cl.
CPC ............ *A61B 17/58* (2013.01); *A61B 17/155* (2013.01); *A61B 17/1764* (2013.01);
(Continued)

(58) Field of Classification Search
CPC combination set(s) only.
See application file for complete search history.

(56) References Cited

U.S. PATENT DOCUMENTS 1,480,285 A    1/1924    Moore
1,763,730 A    6/1930    Lackum
(Continued)

FOREIGN PATENT DOCUMENTS

CA    2447694 A1    12/2002
CA    2501041 A1    4/2004
(Continued)

OTHER PUBLICATIONS

U.S. Appl. No. 13/800,334, filed Mar. 13, 2013, Patient-Specific Knee Alignment Guide and Associated Method.
(Continued)

*Primary Examiner* — Sameh Boles
(74) *Attorney, Agent, or Firm* — Schwegman Lundberg & Woessner, P.A.

(57) ABSTRACT

A method of preparing a distal femur for a knee joint implant includes mounting a patient-specific bone engagement surface of a femoral alignment guide on a complementary surface of a distal femur of a patient. A plurality of alignment pins is inserted through a corresponding plurality of guiding bores of the femoral alignment guide into the distal femur. A cutting guide is mounted on first and second alignment pins of the plurality of alignment pins, and a first resection of the distal femur is made using the cutting guide while cutting through the femoral alignment guide.

19 Claims, 9 Drawing Sheets

Related U.S. Application Data continuation of application No. 14/086,447, filed on Nov. 21, 2013, now Pat. No. 9,522,010, which is a division of application No. 12/955,361, filed on Nov. 29, 2010, now Pat. No. 8,591,516.

(51) Int. Cl.

| | | |
|---|---|---|
| *A61F 2/00* | (2006.01) | |
| *A61B 17/15* | (2006.01) | |
| *A61B 17/17* | (2006.01) | |
| *A61B 34/10* | (2016.01) | |
| *A61F 2/30* | (2006.01) | |
| *A61F 2/46* | (2006.01) | |
| *A61F 2/38* | (2006.01) | |
| *A61B 17/56* | (2006.01) | |

(52) U.S. Cl.
CPC ........ *A61B 34/10* (2016.02); *A61B 2017/568* (2013.01); *A61F 2/389* (2013.01); *A61F 2002/30617* (2013.01); *A61F 2002/4662* (2013.01)

(56) References Cited

U.S. PATENT DOCUMENTS

| | | |
|---|---|---|
| 1,959,615 A | 5/1934 | Derrah |
| 2,181,746 A | 11/1939 | Siebrandt |
| 2,407,845 A | 9/1946 | Orisan |
| 2,416,228 A | 2/1947 | Sheppard |
| 2,433,815 A | 12/1947 | Nicephore |
| 2,455,655 A | 12/1948 | Carroll |
| 2,618,913 A | 11/1952 | Plancon et al. |
| 2,702,550 A | 2/1955 | Rowe |
| 2,724,326 A | 11/1955 | Long |
| 2,910,978 A | 11/1959 | Urist |
| 2,955,530 A | 10/1960 | Nilo |
| 3,048,522 A | 8/1962 | Velley |
| 3,229,006 A | 1/1966 | Egon |
| 3,229,372 A | 1/1966 | Quashnock et al. |
| 3,330,611 A | 7/1967 | Heifetz |
| 3,514,791 A | 6/1970 | Sparks |
| 3,554,197 A | 1/1971 | Arthur |
| 3,624,747 A | 11/1971 | Mcknight et al. |
| 3,631,596 A | 1/1972 | Glaus |
| 3,678,934 A | 7/1972 | Warfield et al. |
| 3,698,017 A | 10/1972 | Scales et al. |
| 3,703,036 A | 11/1972 | Karubian |
| 3,774,244 A | 11/1973 | Walker |
| 3,783,873 A | 1/1974 | Jacobs |
| 3,807,393 A | 4/1974 | McDonald |
| 3,811,449 A | 5/1974 | Gravlee et al. |
| 3,840,904 A | 10/1974 | Tronzo |
| 3,869,731 A | 3/1975 | Waugh et al. |
| 3,903,549 A | 9/1975 | Deyerle |
| 3,905,105 A | 9/1975 | Tuke |
| 3,905,374 A | 9/1975 | Winter |
| 3,911,923 A | 10/1975 | Yoon |
| 3,913,585 A | 10/1975 | Wolvek |
| 3,920,022 A | 11/1975 | Pastor |
| 3,941,127 A | 3/1976 | Froning |
| 3,967,625 A | 7/1976 | Yoon et al. |
| 3,975,858 A | 8/1976 | Much |
| 3,989,049 A | 11/1976 | Yoon |
| 3,991,426 A | 11/1976 | Flom et al. |
| 3,994,287 A | 11/1976 | Turp et al. |
| 4,053,953 A | 10/1977 | Flom et al. |
| 4,055,862 A | 11/1977 | Farling |
| 4,081,866 A | 4/1978 | Upshaw et al. |
| 4,085,466 A | 4/1978 | Goodfellow et al. |
| 4,085,743 A | 4/1978 | Yoon |
| 4,103,680 A | 8/1978 | Yoon |
| 4,246,895 A | 1/1981 | Rehder |
| 4,299,224 A | 11/1981 | Noiles |
| 4,304,178 A | 12/1981 | Haberle |
| 4,306,866 A | 12/1981 | Weissman |
| 4,311,145 A | 1/1982 | Esty et al. |
| 4,324,006 A | 4/1982 | Charnley |
| 4,344,193 A | 8/1982 | Kenny |
| 4,349,018 A | 9/1982 | Chamber |
| 4,373,709 A | 2/1983 | Whitt et al. |
| 4,374,523 A | 2/1983 | Yoon |
| 4,385,404 A | 5/1983 | Sully et al. |
| 4,386,609 A | 6/1983 | Mongeon |
| 4,400,833 A | 8/1983 | Kurland |
| 4,421,112 A | 12/1983 | Mains et al. |
| 4,428,571 A | 1/1984 | Sugarman |
| 4,436,684 A | 3/1984 | White |
| D273,895 S | 5/1984 | Kenna |
| D274,091 S | 5/1984 | Kenna |
| 4,453,421 A | 6/1984 | Umano |
| 4,457,306 A | 7/1984 | Borzone |
| 4,475,549 A | 10/1984 | Oh |
| 4,501,269 A | 2/1985 | Bagby |
| 4,506,393 A | 3/1985 | Murphy |
| 4,509,518 A | 4/1985 | Mcgarry et al. |
| 4,516,276 A | 5/1985 | Mittelmeier |
| 4,524,766 A | 6/1985 | Petersen |
| 4,528,980 A | 7/1985 | Kenna |
| 4,534,365 A | 8/1985 | Bonetta et al. |
| 4,535,773 A | 8/1985 | Yoon |
| 4,545,375 A | 10/1985 | Cline |
| 4,554,686 A | 11/1985 | Baker |
| 4,562,598 A | 1/1986 | Kranz |
| 4,565,191 A | 1/1986 | Slocum |
| 4,565,192 A | 1/1986 | Shapiro |
| 4,567,886 A | 2/1986 | Petersen |
| 4,574,794 A | 3/1986 | Cooke et al. |
| 4,619,391 A | 10/1986 | Sharkany et al. |
| 4,619,658 A | 10/1986 | Pappas et al. |
| 4,621,630 A | 11/1986 | Kenna |
| 4,624,254 A | 11/1986 | Mcgarry et al. |
| 4,632,111 A | 12/1986 | Roche |
| 4,633,862 A | 1/1987 | Petersen |
| 4,641,648 A | 2/1987 | Shapiro |
| 4,642,120 A | 2/1987 | Nevo et al. |
| 4,646,729 A | 3/1987 | Kenna et al. |
| 4,662,372 A | 5/1987 | Sharkany et al. |
| 4,663,720 A | 5/1987 | Duret et al. |
| 4,678,470 A | 7/1987 | Nashef et al. |
| 4,682,598 A | 7/1987 | Beraha |
| 4,685,460 A | 8/1987 | Thornton |
| 4,689,984 A | 9/1987 | Kellner |
| 4,695,283 A | 9/1987 | Aldinger |
| 4,696,292 A | 9/1987 | Heiple |
| 4,703,751 A | 11/1987 | Pohl |
| 4,704,686 A | 11/1987 | Aldinger |
| 4,706,660 A | 11/1987 | Petersen |
| 4,711,233 A | 12/1987 | Brown |
| 4,715,860 A | 12/1987 | Amstutz et al. |
| 4,718,413 A | 1/1988 | Johnson |
| 4,718,916 A | 1/1988 | Morscher |
| 4,719,907 A | 1/1988 | Banko et al. |
| 4,721,104 A | 1/1988 | Kaufman et al. |
| 4,722,330 A | 2/1988 | Russell et al. |
| 4,739,751 A | 4/1988 | Sapega et al. |
| 4,759,350 A | 7/1988 | Dunn et al. |
| 4,778,474 A | 10/1988 | Homsy |
| 4,794,854 A | 1/1989 | Swaim |
| 4,800,874 A | 1/1989 | David et al. |
| 4,817,602 A | 4/1989 | Beraha |
| 4,821,213 A | 4/1989 | Cline et al. |
| 4,822,365 A | 4/1989 | Walker et al. |
| 4,834,757 A | 5/1989 | Brantigan |
| 4,838,891 A | 6/1989 | Branemark et al. |
| 4,841,975 A | 6/1989 | Woolson |
| 4,846,161 A | 7/1989 | Roger |
| 4,863,472 A | 9/1989 | Tormala et al. |
| 4,871,975 A | 10/1989 | Nawata et al. |
| 4,888,022 A | 12/1989 | Huebsch |
| 4,892,545 A | 1/1990 | Day et al. |
| 4,893,619 A | 1/1990 | Dale et al. |
| 4,896,663 A | 1/1990 | Vandewalls |
| 4,907,577 A | 3/1990 | Wu |

(56) References Cited

U.S. PATENT DOCUMENTS

| | | |
|---|---|---|
| 4,911,721 A | 3/1990 | Andergaten |
| 4,927,422 A | 5/1990 | Engelhardt |
| 4,935,023 A | 6/1990 | Whiteside et al. |
| 4,936,852 A | 6/1990 | Kent et al. |
| 4,936,862 A | 6/1990 | Walker et al. |
| 4,950,296 A | 8/1990 | Mcintyre |
| 4,952,213 A | 8/1990 | Bowman et al. |
| 4,959,066 A | 9/1990 | Dunn et al. |
| 4,961,740 A | 10/1990 | Ray et al. |
| 4,961,954 A | 10/1990 | Goldberg et al. |
| 4,964,865 A | 10/1990 | Burkhead et al. |
| 4,976,737 A | 12/1990 | Leake |
| 4,979,949 A | 12/1990 | Matsen et al. |
| 4,979,957 A | 12/1990 | Hodorek |
| 4,985,037 A | 1/1991 | Petersen |
| 4,985,038 A | 1/1991 | Lyell |
| 4,994,064 A | 2/1991 | Aboczky |
| 5,002,579 A | 3/1991 | Copf et al. |
| 5,006,121 A | 4/1991 | Hafeli |
| 5,007,912 A | 4/1991 | Albrektsson et al. |
| 5,007,936 A | 4/1991 | Woolson |
| 5,015,247 A | 5/1991 | Michelson |
| 5,019,105 A | 5/1991 | Wiley |
| 5,030,219 A | 7/1991 | Matsen et al. |
| 5,030,221 A | 7/1991 | Buechel et al. |
| 5,032,132 A | 7/1991 | Matsen, III et al. |
| 5,035,700 A | 7/1991 | Kenna |
| 5,037,424 A | 8/1991 | Aboczsky |
| 5,041,117 A | 8/1991 | Engelhardt |
| 5,053,037 A | 10/1991 | Lackey et al. |
| 5,053,039 A | 10/1991 | Hofmann et al. |
| 5,056,351 A | 10/1991 | Stiver et al. |
| 5,060,678 A | 10/1991 | Bauman et al. |
| 5,061,270 A | 10/1991 | Aboczky |
| 5,061,286 A | 10/1991 | Lyle |
| 5,062,843 A | 11/1991 | Mahony, III |
| 5,073,373 A | 12/1991 | O'Leary et al. |
| 5,082,670 A | 1/1992 | Gage et al. |
| 5,084,050 A | 1/1992 | Draenert |
| 5,086,401 A | 2/1992 | Glassman et al. |
| 5,092,869 A | 3/1992 | Waldron |
| 5,098,383 A | 3/1992 | Hemmy et al. |
| 5,098,436 A | 3/1992 | Ferrante et al. |
| 5,098,437 A | 3/1992 | Kashuba et al. |
| 5,099,859 A | 3/1992 | Bell |
| 5,100,689 A | 3/1992 | Goldberg et al. |
| 5,101,720 A | 4/1992 | Bianchi |
| 5,108,425 A | 4/1992 | Hwang |
| 5,108,441 A | 4/1992 | Mcdowell |
| 5,111,987 A | 5/1992 | Moeinzadeh et al. |
| 5,122,144 A | 6/1992 | Bert et al. |
| 5,123,906 A | 6/1992 | Kelman |
| 5,123,927 A | 6/1992 | Duncan et al. |
| 5,129,908 A | 7/1992 | Petersen |
| 5,129,909 A | 7/1992 | Sutherland |
| 5,133,760 A | 7/1992 | Petersen et al. |
| 5,140,777 A | 8/1992 | Ushiyama et al. |
| 5,141,512 A | 8/1992 | Farmer et al. |
| 5,147,365 A | 9/1992 | Whitlock et al. |
| 5,150,304 A | 9/1992 | Berchem et al. |
| 5,152,744 A | 10/1992 | Krause et al. |
| 5,152,778 A | 10/1992 | Bales, Jr. et al. |
| 5,154,717 A | 10/1992 | Matsen, III et al. |
| 5,162,506 A | 11/1992 | Hadden |
| 5,163,949 A | 11/1992 | Bonutti |
| 5,170,800 A | 12/1992 | Smith et al. |
| 5,171,243 A | 12/1992 | Kashuba et al. |
| 5,171,244 A | 12/1992 | Caspari et al. |
| 5,171,276 A | 12/1992 | Caspari et al. |
| 5,174,300 A | 12/1992 | Bales et al. |
| 5,176,684 A | 1/1993 | Ferrante et al. |
| 5,176,702 A | 1/1993 | Bales et al. |
| 5,176,711 A | 1/1993 | Grimes |
| 5,178,622 A | 1/1993 | Lehner, II |
| 5,183,053 A | 2/1993 | Yeh |
| 5,183,464 A | 2/1993 | Dubrul et al. |
| 5,186,178 A | 2/1993 | Yeh |
| 5,192,327 A | 3/1993 | Brantigan |
| 5,194,066 A | 3/1993 | Van Zile |
| 5,197,968 A | 3/1993 | Clement |
| 5,197,971 A | 3/1993 | Bonutti |
| 5,197,987 A | 3/1993 | Koch et al. |
| 5,204,106 A | 4/1993 | Schepers et al. |
| 5,207,680 A | 5/1993 | Dietz et al. |
| 5,207,692 A | 5/1993 | Kraus et al. |
| 5,217,463 A | 6/1993 | Mikhail |
| 5,222,984 A | 6/1993 | Forte |
| 5,228,459 A | 7/1993 | Caspari et al. |
| 5,234,433 A | 8/1993 | Bert et al. |
| 5,242,448 A | 9/1993 | Pettine et al. |
| 5,246,444 A | 9/1993 | Schreiber |
| 5,253,506 A | 10/1993 | Davis et al. |
| 5,258,004 A | 11/1993 | Bales et al. |
| 5,258,032 A | 11/1993 | Bertin |
| 5,261,915 A | 11/1993 | Durlacher et al. |
| 5,263,498 A | 11/1993 | Caspari et al. |
| 5,263,987 A | 11/1993 | Shah |
| 5,269,785 A | 12/1993 | Bonutti |
| 5,273,524 A | 12/1993 | Fox et al. |
| 5,274,565 A | 12/1993 | Reuben |
| D343,247 S | 1/1994 | Walen |
| 5,275,166 A | 1/1994 | Vaitekunas et al. |
| 5,275,603 A | 1/1994 | Ferrante et al. |
| 5,282,802 A | 2/1994 | Mahony, III |
| 5,282,803 A | 2/1994 | Lackey |
| 5,285,773 A | 2/1994 | Bonutti et al. |
| 5,293,878 A | 3/1994 | Bales et al. |
| 5,295,994 A | 3/1994 | Bonutti |
| 5,299,288 A | 3/1994 | Glassman et al. |
| 5,300,077 A | 4/1994 | Howell |
| 5,304,181 A | 4/1994 | Caspari et al. |
| 5,306,285 A | 4/1994 | Miller et al. |
| 5,308,349 A | 5/1994 | Mikhail |
| 5,314,482 A | 5/1994 | Goodfellow et al. |
| 5,320,529 A | 6/1994 | Pompa |
| 5,320,625 A | 6/1994 | Bertin |
| 5,322,505 A | 6/1994 | Krause et al. |
| 5,323,697 A | 6/1994 | Schrock |
| 5,329,845 A | 7/1994 | Bichel |
| 5,342,366 A | 8/1994 | Whiteside et al. |
| 5,342,367 A | 8/1994 | Ferrante et al. |
| 5,342,368 A | 8/1994 | Petersen |
| 5,344,423 A | 9/1994 | Dietz et al. |
| 5,344,458 A | 9/1994 | Bonutti |
| 5,348,541 A | 9/1994 | Bonutti |
| 5,360,446 A | 11/1994 | Kennedy |
| 5,364,402 A | 11/1994 | Mumme et al. |
| 5,368,599 A | 11/1994 | Hirsch et al. |
| 5,368,858 A | 11/1994 | Hunziker |
| 5,370,692 A | 12/1994 | Fink et al. |
| 5,370,699 A | 12/1994 | Hood et al. |
| 5,379,133 A | 1/1995 | Kirk |
| 5,382,249 A | 1/1995 | Fletcher et al. |
| 5,383,937 A | 1/1995 | Mikhail |
| 5,390,683 A | 2/1995 | Pisharodi |
| 5,395,376 A | 2/1995 | Pisharodi |
| 5,405,395 A | 4/1995 | Coates |
| 5,408,409 A | 4/1995 | Glassman et al. |
| D358,647 S | 5/1995 | Cohen et al. |
| 5,411,521 A | 5/1995 | Putnam et al. |
| 5,415,662 A | 5/1995 | Ferrante et al. |
| 5,417,694 A | 5/1995 | Marik et al. |
| 5,423,827 A | 6/1995 | Mumme et al. |
| 5,425,355 A | 6/1995 | Kulick |
| 5,425,745 A | 6/1995 | Green et al. |
| 5,438,263 A | 8/1995 | Dworkin et al. |
| 5,440,496 A | 8/1995 | Andersson et al. |
| 5,443,475 A | 8/1995 | Auerbach et al. |
| 5,445,639 A | 8/1995 | Kuslich et al. |
| 5,445,642 A | 8/1995 | McNulty et al. |
| 5,448,489 A | 9/1995 | Reuben |
| 5,449,360 A | 9/1995 | Schreiber |
| 5,452,407 A | 9/1995 | Crook |
| 5,454,365 A | 10/1995 | Bonutti |

(56) References Cited

U.S. PATENT DOCUMENTS

| | | |
|---|---|---|
| 5,454,815 A | 10/1995 | Geisser et al. |
| 5,454,816 A | 10/1995 | Ashby |
| 5,456,268 A | 10/1995 | Bonutti |
| 5,462,550 A | 10/1995 | Dietz et al. |
| 5,472,415 A | 12/1995 | King et al. |
| 5,474,559 A | 12/1995 | Bertin et al. |
| 5,484,095 A | 1/1996 | Green et al. |
| 5,486,178 A | 1/1996 | Hodge |
| 5,490,854 A | 2/1996 | Fisher et al. |
| 5,496,324 A | 3/1996 | Barnes |
| 5,497,933 A | 3/1996 | Defonzo et al. |
| 5,507,763 A | 4/1996 | Petersen et al. |
| 5,507,833 A | 4/1996 | Bohn |
| 5,514,139 A | 5/1996 | Goldstein et al. |
| 5,514,143 A | 5/1996 | Bonutti et al. |
| 5,514,519 A | 5/1996 | Neckers |
| 5,520,692 A | 5/1996 | Ferrante |
| 5,520,694 A | 5/1996 | Dance et al. |
| 5,520,695 A | 5/1996 | Luckman |
| 5,522,897 A | 6/1996 | King et al. |
| 5,527,317 A | 6/1996 | Ashby et al. |
| 5,539,649 A | 7/1996 | Walsh et al. |
| 5,540,695 A | 7/1996 | Levy |
| 5,545,222 A | 8/1996 | Bonutti |
| 5,546,720 A | 8/1996 | Labruzza |
| 5,549,683 A | 8/1996 | Bonutti |
| 5,549,688 A | 8/1996 | Ries et al. |
| 5,554,169 A | 9/1996 | Green et al. |
| 5,554,190 A | 9/1996 | Draenert |
| 5,560,096 A | 10/1996 | Stephens |
| 5,560,728 A | 10/1996 | Mcfadden |
| 5,562,675 A | 10/1996 | Mcnulty et al. |
| 5,569,163 A | 10/1996 | Francis et al. |
| 5,569,261 A | 10/1996 | Marik et al. |
| 5,570,700 A | 11/1996 | Vogeler |
| 5,571,110 A | 11/1996 | Matsen, III et al. |
| 5,571,111 A | 11/1996 | Aboczky |
| 5,578,037 A | 11/1996 | Sanders et al. |
| 5,578,039 A | 11/1996 | Vendrely et al. |
| 5,586,558 A | 12/1996 | Riley |
| 5,593,411 A | 1/1997 | Stalcup et al. |
| 5,593,448 A | 1/1997 | Dong |
| 5,595,703 A | 1/1997 | Swaelens et al. |
| 5,597,379 A | 1/1997 | Haines et al. |
| 5,601,565 A | 2/1997 | Huebner |
| 5,607,431 A | 3/1997 | Dudasik et al. |
| 5,608,052 A | 3/1997 | Zmitek et al. |
| 5,609,603 A | 3/1997 | Linden |
| 5,611,802 A | 3/1997 | Samuelson et al. |
| 5,613,969 A | 3/1997 | Jenkins, Jr. |
| 5,616,147 A | 4/1997 | Gadelius |
| 5,620,448 A | 4/1997 | Puddu |
| 5,624,444 A | 4/1997 | Wixon et al. |
| 5,624,463 A | 4/1997 | Stone et al. |
| 5,632,745 A | 5/1997 | Schwartz |
| 5,634,927 A | 6/1997 | Houston et al. |
| 5,641,323 A | 6/1997 | Caldarise |
| 5,643,272 A | 7/1997 | Haines et al. |
| 5,649,946 A | 7/1997 | Bramlet |
| 5,649,947 A | 7/1997 | Auerbach et al. |
| 5,653,714 A | 8/1997 | Dietz et al. |
| 5,658,294 A | 8/1997 | Sederholm |
| 5,659,947 A | 8/1997 | Eilers et al. |
| 5,662,656 A | 9/1997 | White |
| 5,662,710 A | 9/1997 | Bonutti |
| 5,667,069 A | 9/1997 | Williams, Jr. |
| 5,667,511 A | 9/1997 | Vendrely et al. |
| 5,667,512 A | 9/1997 | Johnson |
| 5,667,520 A | 9/1997 | Bonutti |
| 5,671,018 A | 9/1997 | Ohara et al. |
| D385,163 S | 10/1997 | Hutchins et al. |
| 5,676,668 A | 10/1997 | McCue et al. |
| 5,677,107 A | 10/1997 | Neckers |
| 5,681,316 A | 10/1997 | DeOrio et al. |
| 5,681,354 A | 10/1997 | Eckhoff |
| 5,682,886 A | 11/1997 | Delp et al. |
| 5,683,398 A | 11/1997 | Carls et al. |
| 5,683,469 A | 11/1997 | Johnson et al. |
| 5,688,279 A | 11/1997 | McNulty et al. |
| 5,688,280 A | 11/1997 | Booth, Jr. et al. |
| 5,690,635 A | 11/1997 | Matsen, III et al. |
| 5,694,693 A | 12/1997 | Hutchins et al. |
| 5,697,933 A | 12/1997 | Gundlapalli et al. |
| 5,702,447 A | 12/1997 | Walch et al. |
| 5,702,460 A | 12/1997 | Carls et al. |
| 5,702,464 A | 12/1997 | Lackey et al. |
| 5,702,475 A | 12/1997 | Zahedi |
| 5,704,941 A | 1/1998 | Jacober et al. |
| 5,707,350 A | 1/1998 | Krause et al. |
| 5,709,689 A | 1/1998 | Ferrante et al. |
| 5,712,543 A | 1/1998 | Sjostrom |
| 5,716,360 A | 2/1998 | Baldwin et al. |
| 5,718,708 A | 2/1998 | Webb |
| 5,720,752 A | 2/1998 | Elliot et al. |
| 5,722,978 A | 3/1998 | Jenkins, Jr. |
| 5,723,331 A | 3/1998 | Tubo et al. |
| 5,725,376 A | 3/1998 | Poirier |
| 5,725,592 A | 3/1998 | White et al. |
| 5,725,593 A | 3/1998 | Caracciolo |
| 5,728,128 A | 3/1998 | Crickenberger et al. |
| 5,733,292 A | 3/1998 | Gustilo et al. |
| 5,735,277 A | 4/1998 | Schuster |
| 5,745,834 A | 4/1998 | Bampton et al. |
| 5,748,767 A | 5/1998 | Raab |
| 5,749,875 A | 5/1998 | Puddu |
| 5,749,876 A | 5/1998 | Duvillier et al. |
| 5,755,731 A | 5/1998 | Grinberg |
| 5,755,791 A | 5/1998 | Whitson et al. |
| 5,755,803 A | 5/1998 | Haines et al. |
| 5,762,125 A | 6/1998 | Mastrorio |
| 5,766,251 A | 6/1998 | Koshino |
| 5,768,134 A | 6/1998 | Swaelens et al. |
| 5,769,092 A | 6/1998 | Williamson, Jr. |
| 5,769,855 A | 6/1998 | Bertin et al. |
| 5,769,899 A | 6/1998 | Schwartz et al. |
| 5,772,594 A | 6/1998 | Barrick |
| 5,776,200 A | 7/1998 | Johnson et al. |
| 5,786,217 A | 7/1998 | Tubo et al. |
| 5,788,700 A | 8/1998 | Morawa et al. |
| 5,792,143 A | 8/1998 | Samuelson et al. |
| 5,798,924 A | 8/1998 | Eufinger et al. |
| 5,799,055 A | 8/1998 | Peshkin et al. |
| 5,810,827 A | 9/1998 | Haines et al. |
| 5,810,831 A | 9/1998 | D'Antonio |
| 5,817,097 A | 10/1998 | Howard et al. |
| 5,817,109 A | 10/1998 | Mcgarry et al. |
| 5,824,083 A | 10/1998 | Draenert |
| 5,835,619 A | 11/1998 | Morimoto et al. |
| 5,842,477 A | 12/1998 | Naughton et al. |
| 5,846,931 A | 12/1998 | Hattersley et al. |
| 5,860,980 A | 1/1999 | Axelson, Jr. et al. |
| 5,860,981 A | 1/1999 | Bertin et al. |
| 5,866,415 A | 2/1999 | Villeneuve |
| 5,871,018 A | 2/1999 | Delp et al. |
| 5,871,493 A | 2/1999 | Sjostrom et al. |
| 5,876,456 A | 3/1999 | Sederholm et al. |
| 5,879,354 A | 3/1999 | Haines et al. |
| 5,879,398 A | 3/1999 | Swarts et al. |
| 5,879,402 A | 3/1999 | Lawes et al. |
| 5,879,404 A | 3/1999 | Bateman et al. |
| 5,880,976 A | 3/1999 | DiGioia, III et al. |
| 5,885,297 A | 3/1999 | Matsen |
| 5,885,298 A | 3/1999 | Herrington et al. |
| 5,888,219 A | 3/1999 | Bonutti |
| 5,895,389 A | 4/1999 | Schenk et al. |
| 5,899,907 A | 5/1999 | Johnson |
| 5,899,914 A | 5/1999 | Zirps et al. |
| 5,901,060 A | 5/1999 | Schall et al. |
| 5,902,340 A | 5/1999 | White et al. |
| 5,908,424 A | 6/1999 | Bertin et al. |
| 5,911,723 A | 6/1999 | Ashby et al. |
| 5,911,724 A | 6/1999 | Wehrli |
| 5,913,874 A | 6/1999 | Berns et al. |
| 5,916,219 A | 6/1999 | Matsuno et al. |

(56) References Cited

U.S. PATENT DOCUMENTS

| | | |
|---|---|---|
| 5,921,988 A | 7/1999 | Legrand |
| 5,921,990 A | 7/1999 | Webb |
| 5,925,049 A | 7/1999 | Gustilo et al. |
| 5,925,077 A | 7/1999 | Williamson et al. |
| 5,942,370 A | 8/1999 | Neckers |
| 5,961,499 A | 10/1999 | Bonutti et al. |
| 5,967,777 A | 10/1999 | Klein et al. |
| 5,976,149 A | 11/1999 | Masini |
| 5,980,526 A | 11/1999 | Johnson et al. |
| 5,995,738 A | 11/1999 | DiGioia, III et al. |
| 5,997,566 A | 12/1999 | Tobin |
| 6,002,859 A | 12/1999 | DiGioia, III et al. |
| 6,007,537 A | 12/1999 | Burkinshaw et al. |
| 6,008,433 A | 12/1999 | Stone |
| 6,012,456 A | 1/2000 | Schuerch |
| 6,013,081 A | 1/2000 | Burkinshaw et al. |
| 6,015,419 A | 1/2000 | Strome et al. |
| 6,019,767 A | 2/2000 | Howell |
| 6,022,350 A | 2/2000 | Ganem |
| 6,024,746 A | 2/2000 | Katz |
| 6,033,415 A | 3/2000 | Mittelstadt et al. |
| 6,042,612 A | 3/2000 | Voydeville |
| 6,056,754 A | 5/2000 | Haines et al. |
| 6,056,756 A | 5/2000 | Eng et al. |
| 6,059,789 A | 5/2000 | Dinger |
| 6,059,817 A | 5/2000 | Bonutti et al. |
| 6,059,831 A | 5/2000 | Braslow et al. |
| 6,059,833 A | 5/2000 | Doets |
| 6,063,095 A | 5/2000 | Wang et al. |
| 6,066,175 A | 5/2000 | Henderson et al. |
| 6,077,270 A | 6/2000 | Katz |
| 6,077,287 A | 6/2000 | Taylor et al. |
| 6,086,593 A | 7/2000 | Bonutti |
| 6,090,122 A | 7/2000 | Sjostrom et al. |
| 6,096,043 A | 8/2000 | Techiera et al. |
| 6,099,531 A | 8/2000 | Bonutti |
| 6,099,532 A | 8/2000 | Florea |
| 6,102,850 A | 8/2000 | Wang et al. |
| 6,106,529 A | 8/2000 | Techiera |
| 6,118,845 A | 9/2000 | Simon et al. |
| 6,120,509 A | 9/2000 | Wheeler |
| 6,120,510 A | 9/2000 | Albrektsson et al. |
| 6,120,544 A | 9/2000 | Grundei et al. |
| 6,126,690 A | 10/2000 | Ateshian et al. |
| 6,126,692 A | 10/2000 | Robie et al. |
| 6,132,469 A | 10/2000 | Schroeder |
| 6,132,472 A | 10/2000 | Bonutti |
| 6,136,033 A | 10/2000 | Suemer |
| 6,156,069 A | 12/2000 | Amstutz |
| 6,156,070 A | 12/2000 | Incavo et al. |
| 6,159,217 A | 12/2000 | Robie et al. |
| 6,159,246 A | 12/2000 | Mendes et al. |
| 6,161,080 A | 12/2000 | Aouni-Ateshian et al. |
| 6,162,257 A | 12/2000 | Gustilo et al. |
| 6,165,223 A | 12/2000 | Metzger et al. |
| 6,171,340 B1 | 1/2001 | Mcdowell et al. |
| 6,174,321 B1 | 1/2001 | Webb |
| 6,185,315 B1 | 2/2001 | Schmucker et al. |
| 6,187,010 B1 | 2/2001 | Masini |
| 6,187,023 B1 | 2/2001 | Bonutti |
| 6,195,158 B1 | 2/2001 | Cadell et al. |
| 6,195,615 B1 | 2/2001 | Lysen |
| 6,197,064 B1 | 3/2001 | Haines et al. |
| 6,198,794 B1 | 3/2001 | Peshkin et al. |
| 6,203,546 B1 | 3/2001 | Macmahon |
| 6,205,411 B1 | 3/2001 | DiGioia, III et al. |
| 6,206,927 B1 | 3/2001 | Fell et al. |
| 6,210,445 B1 | 4/2001 | Zawadzki |
| 6,211,976 B1 | 4/2001 | Popovich et al. |
| 6,214,051 B1 | 4/2001 | Badorf et al. |
| 6,228,121 B1 | 5/2001 | Khalili |
| 6,238,435 B1 | 5/2001 | Meulink et al. |
| 6,254,604 B1 | 7/2001 | Howell |
| 6,258,097 B1 | 7/2001 | Cook et al. |
| 6,258,127 B1 | 7/2001 | Schmotzer |
| 6,264,698 B1 | 7/2001 | Lawes et al. |
| 6,270,529 B1 | 8/2001 | Terrill-Grisoni et al. |
| 6,273,891 B1 | 8/2001 | Masini |
| 6,277,136 B1 | 8/2001 | Bonutti et al. |
| 6,290,703 B1 | 9/2001 | Ganem |
| 6,290,704 B1 | 9/2001 | Burkinshaw et al. |
| 6,290,727 B1 | 9/2001 | Otto et al. |
| 6,293,971 B1 | 9/2001 | Nelson et al. |
| 6,301,495 B1 | 10/2001 | Gueziec et al. |
| 6,302,913 B1 | 10/2001 | Ripamonti et al. |
| 6,310,269 B1 | 10/2001 | Friese et al. |
| 6,312,258 B1 | 11/2001 | Ashman |
| 6,312,473 B1 | 11/2001 | Oshida |
| 6,319,285 B1 | 11/2001 | Chamier et al. |
| 6,322,728 B1 | 11/2001 | Brodkin et al. |
| 6,325,806 B1 | 12/2001 | Fox |
| 6,325,829 B1 | 12/2001 | Schmotzer |
| 6,327,491 B1 | 12/2001 | Franklin et al. |
| 6,328,572 B1 | 12/2001 | Higashida et al. |
| 6,338,737 B1 | 1/2002 | Toledano |
| 6,338,738 B1 | 1/2002 | Bellotti et al. |
| 6,343,987 B2 | 2/2002 | Hayama et al. |
| 6,354,011 B1 | 3/2002 | Albrecht |
| 6,358,266 B1 | 3/2002 | Bonutti |
| 6,361,506 B1 | 3/2002 | Saenger et al. |
| 6,361,563 B2 | 3/2002 | Terrill-Grisoni et al. |
| 6,361,565 B1 | 3/2002 | Bonutti |
| 6,379,299 B1 | 4/2002 | Borodulin et al. |
| 6,379,388 B1 | 4/2002 | Ensign et al. |
| 6,383,228 B1 | 5/2002 | Schmotzer |
| 6,391,040 B1 | 5/2002 | Christoudias |
| 6,391,251 B1 | 5/2002 | Keicher et al. |
| 6,395,005 B1 | 5/2002 | Lovell |
| 6,406,495 B1 | 6/2002 | Schoch |
| 6,409,722 B1 | 6/2002 | Hoey et al. |
| 6,413,279 B1 | 7/2002 | Metzger et al. |
| 6,416,553 B1 | 7/2002 | White et al. |
| 6,423,063 B1 | 7/2002 | Bonutti |
| 6,424,332 B1 | 7/2002 | Powell |
| 6,427,698 B1 | 8/2002 | Yoon et al. |
| 6,428,541 B1 | 8/2002 | Boyd et al. |
| 6,431,743 B1 | 8/2002 | Mizutani et al. |
| D462,767 S | 9/2002 | Meyer et al. |
| 6,447,448 B1 | 9/2002 | Ishikawa et al. |
| 6,458,135 B1 | 10/2002 | Harwin et al. |
| 6,459,948 B1 | 10/2002 | Ateshian et al. |
| 6,463,351 B1 | 10/2002 | Clynch |
| 6,468,280 B1 | 10/2002 | Saenger et al. |
| 6,468,289 B1 | 10/2002 | Bonutti |
| 6,475,243 B1 | 11/2002 | Sheldon et al. |
| 6,478,799 B1 | 11/2002 | Williamson |
| 6,482,209 B1 | 11/2002 | Engh et al. |
| 6,482,236 B2 | 11/2002 | Habecker |
| 6,488,715 B1 | 12/2002 | Pope et al. |
| 6,500,181 B1 | 12/2002 | Portney |
| 6,503,255 B1 | 1/2003 | Albrektsson et al. |
| 6,503,267 B2 | 1/2003 | Bonutti et al. |
| 6,508,980 B1 | 1/2003 | Sachs et al. |
| 6,510,334 B1 | 1/2003 | Schuster et al. |
| 6,514,259 B2 | 2/2003 | Picard et al. |
| 6,517,583 B1 | 2/2003 | Pope et al. |
| 6,519,998 B2 | 2/2003 | Ertl et al. |
| 6,520,964 B2 | 2/2003 | Tallarida et al. |
| 6,533,737 B1 | 3/2003 | Brosseau et al. |
| 6,547,823 B2 | 4/2003 | Scarborough et al. |
| 6,551,325 B2 | 4/2003 | Neubauer et al. |
| 6,554,837 B1 | 4/2003 | Hauri et al. |
| 6,554,838 B2 | 4/2003 | Mcgovern et al. |
| 6,556,008 B2 | 4/2003 | Thesen |
| 6,558,391 B2 | 5/2003 | Axelson, Jr. et al. |
| 6,558,428 B2 | 5/2003 | Park |
| 6,562,073 B2 | 5/2003 | Foley |
| 6,564,085 B2 | 5/2003 | Meaney et al. |
| 6,567,681 B1 | 5/2003 | Lindequist |
| 6,575,980 B1 | 6/2003 | Robie et al. |
| 6,575,982 B1 | 6/2003 | Bonutti |
| 6,583,630 B2 | 6/2003 | Mendes et al. |
| 6,589,283 B1 | 7/2003 | Metzger et al. |
| 6,591,581 B2 | 7/2003 | Schmieding |

(56) References Cited

U.S. PATENT DOCUMENTS

| | | |
|---|---|---|
| 6,602,259 B1 | 8/2003 | Masini |
| 6,605,293 B1 | 8/2003 | Giordano et al. |
| 6,610,067 B2 | 8/2003 | Tallarida et al. |
| 6,610,096 B2 | 8/2003 | MacDonald |
| 6,620,181 B1 | 9/2003 | Bonutti |
| 6,622,567 B1 | 9/2003 | Hamel et al. |
| 6,629,999 B1 | 10/2003 | Serafin, Jr. |
| 6,632,225 B2 | 10/2003 | Sanford et al. |
| 6,635,073 B2 | 10/2003 | Bonutti |
| 6,641,617 B1 | 11/2003 | Merrill et al. |
| 6,673,077 B1 | 1/2004 | Katz |
| 6,676,662 B1 | 1/2004 | Bagga et al. |
| 6,676,892 B1 | 1/2004 | Das et al. |
| 6,682,566 B2 | 1/2004 | Draenert et al. |
| 6,682,567 B1 | 1/2004 | Schroeder |
| 6,695,848 B2 | 2/2004 | Haines |
| 6,696,073 B2 | 2/2004 | Boyce et al. |
| 6,697,664 B2 | 2/2004 | Kienzle, III et al. |
| 6,699,289 B2 | 3/2004 | Iannotti et al. |
| 6,701,174 B1 | 3/2004 | Krause et al. |
| 6,702,821 B2 | 3/2004 | Bonutti |
| 6,709,462 B2 | 3/2004 | Hanssen |
| 6,711,431 B2 | 3/2004 | Sarin et al. |
| 6,711,432 B1 | 3/2004 | Krause et al. |
| 6,712,856 B1 | 3/2004 | Carignan et al. |
| 6,716,249 B2 | 4/2004 | Hyde |
| 6,725,077 B1 | 4/2004 | Balloni et al. |
| 6,738,657 B1 | 5/2004 | Franklin et al. |
| 6,740,092 B2 | 5/2004 | Lombardo et al. |
| 6,743,235 B2 | 6/2004 | Subba Rao |
| 6,746,487 B2 | 6/2004 | Scifert et al. |
| 6,749,638 B1 | 6/2004 | Saladiono |
| 6,750,653 B1 | 6/2004 | Zou et al. |
| 6,770,078 B2 | 8/2004 | Bonutti |
| 6,772,026 B2 | 8/2004 | Bradbury et al. |
| 6,780,190 B2 | 8/2004 | Maroney |
| 6,786,930 B2 | 9/2004 | Biscup |
| 6,799,066 B2 | 9/2004 | Steines et al. |
| 6,810,753 B2 | 11/2004 | Valdevit et al. |
| 6,821,299 B2 | 11/2004 | Kirking et al. |
| 6,823,871 B2 | 11/2004 | Schmieding |
| 6,827,723 B2 | 12/2004 | Carson |
| 6,871,549 B2 | 3/2005 | Serra et al. |
| 6,887,247 B1 | 5/2005 | Couture et al. |
| 6,905,514 B2 | 6/2005 | Carignan et al. |
| 6,916,324 B2 | 7/2005 | Sanford |
| 6,923,817 B2 | 8/2005 | Carson et al. |
| 6,923,831 B2 | 8/2005 | Fell et al. |
| 6,932,842 B1 | 8/2005 | Litschko et al. |
| 6,942,475 B2 | 9/2005 | Ensign et al. |
| 6,944,518 B2 | 9/2005 | Roose |
| 6,945,976 B2 | 9/2005 | Ball et al. |
| 6,953,480 B2 | 10/2005 | Mears et al. |
| 6,960,216 B2 | 11/2005 | Kolb et al. |
| 6,966,932 B1 | 11/2005 | Schroeder |
| 6,975,755 B1 | 12/2005 | Baumberg |
| 6,979,299 B2 | 12/2005 | Peabody et al. |
| 6,990,220 B2 | 1/2006 | Ellis et al. |
| 6,993,406 B1 | 1/2006 | Cesarano, III et al. |
| 7,001,385 B2 | 2/2006 | Bonutti |
| 7,001,393 B2 | 2/2006 | Schwenke et al. |
| 7,022,141 B2 | 4/2006 | Dwyer et al. |
| 7,029,477 B2 | 4/2006 | Grimm |
| 7,029,479 B2 | 4/2006 | Tallarida et al. |
| 7,042,222 B2 | 5/2006 | Zheng et al. |
| 7,048,741 B2 | 5/2006 | Swanson |
| 7,050,877 B2 | 5/2006 | Iseki et al. |
| 7,060,074 B2 | 6/2006 | Rosa et al. |
| 7,074,241 B2 | 7/2006 | Mckinnon |
| RE39,301 E | 9/2006 | Bertin |
| 7,104,997 B2 | 9/2006 | Lionberger et al. |
| 7,105,026 B2 | 9/2006 | Johnson et al. |
| 7,115,131 B2 | 10/2006 | Engh et al. |
| 7,121,832 B2 | 10/2006 | Hsieh et al. |
| 7,141,053 B2 | 11/2006 | Rosa et al. |
| D533,664 S | 12/2006 | Büttler et al. |
| 7,169,185 B2 | 1/2007 | Sidebotham |
| 7,172,599 B2 | 2/2007 | Steffensmeier et al. |
| 7,174,282 B2 | 2/2007 | Hollister et al. |
| 7,176,466 B2 | 2/2007 | Rousso et al. |
| 7,184,814 B2 | 2/2007 | Lang et al. |
| 7,198,628 B2 | 4/2007 | Ondrla et al. |
| 7,218,232 B2 | 5/2007 | Disilvestro et al. |
| 7,220,264 B1 | 5/2007 | Hershberger |
| 7,239,908 B1 | 7/2007 | Alexander et al. |
| 7,241,315 B2 | 7/2007 | Evans |
| 7,255,702 B2 | 8/2007 | Serra et al. |
| 7,258,701 B2 | 8/2007 | Aram et al. |
| 7,261,719 B1 | 8/2007 | Twomey et al. |
| 7,275,218 B2 | 9/2007 | Petrella et al. |
| 7,282,054 B2 | 10/2007 | Steffensmeier et al. |
| 7,291,117 B2 | 11/2007 | Boecker et al. |
| 7,291,177 B2 | 11/2007 | Gibbs |
| 7,294,133 B2 | 11/2007 | Zink et al. |
| 7,297,164 B2 | 11/2007 | Johnson et al. |
| 7,309,339 B2 | 12/2007 | Cusick et al. |
| 7,331,965 B2 | 2/2008 | Nielsen |
| 7,333,013 B2 | 2/2008 | Berger |
| 7,335,207 B1 | 2/2008 | Smith |
| 7,335,231 B2 | 2/2008 | Mclean |
| 7,338,499 B1 | 3/2008 | Kuczynski et al. |
| 7,371,260 B2 | 5/2008 | Malinin |
| 7,377,182 B2 | 5/2008 | Serra et al. |
| 7,383,164 B2 | 6/2008 | Aram et al. |
| 7,385,498 B2 | 6/2008 | Dobosz |
| 7,388,972 B2 | 6/2008 | Kitson |
| 7,390,327 B2 | 6/2008 | Collazo et al. |
| 7,392,076 B2 | 6/2008 | Moctezuma De La Barrera |
| 7,419,492 B2 | 9/2008 | Yoon et al. |
| 7,427,200 B2 | 9/2008 | Noble et al. |
| 7,427,272 B2 | 9/2008 | Richard et al. |
| 7,458,989 B2 | 12/2008 | Banks |
| 7,465,320 B1 | 12/2008 | Kito et al. |
| 7,468,075 B2 | 12/2008 | Lang et al. |
| 7,474,223 B2 | 1/2009 | Nycz et al. |
| 7,488,324 B1 | 2/2009 | Metzger et al. |
| 7,488,325 B2 | 2/2009 | Qian et al. |
| 7,494,510 B2 | 2/2009 | Zweymuller |
| 7,517,365 B2 | 4/2009 | Carignan et al. |
| 7,519,540 B2 | 4/2009 | Mayaud |
| 7,527,631 B2 | 5/2009 | Maroney et al. |
| 7,534,263 B2 | 5/2009 | Burdulis, Jr. et al. |
| 7,537,664 B2 | 5/2009 | O'neill et al. |
| 7,542,791 B2 | 6/2009 | Mire et al. |
| 7,559,931 B2 | 7/2009 | Stone |
| 7,575,602 B2 | 8/2009 | Amirouche et al. |
| 7,578,851 B2 | 8/2009 | Dong et al. |
| 7,582,091 B2 | 9/2009 | Duncan et al. |
| 7,591,821 B2 | 9/2009 | Kleman |
| 7,601,155 B2 | 10/2009 | Petersen |
| 7,603,192 B2 | 10/2009 | Martin et al. |
| 7,604,639 B2 | 10/2009 | Swanson |
| 7,611,516 B2 | 11/2009 | Maroney |
| 7,618,451 B2 | 11/2009 | Berez et al. |
| 7,621,915 B2 | 11/2009 | Frederick et al. |
| 7,625,409 B2 | 12/2009 | Saltzman et al. |
| 7,636,595 B2 | 12/2009 | Marquart |
| 7,646,161 B2 | 1/2010 | Albu-schäffer et al. |
| 7,651,501 B2 | 1/2010 | Penenberg et al. |
| 7,660,623 B2 | 2/2010 | Hunter et al. |
| 7,670,345 B2 | 3/2010 | Plassky et al. |
| 7,674,100 B2 | 3/2010 | Hayes-pankhurst et al. |
| 7,682,398 B2 | 3/2010 | Croxton et al. |
| 7,695,477 B2 | 4/2010 | Creger et al. |
| 7,695,521 B2 | 4/2010 | Ely et al. |
| 7,699,847 B2 | 4/2010 | Sheldon et al. |
| 7,702,380 B1 | 4/2010 | Dean |
| 7,704,253 B2 | 4/2010 | Bastian et al. |
| 7,723,395 B2 | 5/2010 | Ringeisen et al. |
| 7,747,305 B2 | 6/2010 | Dean et al. |
| D622,854 S | 8/2010 | Otto et al. |
| 7,780,672 B2 | 8/2010 | Metzger et al. |
| 7,780,681 B2 | 8/2010 | Sarin et al. |
| 7,780,740 B2 | 8/2010 | Steinberg |

(56) References Cited

U.S. PATENT DOCUMENTS

| | | |
|---|---|---|
| 7,789,885 B2 | 9/2010 | Metzger |
| 7,794,466 B2 | 9/2010 | Merchant et al. |
| 7,794,467 B2 | 9/2010 | McGinley et al. |
| 7,794,504 B2 | 9/2010 | Case |
| 7,806,896 B1 | 10/2010 | Bonutti |
| 7,809,184 B2 | 10/2010 | Neubauer et al. |
| 7,819,925 B2 | 10/2010 | King et al. |
| 7,828,806 B2 | 11/2010 | Graf et al. |
| 7,833,245 B2 | 11/2010 | Kaes et al. |
| 7,837,040 B2 | 11/2010 | Ward et al. |
| 7,837,690 B2 | 11/2010 | Metzger |
| 7,846,382 B2 | 12/2010 | Strand |
| 7,850,698 B2 | 12/2010 | Straszheim-Morley et al. |
| 7,854,737 B2 | 12/2010 | Daniels et al. |
| 7,879,109 B2 | 2/2011 | Borden et al. |
| 7,892,261 B2 | 2/2011 | Bonutti |
| 7,896,921 B2 | 3/2011 | Smith et al. |
| 7,926,363 B2 | 4/2011 | Miller et al. |
| 7,935,119 B2 | 5/2011 | Ammann et al. |
| 7,935,150 B2 | 5/2011 | Carignan et al. |
| 7,938,861 B2 | 5/2011 | King et al. |
| 7,959,637 B2 | 6/2011 | Fox et al. |
| 7,962,196 B2 | 6/2011 | Tuma |
| 7,963,968 B2 | 6/2011 | Dees, Jr. |
| 7,967,823 B2 | 6/2011 | Ammann et al. |
| 7,967,868 B2 | 6/2011 | White et al. |
| 7,974,677 B2 | 7/2011 | Mire et al. |
| 7,981,158 B2 | 7/2011 | Fitz et al. |
| 7,988,736 B2 | 8/2011 | May et al. |
| 7,993,353 B2 | 8/2011 | Roβner et al. |
| 8,057,482 B2 | 11/2011 | Stone et al. |
| 8,062,301 B2 | 11/2011 | Ammann et al. |
| 8,066,708 B2 | 11/2011 | Lang et al. |
| 8,070,752 B2 | 12/2011 | Metzger et al. |
| 8,083,745 B2 | 12/2011 | Lang et al. |
| 8,083,746 B2 | 12/2011 | Novak |
| 8,083,749 B2 | 12/2011 | Taber |
| 8,086,336 B2 | 12/2011 | Christensen |
| 8,092,465 B2 | 1/2012 | Metzger et al. |
| 8,105,330 B2 | 1/2012 | Fitz et al. |
| 8,109,942 B2 | 2/2012 | Carson |
| 8,122,582 B2 | 2/2012 | Burdulis, Jr. et al. |
| 8,133,230 B2 | 3/2012 | Stevens et al. |
| 8,133,234 B2 | 3/2012 | Meridew et al. |
| 8,137,406 B2 | 3/2012 | Novak et al. |
| 8,147,861 B2 | 4/2012 | Jones et al. |
| 8,160,345 B2 | 4/2012 | Pavlovskaia et al. |
| 8,167,823 B2 | 5/2012 | Nycz et al. |
| 8,167,951 B2 | 5/2012 | Ammann et al. |
| 8,170,641 B2 | 5/2012 | Belcher |
| 8,172,850 B2 | 5/2012 | Mcminn |
| 8,182,489 B2 | 5/2012 | Horacek |
| 8,192,441 B2 | 6/2012 | Collazo |
| 8,192,495 B2 | 6/2012 | Simpson et al. |
| 8,200,355 B2 | 6/2012 | Lee et al. |
| 8,211,112 B2 | 7/2012 | Novak et al. |
| 8,221,430 B2 | 7/2012 | Park et al. |
| 8,241,292 B2 | 8/2012 | Collazo |
| 8,241,293 B2 | 8/2012 | Stone et al. |
| 8,246,680 B2 | 8/2012 | Betz et al. |
| 8,260,589 B1 | 9/2012 | Kumar |
| 8,265,790 B2 | 9/2012 | Amiot et al. |
| 8,268,099 B2 | 9/2012 | O'neill et al. |
| 8,268,100 B2 | 9/2012 | O'neill et al. |
| D669,176 S | 10/2012 | Frey |
| 8,282,646 B2 | 10/2012 | Schoenfeld et al. |
| 8,298,237 B2 | 10/2012 | Schoenfeld et al. |
| 8,303,596 B2 | 11/2012 | Plaβky et al. |
| 8,313,491 B2 | 11/2012 | Green, II et al. |
| D672,038 S | 12/2012 | Frey |
| 8,333,772 B2 | 12/2012 | Fox et al. |
| 8,337,426 B2 | 12/2012 | Nycz |
| 8,337,501 B2 | 12/2012 | Fitz et al. |
| 8,337,503 B2 | 12/2012 | Lian |
| 8,355,773 B2 | 1/2013 | Leitner et al. |
| 8,372,078 B2 | 2/2013 | Collazo |
| 8,377,066 B2 | 2/2013 | Katrana et al. |
| 8,388,690 B2 | 3/2013 | Singhatat et al. |
| 8,398,646 B2 | 3/2013 | Metzger et al. |
| 8,407,067 B2 | 3/2013 | Uthgenannt et al. |
| 8,414,594 B2 | 4/2013 | Berger et al. |
| 8,419,741 B2 | 4/2013 | Carignan et al. |
| 8,425,522 B2 | 4/2013 | Bonutti |
| 8,430,882 B2 | 4/2013 | Lowry et al. |
| 8,430,931 B2 | 4/2013 | Acker et al. |
| 8,439,675 B2 | 5/2013 | De Moyer |
| 8,439,925 B2 | 5/2013 | Marino et al. |
| 8,444,564 B2 | 5/2013 | Mahfouz et al. |
| 8,444,651 B2 | 5/2013 | Kunz et al. |
| 8,457,930 B2 | 6/2013 | Schroeder |
| 8,460,302 B2 | 6/2013 | Park et al. |
| 8,469,961 B2 | 6/2013 | Alleyne et al. |
| 8,473,305 B2 | 6/2013 | Belcher et al. |
| 8,486,150 B2 | 7/2013 | White et al. |
| 8,500,740 B2 | 8/2013 | Bojarski et al. |
| 8,529,578 B2 | 9/2013 | Daniels et al. |
| 8,532,361 B2 | 9/2013 | Pavlovskaia et al. |
| 8,532,806 B1 | 9/2013 | Masson |
| 8,532,807 B2 | 9/2013 | Metzger |
| 8,535,387 B2 | 9/2013 | Meridew et al. |
| 8,543,234 B2 | 9/2013 | Gao |
| 8,545,508 B2 | 10/2013 | Collazo |
| 8,551,099 B2 | 10/2013 | Lang et al. |
| 8,568,487 B2 | 10/2013 | Witt et al. |
| 8,591,516 B2 | 11/2013 | Metzger et al. |
| 8,597,365 B2 | 12/2013 | Meridew |
| 8,603,180 B2 | 12/2013 | White et al. |
| 8,608,748 B2 | 12/2013 | Metzger et al. |
| 8,608,749 B2 | 12/2013 | Meridew et al. |
| 8,617,170 B2 | 12/2013 | Ashby et al. |
| 8,617,174 B2 | 12/2013 | Axelson, Jr. et al. |
| 8,617,175 B2 | 12/2013 | Park et al. |
| 8,632,547 B2 | 1/2014 | Maxson et al. |
| 8,652,142 B2 | 2/2014 | Geissler |
| 8,668,700 B2 | 3/2014 | Catanzarite et al. |
| 8,702,712 B2 | 4/2014 | Jordan et al. |
| 8,702,715 B2 | 4/2014 | Ammann et al. |
| 8,706,285 B2 | 4/2014 | Narainasamy et al. |
| 8,715,289 B2 | 5/2014 | Smith |
| 8,728,387 B2 | 5/2014 | Jones et al. |
| 8,735,773 B2 | 5/2014 | Lang |
| 8,764,760 B2 | 7/2014 | Metzger et al. |
| 8,775,133 B2 | 7/2014 | Schroeder |
| 8,777,875 B2 | 7/2014 | Park |
| 8,781,557 B2 | 7/2014 | Dean et al. |
| 8,828,016 B2 | 9/2014 | Major et al. |
| 8,828,087 B2 | 9/2014 | Stone et al. |
| 8,828,089 B1 | 9/2014 | Perez et al. |
| 8,834,568 B2 | 9/2014 | Shapiro |
| 8,858,561 B2 | 10/2014 | White et al. |
| 8,864,769 B2 | 10/2014 | Stone et al. |
| 8,900,244 B2 | 12/2014 | Meridew et al. |
| 8,903,530 B2 | 12/2014 | Metzger |
| 8,956,364 B2 | 2/2015 | Catanzarite |
| 8,979,936 B2 | 3/2015 | White et al. |
| 8,986,309 B1 | 3/2015 | Murphy |
| 9,005,297 B2 | 4/2015 | Katrana et al. |
| 9,060,788 B2 | 6/2015 | Bollinger |
| 9,066,734 B2 | 6/2015 | Schoenefeld et al. |
| 9,107,139 B2 | 8/2015 | Sirotkin et al. |
| 9,113,971 B2 | 8/2015 | Metzger et al. |
| 9,173,661 B2 | 11/2015 | Metzger et al. |
| 9,186,254 B2 | 11/2015 | Fitz et al. |
| 9,208,558 B2 | 12/2015 | Dean et al. |
| 9,241,745 B2 | 1/2016 | Smith et al. |
| 9,271,744 B2 | 3/2016 | Meridew |
| 9,275,191 B2 | 3/2016 | Dean et al. |
| 9,289,253 B2 | 3/2016 | Vanasse et al. |
| 9,292,920 B2 | 3/2016 | Dean et al. |
| 9,330,206 B2 | 5/2016 | Dean et al. |
| 9,339,278 B2 | 5/2016 | Meridew et al. |
| 9,345,548 B2 | 5/2016 | Schoenefeld et al. |
| 9,445,907 B2 | 9/2016 | Meridew et al. |
| 9,468,538 B2 | 10/2016 | Nycz et al. |

(56) References Cited

U.S. PATENT DOCUMENTS

| | | |
|---|---|---|
| 9,480,490 B2 | 11/2016 | Metzger et al. |
| 9,480,580 B2 | 11/2016 | White et al. |
| 9,522,010 B2 | 12/2016 | Metzger et al. |
| 9,539,013 B2 | 1/2017 | Katrana et al. |
| 9,662,127 B2 | 5/2017 | Meridew et al. |
| 9,662,216 B2 | 5/2017 | Witt et al. |
| 9,700,329 B2 | 7/2017 | Metzger et al. |
| 2001/0005797 A1 | 6/2001 | Barlow et al. |
| 2001/0011190 A1 | 8/2001 | Park |
| 2001/0018589 A1 | 8/2001 | Muller |
| 2001/0021876 A1 | 9/2001 | Terrill-Grisoni et al. |
| 2001/0034554 A1 | 10/2001 | Pappas |
| 2001/0037155 A1 | 11/2001 | Merchant |
| 2001/0054478 A1 | 12/2001 | Watanabe et al. |
| 2002/0007294 A1 | 1/2002 | Bradbury et al. |
| 2002/0029038 A1 | 3/2002 | Haines |
| 2002/0029045 A1 | 3/2002 | Bonutti |
| 2002/0052606 A1 | 5/2002 | Bonutti |
| 2002/0059049 A1 | 5/2002 | Bradbury et al. |
| 2002/0077540 A1 | 6/2002 | Kienzle, III |
| 2002/0082741 A1 | 6/2002 | Mazumder et al. |
| 2002/0087274 A1 | 7/2002 | Alexander et al. |
| 2002/0092532 A1 | 7/2002 | Yoon |
| 2002/0107522 A1 | 8/2002 | Picard et al. |
| 2002/0107523 A1 | 8/2002 | Naughton et al. |
| 2002/0116023 A1 | 8/2002 | Fletcher et al. |
| 2002/0120342 A1 | 8/2002 | Gibbs |
| 2002/0128872 A1 | 9/2002 | Giammattei |
| 2002/0147415 A1 | 10/2002 | Martelli |
| 2002/0173797 A1 | 11/2002 | Van Zile et al. |
| 2002/0186818 A1 | 12/2002 | Arnaud et al. |
| 2002/0193797 A1 | 12/2002 | Johnson et al. |
| 2002/0198528 A1 | 12/2002 | Engh et al. |
| 2002/0198529 A1 | 12/2002 | Masini |
| 2002/0198531 A1 | 12/2002 | Millard et al. |
| 2003/0009171 A1 | 1/2003 | Tornier |
| 2003/0009234 A1 | 1/2003 | Treacy et al. |
| 2003/0011624 A1 | 1/2003 | Ellis |
| 2003/0018338 A1 | 1/2003 | Axelson, Jr. et al. |
| 2003/0028196 A1 | 2/2003 | Bonutti |
| 2003/0039676 A1 | 2/2003 | Boyce et al. |
| 2003/0055502 A1 | 3/2003 | Lang et al. |
| 2003/0060831 A1 | 3/2003 | Bonutti |
| 2003/0069897 A1 | 4/2003 | Roy et al. |
| 2003/0074800 A1 | 4/2003 | Huang |
| 2003/0100906 A1 | 5/2003 | Rosa et al. |
| 2003/0100907 A1 | 5/2003 | Rosa et al. |
| 2003/0105526 A1 | 6/2003 | Bryant et al. |
| 2003/0109784 A1 | 6/2003 | Loh et al. |
| 2003/0120276 A1 | 6/2003 | Tallarida et al. |
| 2003/0130665 A1 | 7/2003 | Pinczewski et al. |
| 2003/0130741 A1 | 7/2003 | McMinn |
| 2003/0139817 A1 | 7/2003 | Tuke et al. |
| 2003/0153829 A1 | 8/2003 | Sarin et al. |
| 2003/0158606 A1 | 8/2003 | Coon et al. |
| 2003/0171757 A1 | 9/2003 | Coon et al. |
| 2003/0181987 A1 | 9/2003 | Muirhead-allwood |
| 2003/0212403 A1 | 11/2003 | Swanson |
| 2003/0212459 A1 | 11/2003 | Gibbs |
| 2003/0216669 A1 | 11/2003 | Lang et al. |
| 2003/0216741 A1 | 11/2003 | Sanford et al. |
| 2003/0220641 A1 | 11/2003 | Thelen et al. |
| 2003/0225413 A1 | 12/2003 | Sanford et al. |
| 2004/0018144 A1 | 1/2004 | Briscoe |
| 2004/0030245 A1 | 2/2004 | Noble et al. |
| 2004/0034302 A1 | 2/2004 | Abovitz et al. |
| 2004/0039395 A1 | 2/2004 | Coon et al. |
| 2004/0044295 A1 | 3/2004 | Reinert et al. |
| 2004/0054372 A1 | 3/2004 | Corden et al. |
| 2004/0054416 A1 | 3/2004 | Wyss et al. |
| 2004/0068187 A1 | 4/2004 | Krause et al. |
| 2004/0092932 A1 | 5/2004 | Aubin et al. |
| 2004/0097952 A1 | 5/2004 | Sarin et al. |
| 2004/0098133 A1 | 5/2004 | Carignan et al. |
| 2004/0102785 A1 | 5/2004 | Hodorek et al. |
| 2004/0102792 A1 | 5/2004 | Sarin et al. |
| 2004/0102852 A1 | 5/2004 | Johnson et al. |
| 2004/0102866 A1 | 5/2004 | Harris et al. |
| 2004/0106926 A1 | 6/2004 | Leitner et al. |
| 2004/0115586 A1 | 6/2004 | Andreiko et al. |
| 2004/0117026 A1 | 6/2004 | Tuma et al. |
| 2004/0122436 A1 | 6/2004 | Grimm |
| 2004/0122439 A1 | 6/2004 | Dwyer et al. |
| 2004/0128026 A1 | 7/2004 | Harris et al. |
| 2004/0133276 A1 | 7/2004 | Lang et al. |
| 2004/0138670 A1 | 7/2004 | Metzger |
| 2004/0138754 A1 | 7/2004 | Lang et al. |
| 2004/0143336 A1 | 7/2004 | Burkinshaw |
| 2004/0147927 A1 | 7/2004 | Tsougarakis et al. |
| 2004/0148026 A1 | 7/2004 | Bonutti |
| 2004/0153079 A1 | 8/2004 | Tsougarakis et al. |
| 2004/0153087 A1 | 8/2004 | Sanford et al. |
| 2004/0158254 A1 | 8/2004 | Eisermann |
| 2004/0162619 A1 | 8/2004 | Blaylock et al. |
| 2004/0167390 A1 | 8/2004 | Alexander et al. |
| 2004/0171924 A1 | 9/2004 | Mire et al. |
| 2004/0172137 A1 | 9/2004 | Blaylock et al. |
| 2004/0181144 A1 | 9/2004 | Cinquin et al. |
| 2004/0193169 A1 | 9/2004 | Schon et al. |
| 2004/0204644 A1 | 10/2004 | Tsougarakis et al. |
| 2004/0204760 A1 | 10/2004 | Fitz et al. |
| 2004/0212586 A1 | 10/2004 | Denny |
| 2004/0220583 A1 | 11/2004 | Pieczynski, II et al. |
| 2004/0225369 A1 | 11/2004 | Lakin et al. |
| 2004/0230199 A1 | 11/2004 | Jansen et al. |
| 2004/0236341 A1 | 11/2004 | Petersen |
| 2004/0236424 A1 | 11/2004 | Berez et al. |
| 2004/0243148 A1 | 12/2004 | Wasielewski |
| 2004/0243481 A1 | 12/2004 | Bradbury et al. |
| 2004/0249386 A1 | 12/2004 | Faoro |
| 2004/0254584 A1 | 12/2004 | Sarin et al. |
| 2004/0260301 A1 | 12/2004 | Lionberger et al. |
| 2005/0008887 A1 | 1/2005 | Haymann et al. |
| 2005/0009952 A1 | 1/2005 | Qian et al. |
| 2005/0010227 A1 | 1/2005 | Paul |
| 2005/0010300 A1 | 1/2005 | Disilvestro et al. |
| 2005/0015022 A1 | 1/2005 | Richard et al. |
| 2005/0015599 A1 | 1/2005 | Wang et al. |
| 2005/0015603 A1 | 1/2005 | Cabezas et al. |
| 2005/0015604 A1 | 1/2005 | Sundararajan et al. |
| 2005/0015605 A1 | 1/2005 | Lin et al. |
| 2005/0019664 A1 | 1/2005 | Matsumoto |
| 2005/0021044 A1 | 1/2005 | Stone et al. |
| 2005/0021148 A1 | 1/2005 | Gibbs |
| 2005/0021299 A1 | 1/2005 | Kadota et al. |
| 2005/0021494 A1 | 1/2005 | Wilkinson |
| 2005/0027303 A1 | 2/2005 | Lionberger et al. |
| 2005/0027361 A1 | 2/2005 | Reiley |
| 2005/0043806 A1 | 2/2005 | Cook et al. |
| 2005/0043837 A1 | 2/2005 | Rubbert et al. |
| 2005/0049524 A1 | 3/2005 | Lefevre et al. |
| 2005/0049603 A1 | 3/2005 | Calton et al. |
| 2005/0059873 A1 | 3/2005 | Glozman et al. |
| 2005/0060040 A1 | 3/2005 | Auxepaules et al. |
| 2005/0065617 A1 | 3/2005 | Moctezuma De La Barrera et al. |
| 2005/0065628 A1 | 3/2005 | Roose |
| 2005/0070897 A1 | 3/2005 | Petersen |
| 2005/0071015 A1 | 3/2005 | Sekel |
| 2005/0075641 A1 | 4/2005 | Singhatat et al. |
| 2005/0096535 A1 | 5/2005 | De La Barrera |
| 2005/0109855 A1 | 5/2005 | Mccombs |
| 2005/0113659 A1 | 5/2005 | Pothier et al. |
| 2005/0113840 A1 | 5/2005 | Metzger et al. |
| 2005/0113841 A1 | 5/2005 | Sheldon et al. |
| 2005/0113846 A1 | 5/2005 | Carson |
| 2005/0119664 A1 | 6/2005 | Carignan et al. |
| 2005/0131662 A1 | 6/2005 | Ascenzi et al. |
| 2005/0137708 A1 | 6/2005 | Clark |
| 2005/0143828 A1 | 6/2005 | Collins et al. |
| 2005/0148843 A1 | 7/2005 | Roose |
| 2005/0149042 A1 | 7/2005 | Metzger |
| 2005/0171545 A1 | 8/2005 | Walsh et al. |
| 2005/0177170 A1 | 8/2005 | Fisher et al. |
| 2005/0177245 A1 | 8/2005 | Leatherbury et al. |

(56) References Cited

U.S. PATENT DOCUMENTS

| | | |
|---|---|---|
| 2005/0203384 A1 | 9/2005 | Sati et al. |
| 2005/0203536 A1 | 9/2005 | Laffargue et al. |
| 2005/0203540 A1 | 9/2005 | Broyles |
| 2005/0209597 A1 | 9/2005 | Long et al. |
| 2005/0209605 A1 | 9/2005 | Grimm et al. |
| 2005/0216305 A1 | 9/2005 | Funderud |
| 2005/0222571 A1 | 10/2005 | Ryan |
| 2005/0222573 A1 | 10/2005 | Branch et al. |
| 2005/0228393 A1 | 10/2005 | Williams, III et al. |
| 2005/0234332 A1 | 10/2005 | Murphy |
| 2005/0234461 A1 | 10/2005 | Burdulis, Jr. et al. |
| 2005/0234465 A1 | 10/2005 | Mccombs et al. |
| 2005/0234468 A1 | 10/2005 | Carson |
| 2005/0240195 A1 | 10/2005 | Axelson, Jr. et al. |
| 2005/0240267 A1 | 10/2005 | Randall et al. |
| 2005/0244239 A1 | 11/2005 | Shimp |
| 2005/0245808 A1 | 11/2005 | Carson |
| 2005/0245934 A1 | 11/2005 | Tuke et al. |
| 2005/0245936 A1 | 11/2005 | Tuke et al. |
| 2005/0251026 A1 | 11/2005 | Stone |
| 2005/0251147 A1 | 11/2005 | Novak |
| 2005/0267353 A1 | 12/2005 | Marquart et al. |
| 2005/0267485 A1 | 12/2005 | Cordes et al. |
| 2005/0267584 A1 | 12/2005 | Burdulis, Jr. et al. |
| 2005/0273114 A1 | 12/2005 | Novak |
| 2005/0283252 A1 | 12/2005 | Coon et al. |
| 2005/0283253 A1 | 12/2005 | Coon et al. |
| 2006/0004284 A1 | 1/2006 | Grunschlager et al. |
| 2006/0015120 A1 | 1/2006 | Richard et al. |
| 2006/0025778 A1 | 2/2006 | Ferree |
| 2006/0030853 A1 | 2/2006 | Haines |
| 2006/0038520 A1 | 2/2006 | Negoro |
| 2006/0052725 A1 | 3/2006 | Santilli |
| 2006/0058803 A1 | 3/2006 | Cuckler et al. |
| 2006/0058809 A1 | 3/2006 | Zink et al. |
| 2006/0058884 A1 | 3/2006 | Aram et al. |
| 2006/0058886 A1 | 3/2006 | Wozencroft |
| 2006/0069444 A1 | 3/2006 | Deffenbaugh |
| 2006/0089621 A1 | 4/2006 | Fard |
| 2006/0093988 A1 | 5/2006 | Swaelens et al. |
| 2006/0094951 A1 | 5/2006 | Dean et al. |
| 2006/0094958 A1 | 5/2006 | Marquart et al. |
| 2006/0095044 A1 | 5/2006 | Grady, Jr. et al. |
| 2006/0095047 A1 | 5/2006 | De La Barrera |
| 2006/0095049 A1 | 5/2006 | Zannis et al. |
| 2006/0100832 A1 | 5/2006 | Bowman |
| 2006/0105011 A1 | 5/2006 | Sun et al. |
| 2006/0111722 A1 | 5/2006 | Bouadi |
| 2006/0122491 A1 | 6/2006 | Murray et al. |
| 2006/0122616 A1 | 6/2006 | Bennett et al. |
| 2006/0122618 A1 | 6/2006 | Claypool et al. |
| 2006/0136058 A1 | 6/2006 | Pietrzak |
| 2006/0142657 A1 | 6/2006 | Quaid et al. |
| 2006/0142774 A1 | 6/2006 | Metzger |
| 2006/0142778 A1 | 6/2006 | Dees |
| 2006/0147332 A1 | 7/2006 | Jones et al. |
| 2006/0149283 A1 | 7/2006 | May et al. |
| 2006/0155380 A1 | 7/2006 | Clemow et al. |
| 2006/0161165 A1 | 7/2006 | Swanson et al. |
| 2006/0161167 A1 | 7/2006 | Myers et al. |
| 2006/0172263 A1 | 8/2006 | Quadling et al. |
| 2006/0178497 A1 | 8/2006 | Gevaert et al. |
| 2006/0184177 A1 | 8/2006 | Echeverri |
| 2006/0184250 A1 | 8/2006 | Bandoh et al. |
| 2006/0190086 A1 | 8/2006 | Clemow et al. |
| 2006/0192319 A1 | 8/2006 | Solar |
| 2006/0195111 A1 | 8/2006 | Couture |
| 2006/0195194 A1 | 8/2006 | Gunther |
| 2006/0195198 A1 | 8/2006 | James |
| 2006/0198943 A1 | 9/2006 | Kumar |
| 2006/0200158 A1 | 9/2006 | Farling et al. |
| 2006/0204932 A1 | 9/2006 | Haymann et al. |
| 2006/0210644 A1 | 9/2006 | Levin |
| 2006/0217808 A1 | 9/2006 | Novak |
| 2006/0235421 A1 | 10/2006 | Rosa et al. |
| 2006/0241635 A1 | 10/2006 | Stumpo et al. |
| 2006/0241636 A1 | 10/2006 | Novak et al. |
| 2006/0241775 A1 | 10/2006 | Buss |
| 2006/0241776 A1 | 10/2006 | Brown et al. |
| 2006/0241781 A1 | 10/2006 | Brown et al. |
| 2006/0271058 A1 | 11/2006 | Ashton et al. |
| 2006/0276796 A1 | 12/2006 | Creger et al. |
| 2006/0276797 A1 | 12/2006 | Botimer |
| 2006/0287733 A1 | 12/2006 | Bonutti |
| 2006/0287891 A1 | 12/2006 | Grasso et al. |
| 2006/0293681 A1 | 12/2006 | Claypool et al. |
| 2007/0015995 A1 | 1/2007 | Lang et al. |
| 2007/0016008 A1 | 1/2007 | Schoenefeld |
| 2007/0016209 A1 | 1/2007 | Ammann et al. |
| 2007/0027680 A1 | 2/2007 | Ashley et al. |
| 2007/0039205 A1 | 2/2007 | Erb et al. |
| 2007/0043582 A1 | 2/2007 | Peveto et al. |
| 2007/0066917 A1 | 3/2007 | Hodorek et al. |
| 2007/0073133 A1 | 3/2007 | Schoenefeld |
| 2007/0073136 A1 | 3/2007 | Metzger |
| 2007/0073137 A1 | 3/2007 | Schoenefeld |
| 2007/0083209 A1 | 4/2007 | Schenberger et al. |
| 2007/0083214 A1 | 4/2007 | Duncan et al. |
| 2007/0083266 A1 | 4/2007 | Lang |
| 2007/0100258 A1 | 5/2007 | Shoham et al. |
| 2007/0100450 A1 | 5/2007 | Hodorek |
| 2007/0100462 A1 | 5/2007 | Lang et al. |
| 2007/0106299 A1 | 5/2007 | Manspeizer |
| 2007/0106391 A1 | 5/2007 | Ronk |
| 2007/0118055 A1 | 5/2007 | Mccombs |
| 2007/0118138 A1 | 5/2007 | Seo et al. |
| 2007/0118243 A1 | 5/2007 | Schroeder et al. |
| 2007/0129809 A1 | 6/2007 | Meridew et al. |
| 2007/0142914 A1 | 6/2007 | Jones et al. |
| 2007/0149981 A1 | 6/2007 | Bhattacharyya |
| 2007/0150068 A1 | 6/2007 | Dong et al. |
| 2007/0156066 A1 | 7/2007 | Mcginley et al. |
| 2007/0156171 A1 | 7/2007 | Lang et al. |
| 2007/0162038 A1 | 7/2007 | Tuke |
| 2007/0162039 A1 | 7/2007 | Wozencroft |
| 2007/0173946 A1 | 7/2007 | Bonutti |
| 2007/0173948 A1 | 7/2007 | Meridew et al. |
| 2007/0179739 A1 | 8/2007 | Donofrio et al. |
| 2007/0185498 A2 | 8/2007 | Lavallee |
| 2007/0191962 A1 | 8/2007 | Jones |
| 2007/0198022 A1 | 8/2007 | Lang et al. |
| 2007/0203430 A1 | 8/2007 | Lang et al. |
| 2007/0203583 A1 | 8/2007 | Slone |
| 2007/0203605 A1 | 8/2007 | Melton et al. |
| 2007/0219562 A1 | 9/2007 | Slone et al. |
| 2007/0219639 A1 | 9/2007 | Otto et al. |
| 2007/0219640 A1 | 9/2007 | Steinberg |
| 2007/0224238 A1 | 9/2007 | Mansmann et al. |
| 2007/0225719 A1 | 9/2007 | Stone et al. |
| 2007/0226986 A1 | 10/2007 | Park et al. |
| 2007/0233121 A1 | 10/2007 | Carson et al. |
| 2007/0233136 A1 | 10/2007 | Wozencroft |
| 2007/0233140 A1 | 10/2007 | Metzger et al. |
| 2007/0233141 A1 | 10/2007 | Park et al. |
| 2007/0233269 A1 | 10/2007 | Steines et al. |
| 2007/0233272 A1 | 10/2007 | Boyce et al. |
| 2007/0238069 A1 | 10/2007 | Lovald et al. |
| 2007/0239282 A1 | 10/2007 | Caylor, III et al. |
| 2007/0239481 A1 | 10/2007 | Disilvestro et al. |
| 2007/0244457 A1 | 10/2007 | Fangrow |
| 2007/0244487 A1 | 10/2007 | Ammann et al. |
| 2007/0250169 A1 | 10/2007 | Lang |
| 2007/0250175 A1 | 10/2007 | Meridew et al. |
| 2007/0253617 A1 | 11/2007 | Arata et al. |
| 2007/0255030 A1 | 11/2007 | Sakamoto et al. |
| 2007/0255255 A1 | 11/2007 | Shah et al. |
| 2007/0255288 A1 | 11/2007 | Mahfouz et al. |
| 2007/0255412 A1 | 11/2007 | Hajaj et al. |
| 2007/0262567 A1 | 11/2007 | Benson |
| 2007/0262867 A1 | 11/2007 | Westrick et al. |
| 2007/0270680 A1 | 11/2007 | Sheffer et al. |
| 2007/0272747 A1 | 11/2007 | Woods et al. |
| 2007/0276224 A1 | 11/2007 | Lang et al. |
| 2007/0276400 A1 | 11/2007 | Moore et al. |

(56) References Cited

U.S. PATENT DOCUMENTS

| | | |
|---|---|---|
| 2007/0276501 A1 | 11/2007 | Betz et al. |
| 2007/0282451 A1 | 12/2007 | Metzger et al. |
| 2007/0288029 A1 | 12/2007 | Justin et al. |
| 2007/0288030 A1* | 12/2007 | Metzger ............... A61B 17/154 606/87 |
| 2008/0009874 A1 | 1/2008 | Meridew et al. |
| 2008/0009952 A1 | 1/2008 | Hodge |
| 2008/0014618 A1 | 1/2008 | Bathe et al. |
| 2008/0015599 A1 | 1/2008 | D'alessio et al. |
| 2008/0015603 A1 | 1/2008 | Collazo |
| 2008/0015604 A1 | 1/2008 | Collazo |
| 2008/0015605 A1 | 1/2008 | Collazo |
| 2008/0015607 A1 | 1/2008 | D'Alessio et al. |
| 2008/0021299 A1 | 1/2008 | Meulink |
| 2008/0021494 A1 | 1/2008 | Schmelzeisen-redeker et al. |
| 2008/0021567 A1 | 1/2008 | Meulink et al. |
| 2008/0027563 A1 | 1/2008 | Johnson et al. |
| 2008/0033442 A1 | 2/2008 | Amiot et al. |
| 2008/0039850 A1 | 2/2008 | Rowley et al. |
| 2008/0051799 A1 | 2/2008 | Bonutti et al. |
| 2008/0051910 A1 | 2/2008 | Kammerzell et al. |
| 2008/0058945 A1 | 3/2008 | Hajaj et al. |
| 2008/0058947 A1 | 3/2008 | Earl et al. |
| 2008/0062183 A1 | 3/2008 | Swaelens |
| 2008/0065225 A1 | 3/2008 | Wasielewski et al. |
| 2008/0094396 A1 | 4/2008 | Sabczynsdi et al. |
| 2008/0097451 A1 | 4/2008 | Chen et al. |
| 2008/0112996 A1 | 5/2008 | Harlow et al. |
| 2008/0114370 A1 | 5/2008 | Schoenefeld |
| 2008/0133016 A1 | 6/2008 | Heinz |
| 2008/0133022 A1 | 6/2008 | Caylor |
| 2008/0140081 A1 | 6/2008 | Heavener et al. |
| 2008/0140209 A1 | 6/2008 | Iannotti et al. |
| 2008/0140213 A1 | 6/2008 | Ammann et al. |
| 2008/0146969 A1 | 6/2008 | Kurtz |
| 2008/0147072 A1 | 6/2008 | Park et al. |
| 2008/0147073 A1 | 6/2008 | Ammann et al. |
| 2008/0147074 A1 | 6/2008 | Ammann et al. |
| 2008/0161815 A1 | 7/2008 | Schoenefeld et al. |
| 2008/0161816 A1 | 7/2008 | Stevens et al. |
| 2008/0172125 A1 | 7/2008 | Ek |
| 2008/0195099 A1 | 8/2008 | Minas |
| 2008/0195107 A1 | 8/2008 | Cuckler et al. |
| 2008/0195108 A1 | 8/2008 | Bhatnagar et al. |
| 2008/0195109 A1 | 8/2008 | Hunter et al. |
| 2008/0195216 A1 | 8/2008 | Philipp |
| 2008/0200926 A1 | 8/2008 | Verard et al. |
| 2008/0208200 A1 | 8/2008 | Crofford |
| 2008/0208353 A1 | 8/2008 | Kumar et al. |
| 2008/0215059 A1 | 9/2008 | Carignan et al. |
| 2008/0221699 A1 | 9/2008 | Meridew et al. |
| 2008/0230422 A1 | 9/2008 | Pleil et al. |
| 2008/0234664 A1 | 9/2008 | May et al. |
| 2008/0234683 A1 | 9/2008 | May |
| 2008/0234685 A1 | 9/2008 | Gjerde |
| 2008/0234833 A1 | 9/2008 | Bandoh et al. |
| 2008/0243127 A1 | 10/2008 | Lang et al. |
| 2008/0249395 A1 | 10/2008 | Shachar et al. |
| 2008/0255674 A1 | 10/2008 | Rahaman et al. |
| 2008/0257363 A1 | 10/2008 | Schoenefeld et al. |
| 2008/0262499 A1 | 10/2008 | Giori et al. |
| 2008/0262500 A1 | 10/2008 | Collazo |
| 2008/0262624 A1 | 10/2008 | White et al. |
| 2008/0269596 A1 | 10/2008 | Revie et al. |
| 2008/0269906 A1 | 10/2008 | Iannotti et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287926 A1 | 11/2008 | Abou El |
| 2008/0287954 A1 | 11/2008 | Kunz et al. |
| 2008/0287959 A1 | 11/2008 | Quest et al. |
| 2008/0294170 A1 | 11/2008 | O'brien |
| 2008/0294266 A1 | 11/2008 | Steinberg |
| 2008/0300600 A1 | 12/2008 | Guelat et al. |
| 2008/0306485 A1 | 12/2008 | Coon et al. |
| 2008/0306558 A1 | 12/2008 | Hakki |
| 2008/0312659 A1 | 12/2008 | Metzger et al. |
| 2008/0319448 A1 | 12/2008 | Lavallee et al. |
| 2009/0012526 A1 | 1/2009 | Fletcher |
| 2009/0018546 A1 | 1/2009 | Daley |
| 2009/0018666 A1 | 1/2009 | Grundei et al. |
| 2009/0022015 A1 | 1/2009 | Harrison |
| 2009/0024131 A1 | 1/2009 | Metzger et al. |
| 2009/0024169 A1 | 1/2009 | Triplett et al. |
| 2009/0043556 A1 | 2/2009 | Axelson et al. |
| 2009/0048618 A1 | 2/2009 | Harrison et al. |
| 2009/0066936 A1 | 3/2009 | Huang et al. |
| 2009/0076371 A1 | 3/2009 | Lang et al. |
| 2009/0076512 A1 | 3/2009 | Ammann et al. |
| 2009/0076520 A1 | 3/2009 | Choi |
| 2009/0076555 A1 | 3/2009 | Lowry et al. |
| 2009/0082770 A1 | 3/2009 | Worner et al. |
| 2009/0082774 A1 | 3/2009 | Oti et al. |
| 2009/0087276 A1 | 4/2009 | Rose |
| 2009/0088674 A1 | 4/2009 | Caillouette et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0088865 A1 | 4/2009 | Brehm |
| 2009/0088866 A1 | 4/2009 | Case |
| 2009/0089034 A1 | 4/2009 | Penney et al. |
| 2009/0089081 A1 | 4/2009 | Haddad |
| 2009/0093815 A1 | 4/2009 | Fletcher et al. |
| 2009/0093816 A1 | 4/2009 | Roose et al. |
| 2009/0096613 A1 | 4/2009 | Westrick |
| 2009/0099567 A1 | 4/2009 | Zajac |
| 2009/0099570 A1 | 4/2009 | Paradis et al. |
| 2009/0105837 A1 | 4/2009 | Lafosse et al. |
| 2009/0116621 A1 | 5/2009 | Yuan et al. |
| 2009/0118736 A1 | 5/2009 | Kreuzer |
| 2009/0118769 A1 | 5/2009 | Sixto, Jr. et al. |
| 2009/0129067 A1 | 5/2009 | Fan |
| 2009/0131941 A1 | 5/2009 | Park et al. |
| 2009/0131942 A1 | 5/2009 | Aker et al. |
| 2009/0138019 A1 | 5/2009 | Wasielewski |
| 2009/0138020 A1 | 5/2009 | Park et al. |
| 2009/0149964 A1 | 6/2009 | May et al. |
| 2009/0149965 A1 | 6/2009 | Quaid |
| 2009/0149977 A1 | 6/2009 | Schendel |
| 2009/0151736 A1 | 6/2009 | Belcher et al. |
| 2009/0157083 A1 | 6/2009 | Park et al. |
| 2009/0163922 A1 | 6/2009 | Meridew et al. |
| 2009/0163923 A1 | 6/2009 | Flett et al. |
| 2009/0164024 A1 | 6/2009 | Rudan et al. |
| 2009/0177282 A1 | 7/2009 | Bureau et al. |
| 2009/0187193 A1 | 7/2009 | Maroney et al. |
| 2009/0204225 A1 | 8/2009 | Meridew et al. |
| 2009/0209884 A1 | 8/2009 | Van Vorhis et al. |
| 2009/0209961 A1 | 8/2009 | Ferrante et al. |
| 2009/0210067 A1 | 8/2009 | Meridew |
| 2009/0222014 A1 | 9/2009 | Bojarski et al. |
| 2009/0222015 A1 | 9/2009 | Park et al. |
| 2009/0222016 A1 | 9/2009 | Park et al. |
| 2009/0222103 A1 | 9/2009 | Fitz et al. |
| 2009/0226068 A1 | 9/2009 | Fitz et al. |
| 2009/0228016 A1 | 9/2009 | Alvarez |
| 2009/0234217 A1 | 9/2009 | Mire et al. |
| 2009/0234302 A1 | 9/2009 | Hoendervoogt et al. |
| 2009/0234360 A1 | 9/2009 | Alexander |
| 2009/0248044 A1 | 10/2009 | Amiot et al. |
| 2009/0250413 A1 | 10/2009 | Hoeppner |
| 2009/0254093 A1 | 10/2009 | White et al. |
| 2009/0254367 A1 | 10/2009 | Belcher et al. |
| 2009/0259312 A1 | 10/2009 | Shterling et al. |
| 2009/0270868 A1 | 10/2009 | Park et al. |
| 2009/0274350 A1 | 11/2009 | Pavlovskaia et al. |
| 2009/0287217 A1 | 11/2009 | Ammann et al. |
| 2009/0287309 A1 | 11/2009 | Walch et al. |

(56) References Cited

U.S. PATENT DOCUMENTS

| | | |
|---|---|---|
| 2009/0306676 A1 | 12/2009 | Lang et al. |
| 2009/0307893 A1 | 12/2009 | Burdulis, Jr. et al. |
| 2009/0318836 A1 | 12/2009 | Stone et al. |
| 2009/0318921 A1 | 12/2009 | White et al. |
| 2009/0318930 A1 | 12/2009 | Stone et al. |
| 2009/0318931 A1 | 12/2009 | Stone et al. |
| 2010/0010493 A1 | 1/2010 | Dower |
| 2010/0015082 A1 | 1/2010 | Ting-jenulis et al. |
| 2010/0016705 A1 | 1/2010 | Stone et al. |
| 2010/0016984 A1 | 1/2010 | Trabish |
| 2010/0016986 A1 | 1/2010 | Trabish |
| 2010/0023015 A1 | 1/2010 | Park |
| 2010/0030231 A1 | 2/2010 | Revie et al. |
| 2010/0036404 A1 | 2/2010 | Yi et al. |
| 2010/0042105 A1 | 2/2010 | Park et al. |
| 2010/0049195 A1 | 2/2010 | Park et al. |
| 2010/0049327 A1 | 2/2010 | Isch et al. |
| 2010/0057088 A1 | 3/2010 | Shah |
| 2010/0076439 A1 | 3/2010 | Hatch |
| 2010/0076505 A1 | 3/2010 | Borja |
| 2010/0076563 A1 | 3/2010 | Otto et al. |
| 2010/0076571 A1 | 3/2010 | Hatch |
| 2010/0082034 A1 | 4/2010 | Remia |
| 2010/0082035 A1 | 4/2010 | Keefer |
| 2010/0082067 A1 | 4/2010 | Kondrashov |
| 2010/0087829 A1 | 4/2010 | Metzger et al. |
| 2010/0094295 A1 | 4/2010 | Schnieders et al. |
| 2010/0099977 A1 | 4/2010 | Hershberger |
| 2010/0100011 A1 | 4/2010 | Roche |
| 2010/0105011 A1 | 4/2010 | Karkar et al. |
| 2010/0121334 A1 | 5/2010 | Couture et al. |
| 2010/0121335 A1 | 5/2010 | Penenberg et al. |
| 2010/0131073 A1 | 5/2010 | Meridew et al. |
| 2010/0136214 A1 | 6/2010 | Kumar |
| 2010/0137869 A1 | 6/2010 | Borja et al. |
| 2010/0137871 A1 | 6/2010 | Borja |
| 2010/0137924 A1 | 6/2010 | Tuke et al. |
| 2010/0139377 A1 | 6/2010 | Huang et al. |
| 2010/0145343 A1 | 6/2010 | Johnson et al. |
| 2010/0145344 A1 | 6/2010 | Jordan et al. |
| 2010/0145466 A1 | 6/2010 | Slone |
| 2010/0152782 A1 | 6/2010 | Stone et al. |
| 2010/0160917 A1 | 6/2010 | Fitz et al. |
| 2010/0160919 A1 | 6/2010 | Axelson, Jr. et al. |
| 2010/0168752 A1 | 7/2010 | Edwards |
| 2010/0168754 A1 | 7/2010 | Fitz et al. |
| 2010/0168857 A1 | 7/2010 | Hatch |
| 2010/0168866 A1 | 7/2010 | Shih |
| 2010/0179663 A1 | 7/2010 | Steinberg |
| 2010/0185202 A1 | 7/2010 | Lester et al. |
| 2010/0191244 A1 | 7/2010 | White et al. |
| 2010/0198067 A1 | 8/2010 | Mahfouz et al. |
| 2010/0198224 A1 | 8/2010 | Metzger |
| 2010/0212138 A1 | 8/2010 | Carroll et al. |
| 2010/0217109 A1 | 8/2010 | Belcher |
| 2010/0217270 A1 | 8/2010 | Polinski et al. |
| 2010/0217336 A1 | 8/2010 | Crawford et al. |
| 2010/0217338 A1 | 8/2010 | Carroll et al. |
| 2010/0217399 A1 | 8/2010 | Groh |
| 2010/0228257 A1 | 9/2010 | Bonutti |
| 2010/0249657 A1 | 9/2010 | Nycz et al. |
| 2010/0249796 A1 | 9/2010 | Nycz |
| 2010/0256649 A1 | 10/2010 | Capsal et al. |
| 2010/0262150 A1 | 10/2010 | Lian |
| 2010/0274253 A1 | 10/2010 | Ure |
| 2010/0281678 A1 | 11/2010 | Burdulis, Jr. et al. |
| 2010/0286700 A1 | 11/2010 | Snider et al. |
| 2010/0286789 A1 | 11/2010 | Meridew |
| 2010/0291401 A1 | 11/2010 | Medina et al. |
| 2010/0292743 A1 | 11/2010 | Singhal et al. |
| 2010/0298894 A1 | 11/2010 | Bojarski et al. |
| 2010/0305574 A1 | 12/2010 | Fitz et al. |
| 2010/0318088 A1 | 12/2010 | Warne et al. |
| 2010/0324692 A1 | 12/2010 | Uthgenannt et al. |
| 2011/0004317 A1 | 1/2011 | Hacking et al. |
| 2011/0008754 A1 | 1/2011 | Bassett et al. |
| 2011/0009869 A1 | 1/2011 | Marino et al. |
| 2011/0014081 A1 | 1/2011 | Jones et al. |
| 2011/0015636 A1 | 1/2011 | Katrana et al. |
| 2011/0015637 A1 | 1/2011 | De Smedt et al. |
| 2011/0015639 A1 | 1/2011 | Metzger et al. |
| 2011/0015752 A1 | 1/2011 | Meridew |
| 2011/0015753 A1 | 1/2011 | Meridew |
| 2011/0016690 A1 | 1/2011 | Narainasamy et al. |
| 2011/0022049 A1 | 1/2011 | Huebner et al. |
| 2011/0022174 A1 | 1/2011 | Holdstein et al. |
| 2011/0029088 A1 | 2/2011 | Rauscher et al. |
| 2011/0029091 A1 | 2/2011 | Bojarski et al. |
| 2011/0029093 A1 | 2/2011 | Bojarski |
| 2011/0029116 A1 | 2/2011 | Jordan et al. |
| 2011/0035012 A1 | 2/2011 | Linares |
| 2011/0040303 A1 | 2/2011 | Iannotti et al. |
| 2011/0040334 A1 | 2/2011 | Kaes et al. |
| 2011/0046735 A1 | 2/2011 | Metzger et al. |
| 2011/0054478 A1 | 3/2011 | Vanasse et al. |
| 2011/0060339 A1 | 3/2011 | De Wekker |
| 2011/0066193 A1 | 3/2011 | Lang et al. |
| 2011/0066245 A1 | 3/2011 | Lang et al. |
| 2011/0071528 A1 | 3/2011 | Carson |
| 2011/0071529 A1 | 3/2011 | Carson |
| 2011/0071530 A1 | 3/2011 | Carson |
| 2011/0071532 A1 | 3/2011 | Carson |
| 2011/0071533 A1 | 3/2011 | Metzger et al. |
| 2011/0071581 A1 | 3/2011 | Lang et al. |
| 2011/0071802 A1 | 3/2011 | Bojarski et al. |
| 2011/0087332 A1 | 4/2011 | Bojarski et al. |
| 2011/0092804 A1 | 4/2011 | Schoenefeld et al. |
| 2011/0093086 A1 | 4/2011 | Witt et al. |
| 2011/0106093 A1 | 5/2011 | Romano et al. |
| 2011/0106254 A1 | 5/2011 | Abel et al. |
| 2011/0125264 A1 | 5/2011 | Bagga et al. |
| 2011/0125284 A1 | 5/2011 | Gabbrielli et al. |
| 2011/0130795 A1 | 6/2011 | Ball |
| 2011/0151027 A1 | 6/2011 | Clineff et al. |
| 2011/0151259 A1 | 6/2011 | Jarman-smith et al. |
| 2011/0153025 A1 | 6/2011 | Mcminn |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0177590 A1 | 7/2011 | Clyne et al. |
| 2011/0184419 A1 | 7/2011 | Meridew et al. |
| 2011/0184424 A1 | 7/2011 | Isch et al. |
| 2011/0184526 A1 | 7/2011 | White et al. |
| 2011/0190899 A1 | 8/2011 | Pierce et al. |
| 2011/0190901 A1 | 8/2011 | Weissberg et al. |
| 2011/0213376 A1 | 9/2011 | Maxson et al. |
| 2011/0214279 A1 | 9/2011 | Park et al. |
| 2011/0218545 A1 | 9/2011 | Catanzarite et al. |
| 2011/0224674 A1 | 9/2011 | White et al. |
| 2011/0238071 A1 | 9/2011 | Fernandez-scoma |
| 2011/0245835 A1 | 10/2011 | Dodds et al. |
| 2011/0251617 A1 | 10/2011 | Ammann et al. |
| 2011/0257657 A1 | 10/2011 | Turner et al. |
| 2011/0269100 A1 | 11/2011 | Furrer et al. |
| 2011/0275032 A1 | 11/2011 | Tardieu et al. |
| 2011/0276053 A1 | 11/2011 | Birkbeck et al. |
| 2011/0276145 A1 | 11/2011 | Carignan et al. |
| 2011/0282473 A1 | 11/2011 | Pavlovskaia et al. |
| 2011/0295887 A1 | 12/2011 | Palmese et al. |
| 2011/0313424 A1 | 12/2011 | Bono et al. |
| 2011/0319745 A1 | 12/2011 | Frey |
| 2012/0010619 A1 | 1/2012 | Barsoum |
| 2012/0010710 A1 | 1/2012 | Frigg |
| 2012/0010711 A1 | 1/2012 | Antonyshyn et al. |
| 2012/0029345 A1 | 2/2012 | Mahfouz et al. |
| 2012/0029520 A1 | 2/2012 | Lang et al. |
| 2012/0041445 A1 | 2/2012 | Roose et al. |
| 2012/0041446 A1 | 2/2012 | Wong et al. |
| 2012/0041564 A1 | 2/2012 | Landon |
| 2012/0053590 A1 | 3/2012 | Allen et al. |
| 2012/0063655 A1 | 3/2012 | Dean et al. |
| 2012/0065640 A1 | 3/2012 | Metzger et al. |
| 2012/0078254 A1 | 3/2012 | Ashby et al. |

(56) References Cited

U.S. PATENT DOCUMENTS

| | | |
|---|---|---|
| 2012/0078258 A1 | 3/2012 | Lo et al. |
| 2012/0078259 A1 | 3/2012 | Meridew |
| 2012/0089595 A1 | 4/2012 | Jaecksch |
| 2012/0101586 A1 | 4/2012 | Carson |
| 2012/0109137 A1 | 5/2012 | Iannotti et al. |
| 2012/0109138 A1 | 5/2012 | Meridew et al. |
| 2012/0109226 A1 | 5/2012 | Iannotti et al. |
| 2012/0116203 A1 | 5/2012 | Vancraen et al. |
| 2012/0123422 A1 | 5/2012 | Agnihotri et al. |
| 2012/0123423 A1 | 5/2012 | Fryman |
| 2012/0130382 A1 | 5/2012 | Iannotti et al. |
| 2012/0136365 A1 | 5/2012 | Iannotti et al. |
| 2012/0141034 A1 | 6/2012 | Iannotti et al. |
| 2012/0143197 A1 | 6/2012 | Lang et al. |
| 2012/0143267 A1 | 6/2012 | Iannotti et al. |
| 2012/0150242 A1 | 6/2012 | Mannion |
| 2012/0158002 A1 | 6/2012 | Carignan et al. |
| 2012/0165954 A1 | 6/2012 | Nimal |
| 2012/0190971 A1 | 7/2012 | De Wekker |
| 2012/0192401 A1 | 8/2012 | Pavlovskaia et al. |
| 2012/0196314 A1 | 8/2012 | Nawaz et al. |
| 2012/0209276 A1 | 8/2012 | Schuster |
| 2012/0215225 A1 | 8/2012 | Philippon et al. |
| 2012/0215310 A1 | 8/2012 | Sharp et al. |
| 2012/0221017 A1 | 8/2012 | Bonutti |
| 2012/0226283 A1 | 9/2012 | Meridew et al. |
| 2012/0232596 A1 | 9/2012 | Ribeiro |
| 2012/0245587 A1 | 9/2012 | Fang et al. |
| 2012/0245647 A1 | 9/2012 | Kunz et al. |
| 2012/0259335 A1 | 10/2012 | Scifert et al. |
| 2012/0265208 A1 | 10/2012 | Smith |
| 2012/0271131 A1 | 10/2012 | Kling et al. |
| 2012/0271314 A1 | 10/2012 | Stemniski et al. |
| 2012/0271366 A1 | 10/2012 | Katrana et al. |
| 2012/0276509 A1 | 11/2012 | Iannotti et al. |
| 2012/0277751 A1 | 11/2012 | Catanzarite et al. |
| 2012/0289965 A1 | 11/2012 | Gelaude et al. |
| 2012/0296339 A1 | 11/2012 | Iannotti et al. |
| 2012/0303004 A1 | 11/2012 | Uthgenannt et al. |
| 2012/0303033 A1 | 11/2012 | Weiner et al. |
| 2012/0310364 A1 | 12/2012 | Li et al. |
| 2012/0310399 A1 | 12/2012 | Metzger |
| 2012/0316564 A1 | 12/2012 | Serbousek et al. |
| 2012/0323246 A1 | 12/2012 | Catanzarite et al. |
| 2012/0323282 A1 | 12/2012 | Brianza et al. |
| 2012/0323323 A1 | 12/2012 | Vargas et al. |
| 2012/0330319 A1 | 12/2012 | Birkbeck et al. |
| 2013/0001121 A1 | 1/2013 | Metzger |
| 2013/0006250 A1 | 1/2013 | Metzger et al. |
| 2013/0018483 A1 | 1/2013 | Li et al. |
| 2013/0035766 A1 | 2/2013 | Meridew |
| 2013/0046310 A1 | 2/2013 | Ranawat et al. |
| 2013/0053854 A1 | 2/2013 | Schoenefeld et al. |
| 2013/0056912 A1 | 3/2013 | O'neill et al. |
| 2013/0060253 A1 | 3/2013 | Couture et al. |
| 2013/0066323 A1 | 3/2013 | Nycz et al. |
| 2013/0072940 A1 | 3/2013 | Dawood et al. |
| 2013/0085500 A1 | 4/2013 | Meridew et al. |
| 2013/0085590 A1 | 4/2013 | Bryan et al. |
| 2013/0110116 A1 | 5/2013 | Kehres et al. |
| 2013/0110470 A1 | 5/2013 | Vanasse et al. |
| 2013/0116699 A1 | 5/2013 | Smith et al. |
| 2013/0119579 A1 | 5/2013 | Iannotti et al. |
| 2013/0123850 A1 | 5/2013 | Schoenefeld et al. |
| 2013/0131681 A1 | 5/2013 | Katrana et al. |
| 2013/0144392 A1 | 6/2013 | Hughes |
| 2013/0158671 A1 | 6/2013 | Uthgenannt et al. |
| 2013/0197528 A1 | 8/2013 | Zakaria et al. |
| 2013/0197529 A1 | 8/2013 | Metzger |
| 2013/0197687 A1 | 8/2013 | Pavlovskaia et al. |
| 2013/0218163 A1 | 8/2013 | Frey |
| 2013/0245631 A1 | 9/2013 | Bettenga |
| 2013/0245801 A1 | 9/2013 | Schroeder |
| 2013/0261503 A1 | 10/2013 | Sherman |
| 2013/0264749 A1 | 10/2013 | Jones et al. |
| 2013/0268085 A1 | 10/2013 | Dong |
| 2013/0289730 A1 | 10/2013 | Gabriel et al. |
| 2013/0292870 A1 | 11/2013 | Roger |
| 2013/0317511 A1 | 11/2013 | Bojarski et al. |
| 2013/0317621 A1 | 11/2013 | Metzger et al. |
| 2013/0326878 A1 | 12/2013 | Boehm et al. |
| 2013/0338673 A1 | 12/2013 | Keppler |
| 2014/0001226 A1 | 1/2014 | Scabin et al. |
| 2014/0005672 A1 | 1/2014 | Edwards et al. |
| 2014/0012266 A1 | 1/2014 | Bonin, Jr. et al. |
| 2014/0018934 A1 | 1/2014 | Meridew et al. |
| 2014/0052270 A1 | 2/2014 | Witt et al. |
| 2014/0066937 A1 | 3/2014 | Wiebe, III et al. |
| 2014/0081659 A1 | 3/2014 | Nawana et al. |
| 2014/0088724 A1 | 3/2014 | Meridew |
| 2014/0094816 A1 | 4/2014 | White et al. |
| 2014/0100578 A1 | 4/2014 | Metzger et al. |
| 2014/0107651 A1 | 4/2014 | Meridew et al. |
| 2014/0107654 A1 | 4/2014 | Kehres et al. |
| 2014/0107715 A1 | 4/2014 | Heilman et al. |
| 2014/0081275 A1 | 5/2014 | Metzger et al. |
| 2014/0127211 A1 | 5/2014 | Geles et al. |
| 2014/0135775 A1 | 5/2014 | Maxson |
| 2014/0163564 A1 | 6/2014 | Bollinger |
| 2014/0163565 A1 | 6/2014 | Bollinger |
| 2014/0172116 A1 | 6/2014 | Maxson et al. |
| 2014/0188119 A1 | 7/2014 | Catanzarite et al. |
| 2014/0222157 A1 | 8/2014 | Al Hares et al. |
| 2014/0243833 A1 | 8/2014 | Smith |
| 2014/0257304 A1 | 9/2014 | Eash |
| 2014/0257508 A1 | 9/2014 | Bojarski et al. |
| 2014/0276854 A1 | 9/2014 | Schoenefeld et al. |
| 2014/0276856 A1 | 9/2014 | Schoenefeld |
| 2014/0276870 A1 | 9/2014 | Eash |
| 2014/0276873 A1 | 9/2014 | Meridew et al. |
| 2014/0303938 A1 | 10/2014 | Schoenefeld et al. |
| 2014/0303990 A1 | 10/2014 | Schoenefeld et al. |
| 2014/0309644 A1 | 10/2014 | Metzger et al. |
| 2014/0324058 A1 | 10/2014 | Metzger et al. |
| 2014/0378979 A1 | 12/2014 | Stone et al. |
| 2015/0088293 A1 | 3/2015 | Metzger |
| 2015/0112348 A1 | 4/2015 | Schoenefeld et al. |
| 2015/0112349 A1 | 4/2015 | Schoenefeld |
| 2015/0150688 A1 | 6/2015 | Vanasse et al. |
| 2015/0157341 A1 | 6/2015 | Catanzarite et al. |
| 2015/0320429 A1 | 11/2015 | Katrana et al. |
| 2015/0320508 A1 | 11/2015 | White et al. |
| 2015/0335438 A1 | 11/2015 | Pierce et al. |
| 2015/0351778 A1 | 12/2015 | Uthgenannt et al. |
| 2016/0008013 A1 | 1/2016 | Metzger et al. |
| 2016/0038160 A1 | 2/2016 | Metzger et al. |
| 2016/0100845 A1 | 4/2016 | Smith et al. |
| 2016/0128706 A1 | 5/2016 | Meridew |
| 2016/0135824 A1 | 5/2016 | Vanasse et al. |
| 2016/0196651 A1 | 7/2016 | Dean et al. |
| 2016/0203241 A1 | 7/2016 | Dean et al. |
| 2016/0213491 A1 | 7/2016 | Schoenefeld et al. |
| 2016/0228133 A1 | 8/2016 | Meridew et al. |
| 2016/0338838 A1 | 11/2016 | Meridew et al. |
| 2017/0000626 A1 | 1/2017 | White et al. |
| 2017/0056030 A1 | 3/2017 | Metzger et al. |

FOREIGN PATENT DOCUMENTS

| | | |
|---|---|---|
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2588907 A1 | 6/2006 |
| CA | 2590534 A1 | 6/2006 |
| CH | 117960 A | 5/1927 |
| CN | 1630495 A | 6/2005 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| CN | 102038553 A | 5/2011 |

(56) References Cited

FOREIGN PATENT DOCUMENTS

| | | |
|---|---|---|
| CN | 102335742 A | 2/2012 |
| DE | 337437 C | 5/1921 |
| DE | 3447365 A1 | 7/1986 |
| DE | 04219939 A1 | 12/1993 |
| DE | 4421153 A1 | 12/1995 |
| DE | 10341187 A1 | 3/2005 |
| DE | 102009028503 A1 | 2/2011 |
| DE | 102011082902 A1 | 3/2012 |
| DE | 102012205820 A1 | 10/2012 |
| DE | 112010003901 T5 | 11/2012 |
| EP | 0114505 A1 | 8/1984 |
| EP | 0255797 A1 | 2/1988 |
| EP | 0326768 A2 | 8/1989 |
| EP | 0579868 A2 | 1/1994 |
| EP | 0591985 A1 | 4/1994 |
| EP | 0645984 A1 | 4/1995 |
| EP | 0650706 A1 | 5/1995 |
| EP | 0916324 A2 | 5/1999 |
| EP | 1321107 A1 | 6/2003 |
| EP | 1327424 A1 | 7/2003 |
| EP | 1437102 A1 | 7/2004 |
| EP | 01486900 A1 | 12/2004 |
| EP | 1563810 A1 | 8/2005 |
| EP | 1588669 A1 | 10/2005 |
| EP | 1634551 A2 | 3/2006 |
| EP | 1832239 A1 | 9/2007 |
| EP | 1852072 A2 | 11/2007 |
| EP | 1852072 A3 | 11/2007 |
| EP | 2029061 A2 | 3/2009 |
| EP | 2168507 A2 | 3/2010 |
| EP | 2303146 A1 | 4/2011 |
| EP | 2303192 A1 | 4/2011 |
| EP | 2352445 A1 | 8/2011 |
| EP | 2396741 A1 | 12/2011 |
| EP | 2398381 A1 | 12/2011 |
| EP | 2403437 A2 | 1/2012 |
| EP | 2491873 A2 | 8/2012 |
| EP | 2502582 A1 | 9/2012 |
| EP | 2709568 A1 | 3/2014 |
| EP | 2816962 A1 | 12/2014 |
| EP | 2029061 B1 | 2/2017 |
| FR | 1111677 A | 3/1956 |
| FR | 2429582 A1 | 1/1980 |
| FR | 2659226 A2 | 9/1991 |
| FR | 2721195 A1 | 12/1995 |
| FR | 2768916 A1 | 4/1999 |
| FR | 2979817 A1 | 3/2013 |
| GB | 2094590 A | 9/1982 |
| GB | 2197790 A1 | 6/1988 |
| GB | 2423021 A | 8/2006 |
| GB | 2442441 A | 4/2008 |
| GB | 2447702 A | 9/2008 |
| GB | 2483980 A | 3/2012 |
| GB | 2486390 A | 6/2012 |
| GB | 2490220 A | 10/2012 |
| GB | 2491526 A | 12/2012 |
| GB | 2486390 B | 11/2015 |
| GB | 2527690 B | 6/2016 |
| GB | 2483980 B | 12/2016 |
| GB | 2491526 B | 1/2017 |
| JP | 59157715 A | 9/1984 |
| JP | 60231208 A | 11/1985 |
| JP | 6233790 A | 8/1994 |
| JP | 2000245758 A | 9/2000 |
| JP | 2004008797 A | 1/2004 |
| JP | 2005218861 A | 8/2005 |
| JP | 2009514612 A | 4/2009 |
| JP | 2009515610 A | 4/2009 |
| JP | 2011505080 A | 2/2011 |
| JP | 2011517996 A | 6/2011 |
| JP | 2011527885 A | 11/2011 |
| JP | 5710014 B2 | 4/2015 |
| KR | 20050072500 A | 7/2005 |
| KR | 20050084024 A | 8/2005 |
| RU | 2083179 C1 | 7/1997 |
| RU | 2113182 C1 | 6/1998 |
| RU | 2125835 C1 | 2/1999 |
| RU | 2138223 C1 | 9/1999 |
| RU | 2175534 C2 | 11/2001 |
| RU | 2187975 C1 | 8/2002 |
| RU | 2218242 C2 | 12/2003 |
| TW | 231755 A | 5/2005 |
| TW | 201114409 A | 5/2011 |
| WO | WO-8807840 A1 | 10/1988 |
| WO | WO-8909028 A1 | 10/1989 |
| WO | WO-9014806 A1 | 12/1990 |
| WO | WO-9107139 A1 | 5/1991 |
| WO | WO-9325157 A1 | 12/1993 |
| WO | WO-9413218 A1 | 6/1994 |
| WO | WO-9528688 A1 | 10/1995 |
| WO | WO-9607361 A1 | 3/1996 |
| WO | WO-9729703 A1 | 8/1997 |
| WO | WO-9901073 A1 | 1/1999 |
| WO | WO-9952473 A1 | 10/1999 |
| WO | WO-9959106 A1 | 11/1999 |
| WO | WO-0110339 A2 | 2/2001 |
| WO | WO-0133511 A2 | 5/2001 |
| WO | WO-0170142 A1 | 9/2001 |
| WO | WO-0184479 A1 | 11/2001 |
| WO | WO-0217821 A2 | 3/2002 |
| WO | WO-2002026145 A1 | 4/2002 |
| WO | WO-0236024 A1 | 5/2002 |
| WO | WO-02096268 A2 | 12/2002 |
| WO | WO-03051210 A2 | 6/2003 |
| WO | WO-03051211A1 | 6/2003 |
| WO | WO-2004030556 A2 | 4/2004 |
| WO | WO-2004032806 A1 | 4/2004 |
| WO | WO-2004049981 A2 | 6/2004 |
| WO | WO-2004051301 A2 | 6/2004 |
| WO | WO-2004078069 A2 | 9/2004 |
| WO | WO-2004112610 A2 | 12/2004 |
| WO | WO-2005051209 A1 | 6/2005 |
| WO | WO-2005051233 A2 | 6/2005 |
| WO | WO-2005051239 A1 | 6/2005 |
| WO | WO-2005051240 A1 | 6/2005 |
| WO | WO-2005077039 A2 | 8/2005 |
| WO | WO-2005099636 A1 | 10/2005 |
| WO | WO-06060795 A1 | 6/2006 |
| WO | WO-2006058057 A2 | 6/2006 |
| WO | WO-2006092600 A1 | 9/2006 |
| WO | WO-2006127486 A2 | 11/2006 |
| WO | WO-2006134345 A1 | 12/2006 |
| WO | WO-2006136955 A1 | 12/2006 |
| WO | WO-07041375 A2 | 4/2007 |
| WO | WO-2007053572 A2 | 5/2007 |
| WO | WO-2007062079 A2 | 5/2007 |
| WO | WO-2007092841 A2 | 8/2007 |
| WO | WO-2007137327 A1 | 12/2007 |
| WO | WO-2007145937 A2 | 12/2007 |
| WO | WO-2007145937 A3 | 12/2007 |
| WO | WO-2007147235 A1 | 12/2007 |
| WO | WO-2008014618 A1 | 2/2008 |
| WO | WO-2008021494 A2 | 2/2008 |
| WO | WO-2008040961 A1 | 4/2008 |
| WO | WO-2008044055 A1 | 4/2008 |
| WO | WO-2008091358 A1 | 7/2008 |
| WO | WO-2008101090 A2 | 8/2008 |
| WO | WO-2008109751 A1 | 9/2008 |
| WO | WO-2008112996 A1 | 9/2008 |
| WO | WO-2008140748 A1 | 11/2008 |
| WO | WO-2009001083 A1 | 12/2008 |
| WO | WO-2009001109 A1 | 12/2008 |
| WO | WO-2009025783 A1 | 2/2009 |
| WO | WO-2009073781 A2 | 6/2009 |
| WO | WO-2009129063 A1 | 10/2009 |
| WO | WO-2009129067 A1 | 10/2009 |
| WO | WO-2010033431 A1 | 3/2010 |
| WO | WO-2010045537 A1 | 4/2010 |
| WO | WO-2010048257 A1 | 4/2010 |
| WO | WO-2010088696 A1 | 8/2010 |
| WO | WO-2010093902 A1 | 8/2010 |
| WO | WO-2010096553 A1 | 8/2010 |
| WO | WO-2010096557 A2 | 8/2010 |
| WO | WO-2010124164 A1 | 10/2010 |

(56) References Cited

FOREIGN PATENT DOCUMENTS

| | | |
|---|---|---|
| WO | WO-2010129870 A1 | 11/2010 |
| WO | WO-2010144705 A1 | 12/2010 |
| WO | WO-2010148103 A1 | 12/2010 |
| WO | WO-2010150223 A1 | 12/2010 |
| WO | WO-2011018458 A1 | 2/2011 |
| WO | WO-2011019797 A3 | 2/2011 |
| WO | WO-2011041398 A1 | 4/2011 |
| WO | WO-2011060536 A1 | 5/2011 |
| WO | WO-2011063231 A1 | 5/2011 |
| WO | WO-2011080260 A1 | 7/2011 |
| WO | WO-2011106711 A1 | 9/2011 |
| WO | WO-2011109260 A1 | 9/2011 |
| WO | WO-2011110374 A1 | 9/2011 |
| WO | WO-2011117644 A2 | 9/2011 |
| WO | WO-2012006444 A2 | 1/2012 |
| WO | WO-2012033821 A1 | 3/2012 |
| WO | WO-2012058344 A1 | 5/2012 |
| WO | WO-2012058349 A4 | 5/2012 |
| WO | WO-2012058353 A4 | 5/2012 |
| WO | WO-2012058355 A4 | 5/2012 |
| WO | WO-2012061042 A1 | 5/2012 |
| WO | WO-2012116206 A1 | 8/2012 |
| WO | WO-2012141790 A1 | 10/2012 |
| WO | WO-2012158917 A1 | 11/2012 |
| WO | WO-2012173929 A1 | 12/2012 |
| WO | WO-2012174008 A1 | 12/2012 |
| WO | WO-2013126416 A1 | 8/2013 |
| WO | WO-2013170872 A1 | 11/2013 |
| WO | WO-2014019712 A1 | 2/2014 |
| WO | WO-2015084831 A1 | 6/2015 |
| WO | WO-2016007631 A1 | 1/2016 |

OTHER PUBLICATIONS

U.S. Appl. No. 12/103,824, filed Apr. 16, 2008, Method and Apparatus for Manufacturing an Implant.

U.S. Appl. No. 14/658,429, filed Mar. 16, 2015, Patient-Modified Implant.

U.S. Appl. No. 15/130,414, filed Apr. 15, 2016, Patient-Specific Acetabular Guides and Associated Instruments.

U.S. Appl. No. 13/047,924, filed Mar. 15, 2011, Patient-Specific Augments.

U.S. Appl. No. 13/045,169, filed Mar. 10, 2011, Instrument With Transparent Portion for Use With Patient-Specific Alignment Guide.

U.S. Appl. No. 14/483,214, filed Sep. 11, 2014, Alignment Guides With Patient-Specific Anchoring Elements.

U.S. Appl. No. 14/812,583, filed Jul. 29, 2015, Patient-Specific Augments.

U.S. Appl. No. 13/766,419, filed Feb. 13, 2013, Method and Apparatus for Manufacturing an Implant.

U.S. Appl. No. 14/739,160, filed Jun. 15, 2015, Method and Apparatus for Manufacturing an Implant.

U.S. Appl. No. 12/371,096, filed Feb. 13, 2009, Method and Apparatus for Manufacturing an Implant.

U.S. Appl. No. 14/865,762, filed Sep. 25, 2015, Patient Specific Alignment Guide With Cutting Surface and Laser Indicator.

U.S. Appl. No. 14/798,809, filed Jul. 14, 2015, Femoral Acetabular Impingement Guide.

U.S. Appl. No. 15/008,528, filed Jan. 28, 2016, Patient-Specific Shoulder Guide.

U.S. Appl. No. 12/938,905, filed Nov. 3, 2010, Patient-Specific Implants.

U.S. Appl. No. 15/093,384, filed Apr. 7, 2016, Patient-Specific Pre-Operative Planning.

U.S. Appl. No. 12/255,945, filed Oct. 22, 2008, Mechanical Axis Alignment Using MRI Imaging.

U.S. Appl. No. 15/495,432, filed Apr. 24, 2017, Patient-Specific Hip Joint Devices.

U.S. Appl. No. 15/224,741, filed Aug. 1, 2016, Patient-Specific Tools and Implants.

U.S. Appl. No. 15/267,714, filed Sep. 16, 2016, Patient-Specific Acetabular Alignment Guides.

U.S. Appl. No. 13/527,981, filed Jun. 20, 2012, Backup Surgical Instrument System and Method.

U.S. Appl. No. 14/327,234, filed Jul. 9, 2014, Patient-Specific Knee Alignment Guide and Associated Method.

U.S. Appl. No. 14/973,057, filed Dec. 17, 2015, Patient-Specific Femoral Version Guide.

U.S. Appl. No. 15/352,721, filed Nov. 16, 2016, Patient-Specific Orthopedic Instruments.

"3D-Implantatplanung und StereolithographieImplantatbohrschablonen", Stomatologie 101.3, (2004), 55-59.

"AGC 3000 Intramedullary",—Surgical Technique Using PMMA Fixation—Biomet, Inc., (1987), 32 pgs.

"AGC Distal Fern Cutter for Dr. Hardy", Biomet, Inc., (Jun. 22, 1989), 4 pgs.

"AGC Total Knee System, Intramedullary Without Distractor Surgical Technique", Biomet, Inc., (1989), 35 pgs.

"AGC Total Knee System, Unicondylar Surgical Overview", Biomet, Inc., (Jan. 31, 1989), 5 pgs.

"AGC Traditional Surgical Overview", Biomet Orthopedics, Inc., (2001), 8 pgs.

"AGC-S Total Knee System, Surgical Technique for the AGC-S Total Knee System", Biomet, Inc., (1992), 22 pgs.

"Amazing Precision. Beautiful Results. The next evolution of MAKOplasty® is here", MAKO Surgical Corp., (Feb. 2009), 6 pgs.

"Anatomic Axial Alignment Instrumentation", Biomet, Inc., (1994), 24 pgs.

"U.S. Appl. No. 09/861,859, 312 Amendment filed Sep. 27, 2011", 3 pgs.

"U.S. Appl. No. 09/861,859, Final Office Action dated Aug. 5, 2011", 10 pgs.

"U.S. Appl. No. 09/861,859, Non Final Office Action dated Mar. 3, 2011", 9 pgs.

"U.S. Appl. No. 09/861,859, Notice of Allowance dated Sep. 8, 2011", 5 pgs.

"U.S. Appl. No. 09/861,859, Notice of Non Compliant Amendment dated Nov. 18, 2010", 3 pgs.

"U.S. Appl. No. 09/861,859, PTO Response to Rule 312 Communication dated Oct. 7, 2011", 2 pgs.

"U.S. Appl. No. 09/861,859, Response filed May 12, 2011 to Non Final Office Action dated Mar. 3, 2011", 13 pgs.

"U.S. Appl. No. 09/861,859, Response filed Aug. 22, 2011 to Final Office Action dated Aug. 5, 2011", 9 pgs.

"U.S. Appl. No. 09/861,859, Response filed Oct. 28, 2010 to Restriction Requirement dated Sep. 29, 2010", 1 pg.

"U.S. Appl. No. 09/861,859, Response filed Nov. 29, 2010 to Notice of Non Compliant Amendment dated Nov. 18, 2010", 8 pgs.

"U.S. Appl. No. 09/861,859, Restriction Requirement dated Sep. 29, 2010", 7 pgs.

"U.S. Appl. No. 11/363,548, Advisory Action dated Aug. 5, 2009", 2 pgs.

"U.S. Appl. No. 11/363,548, Appeal Brief filed Jun. 19, 2009", 52 pgs.

"U.S. Appl. No. 11/363,548, Final Office Action dated Jan. 22, 2009", 12 pgs.

"U.S. Appl. No. 11/363,548, Non Final Office Action dated Jul. 9, 2008", 11 pgs.

"U.S. Appl. No. 11/363,548, Notice of Allowance dated Apr. 9, 2010", 5 pgs.

"U.S. Appl. No. 11/363,548, Response filed Jun. 19, 2009 to Final Office Action dated Jan. 22, 2009", 9 pgs.

"U.S. Appl. No. 11/363,548, Response filed Oct. 8, 2008 to Non Final Office Action dated Jul. 9, 2008", 18 pgs.

"U.S. Appl. No. 11/971,390, Non Final Office Action dated Mar. 3, 2011", 7 pgs.

"U.S. Appl. No. 11/971,390, Notice of Allowance dated Jul. 26, 2011", 8 pgs.

"U.S. Appl. No. 11/971,390, Preliminary Amendment filed Jan. 14, 2011", 8 pgs.

"U.S. Appl. No. 11/971,390, Response filed May 12, 2011 to Non Final Office Action dated Mar. 3, 2011", 12 pgs.

(56) References Cited

OTHER PUBLICATIONS

"U.S. Appl. No. 11/971,390, Response filed Dec. 23, 2010 to Restriction Requirement dated Nov. 23, 2010", 1 pgs.
"U.S. Appl. No. 11/971,390, Restriction Requirement dated Nov. 23, 2010", 6 pgs.
"U.S. Appl. No. 12/039,849, Final Office Action dated Apr. 8, 2012", 7 pgs.
"U.S. Appl. No. 12/039,849, Non Final Office Action dated Mar. 8, 2012", 11 pgs.
"U.S. Appl. No. 12/039,849, Notice of Allowance dated Jun. 6, 2012", 7 pgs.
"U.S. Appl. No. 12/039,849, Response filed Apr. 3, 2012 to Non Final Office Action dated Mar. 8, 2012", 19 pgs.
"U.S. Appl. No. 12/039,849, Response filed May 14, 2012 to Final Office Action dated Apr. 8, 2012", 7 pgs.
"U.S. Appl. No. 12/039,849, Response filed Aug. 30, 2011 to Restriction Requirement dated Aug. 16, 2011", 11 pgs.
"U.S. Appl. No. 12/039,849, Restriction Requirement dated Aug. 16, 2011", 6 pgs.
"U.S. Appl. No. 12/103,824, Examiner Interview Summary dated Jan. 12, 2012", 2 pgs.
"U.S. Appl. No. 12/103,824, Examiner Interview Summary dated Sep. 19, 2011", 3 pgs.
"U.S. Appl. No. 12/103,824, Final Office Action dated Apr. 26, 2012", 19 pgs.
"U.S. Appl. No. 12/103,824, Final Office Action dated Dec. 6, 2011", 20 pgs.
"U.S. Appl. No. 12/103,824, Non Final Office Action dated Aug. 17, 2011", 17 pgs.
"U.S. Appl. No. 12/103,824, Response filed Sep. 15, 2011 to Non Final Office Action dated Aug. 17, 2011", 16 pgs.
"U.S. Appl. No. 12/103,834, Final Office Action dated Dec. 8, 2010", 11 pgs.
"U.S. Appl. No. 12/103,834, Non Final Office Action dated Jun. 22, 2010", 9 pgs.
"U.S. Appl. No. 12/103,834, Response filed Feb. 3, 2011 to Final Office Action dated Dec. 8, 2010", 5 pgs.
"U.S. Appl. No. 12/103,834, Response filed Sep. 21, 2010 to Non Final Office Action dated Jun. 22, 2010", 11 pgs.
"U.S. Appl. No. 12/103,834, Notice of Allowance dated Feb. 23, 2011", 9 ogs.
"U.S. Appl. No. 12/103,834, Response filed Mar. 18, 2010 to Restriction Requirement dated Feb. 18, 2010", 9 pgs.
"U.S. Appl. No. 12/103,834, Restriction Requirement dated Feb. 18, 2010", 9 pgs.
"U.S. Appl. No. 12/211,407, Examiner Interview Summary dated Jan. 13, 2012", 3 pgs.
"U.S. Appl. No. 12/211,407, Examiner Interview Summary dated Dec. 5, 2013", 3 pgs.
"U.S. Appl. No. 12/211,407, Final Office Action dated Nov. 25, 2011", 14 pgs.
"U.S. Appl. No. 12/211,407, Non Final Office Action dated Aug. 17, 2011", 15 pgs.
"U.S. Appl. No. 12/211,407, Notice of Allowance dated Aug. 7, 2013", 12 pgs.
"U.S. Appl. No. 12/211,407, Response filed Jan. 16, 2012 to Final Office Action dated Nov. 25, 2011", 18 pgs.
"U.S. Appl. No. 12/211,407, Response filed Aug. 29, 2011 to Non Final Office Action dated Aug. 17, 2011", 19 pgs.
"U.S. Appl. No. 12/255,945, Advisory Action dated Feb. 5, 2014", 3 pgs.
"U.S. Appl. No. 12/255,945, Advisory Action dated Feb. 10, 2012", 3 pgs.
"U.S. Appl. No. 12/255,945, Advisory Action dated Mar. 27, 2014", 3 pgs.
"U.S. Appl. No. 12/255,945, Appeal Brief filed Mar. 26, 2014", 29 pgs.
"U.S. Appl. No. 12/255,945, Appeal Brief filed Oct. 13, 2014", 30 pgs.

"U.S. Appl. No. 12/255,945, Examiner Interview Summary dated Aug. 13, 2013", 3 pgs.
"U.S. Appl. No. 12/255,945, Examiner Interview Summary dated Sep. 22, 2011", 3 pgs.
"U.S. Appl. No. 12/255,945, Examiner's Answer dated Feb. 12, 2015", 26 pgs.
"U.S. Appl. No. 12/255,945, Final Office Action dated Sep. 30, 2013", 21 pgs.
"U.S. Appl. No. 12/255,945, Final Office Action dated Nov. 28, 2011", 14 pgs.
"U.S. Appl. No. 12/255,945, Non Final Office Action dated May 7, 2013", 23 pgs.
"U.S. Appl. No. 12/255,945, Non Final Office Action dated Jul. 24, 2014", 26 pgs.
"U.S. Appl. No. 12/255,945, Non Final Office Action dated Aug. 4, 2011", 12 pgs.
"U.S. Appl. No. 12/255,945, Reply Brief filed Apr. 13, 2015", 4 pgs.
"U.S. Appl. No. 12/255,945, Response filed Jan. 17, 2012 to Final Office Action dated Nov. 28, 2011", 11 pgs.
"U.S. Appl. No. 12/255,945, Response filed Jan. 28, 2014 to Final Office Action dated Sep. 30, 2013", 13 pgs.
"U.S. Appl. No. 12/255,945, Response filed Feb. 28, 2012 to Advisory Action dated Feb. 10, 2012", 13 pgs.
"U.S. Appl. No. 12/255,945, Response filed Jul. 17, 2011 to Restriction Requirement dated Jun. 7, 2011", 8 pgs.
"U.S. Appl. No. 12/255,945 Response filed Aug. 8, 2013 to Non Final Office Action dated May 7, 2013", 13 pgs.
"U.S. Appl. No. 12/255,945 Response filed Nov. 4, 2011 to Non Final Office Action dated Aug. 4, 2011", 14 pgs.
"U.S. Appl. No. 12/255,945 Restriction Requirement dated Jun. 7, 2011", 8 pgs.
"U.S. Appl. No. 12/255,945 Supplemental Amendment filed Mar. 5, 2014", 13 pgs.
"U.S. Appl. No. 12/371,096 Examiner Interview Summary dated Jan. 13, 2012", 3 pgs.
"U.S. Appl. No. 12/371,096 Examiner Interview Summary dated Dec. 5, 2013", 3 pgs.
"U.S. Appl. No. 12/371,096 Final Office Action dated Jul. 6, 2011", 23 pgs.
"U.S. Appl. No. 12/371,096 Final Office Action dated Nov. 25, 2011", 14 pgs.
"U.S. Appl. No. 12/371,096 Non Final Office Action dated Mar. 30, 2011", 19 pgs.
"U.S. Appl. No. 12/371,096, Non Final Office Action dated Apr. 17, 2014", 23 pgs.
"U.S. Appl. No. 12/371,096, Non Final Office Action dated Aug. 17, 2011", 15 pgs.
"U.S. Appl. No. 12/371,096, Non Final Office Action dated Aug. 28, 2014", 21 pgs.
"U.S. Appl. No. 12/371,096, Notice of Allowance dated Aug. 7, 2013", 12 pgs.
"U.S. Appl. No. 12/371,096, Notice of Allowance dated Nov. 5, 2013", 2 pgs.
"U.S. Appl. No. 12/371,096, Notice of Allowance dated Nov. 15, 2013", 2 pgs.
"U.S. Appl. No. 12/371,096, Response filed Jan. 16, 2012 to Final Office Action dated Nov. 25, 2011", 15 pgs.
"U.S. Appl. No. 12/371,096, Response filed Aug. 29, 2011 to Non Final Office Action dated Aug. 17, 2011", 19 pgs.
"U.S. Appl. No. 12/389,901, Applicant's Summary of Examiner Interview filed Nov. 28, 2011", 1 pg.
"U.S. Appl. No. 12/389,901, Examiner Interview Summary dated Nov. 1, 2011", 3 pgs.
"U.S. Appl. No. 12/389,901, Non Final Office Action dated May 12, 2011", 6 pgs.
"U.S. Appl. No. 12/389,901, Notice of Allowance dated Sep. 30, 2011", 12 pgs.
"U.S. Appl. No. 12/389,901, Notice of Allowance dated Dec. 7, 2011", 9 pgs.
"U.S. Appl. No. 12/389,901, Response filed Mar. 17, 2011 to Restriction Requirement dated Mar. 2, 2011", 8 pgs.
"U.S. Appl. No. 12/389,901, Response filed Jun. 28, 2011 to Non Final Office Action dated May 12, 2011", 11 pgs.

(56) References Cited

OTHER PUBLICATIONS

"U.S. Appl. No. 12/389,901, Restriction Requirement dated Mar. 2, 2011", 6 pgs.
"U.S. Appl. No. 12/483,807, Advisory Action dated Jan. 3, 2012", 2 pgs.
"U.S. Appl. No. 12/483,807, Applicant's Summary of Examiner Interview filed Jan. 19, 2012", 3 pgs.
"U.S. Appl. No. 12/483,807, Applicant's Summary of Examiner Interview filed Dec. 21, 2011", 3 pgs.
"U.S. Appl. No. 12/483,807, Non Final Office Action dated Oct. 3, 2011", 18 pgs.
"U.S. Appl. No. 12/483,807, Notice of Allowance dated Feb. 21, 2013", 9 pgs.
"U.S. Appl. No. 12/483,807, Response filed Jan. 16, 2012 to Advisory Action dated Jan. 3, 2012", 14 pgs.
"U.S. Appl. No. 12/483,807, Response filed Oct. 24, 2011 to Non Final Office Action dated Oct. 3, 2011", 16 pgs.
"U.S. Appl. No. 12/483,807, Response filed Dec. 19, 2011 to Final Office Action dated Nov. 4, 2011", 7 pgs.
"U.S. Appl. No. 12/486,992, Examiner Interview Summary dated Jan. 9, 2012", 3 pgs.
"U.S. Appl. No. 12/486,992, Examiner Interview Summary dated Mar. 9, 2012", 4 pgs.
"U.S. Appl. No. 12/486,992, Final Office Action dated Feb. 21, 2012", 8 pgs.
"U.S. Appl. No. 12/486,992, Non Final Office Action dated Nov. 21, 2011", 9 pgs.
"U.S. Appl. No. 12/486,992, Notice of Allowance dated Jun. 12, 2014", 11 pgs.
"U.S. Appl. No. 12/486,992, Preliminary Amendment filed Mar. 9, 2010", 3 pgs.
"U.S. Appl. No. 12/486,992, Response filed Jan. 17, 2012 to Non Final Office Action dated Nov. 21, 2011", 13 pgs.
"U.S. Appl. No. 12/486,992, Response filed Mar. 12, 2012 to Final Office Action dated Feb. 21, 2012", 10 pgs.
"U.S. Appl. No. 12/486,992, Response filed Oct. 24, 2011 to Restriction Requirement dated Sep. 30, 2011", 7 pgs.
"U.S. Appl. No. 12/486,992, Restriction Requirement dated Sep. 30, 2011", 6 pgs.
"U.S. Appl. No. 12/571,969, Advisory Action dated Oct. 21, 2013", 3 pgs.
"U.S. Appl. No. 12/571,969, Examiner Interview Summary dated Feb. 26, 2015", 3 pgs.
"U.S. Appl. No. 12/571,969, Examiner Interview Summary dated Mar. 11, 2013", 3 pgs.
"U.S. Appl. No. 12/571,969, Final Office Action dated Jan. 15, 2015", 9 pgs.
"U.S. Appl. No. 12/571,969, Final Office Action dated Jul. 31, 2013", 8 pgs.
"U.S. Appl. No. 12/571,969, Non Final Office Action dated Jun. 26, 2014", 8 pgs.
"U.S. Appl. No. 12/571,969, Non Final Office Action dated Dec. 19, 2012", 7 pgs.
"U.S. Appl. No. 12/571,969, Notice of Allowance dated Jun. 23, 2015", 8 pgs.
"U.S. Appl. No. 12/571,969, Preliminary Amendment filed Mar. 16, 2010", 3 pgs.
"U.S. Appl. No. 12/571,969, Response filed Mar. 6, 2013 to Non Final Office Action dated Dec. 19, 2012", 10 pgs.
"U.S. Appl. No. 12/571,969, Response filed May 15, 2015 to Final Office Action dated Jan. 15, 2015", 16 pgs.
"U.S. Appl. No. 12/571,969, Response filed Jun. 4, 2012 to Restriction Requirement dated May 9, 2012", 9 pgs.
"U.S. Appl. No. 12/571,969, Response filed Sep. 26, 2014 to Non Final Office Action dated Jun. 26, 2014", 12 pgs.
"U.S. Appl. No. 12/571,969, Response filed Sep. 30, 2013 to Final Office Action dated Jul. 31, 2013", 13 pgs.
"U.S. Appl. No. 12/571,969, Restriction Requirement dated May 9, 2012", 9 pgs.
"U.S. Appl. No. 12/714,023, Non Final Office Action dated Jan. 26, 2012", 15 pgs.
"U.S. Appl. No. 12/714,023, Notice of Allowance dated Apr. 9, 2012", 10 pgs.
"U.S. Appl. No. 12/714,023, Response filed Jan. 3, 2012 to Restriction Requirement dated Dec. 12, 2011", 9 pgs.
"U.S. Appl. No. 12/714,023, Response filed Feb. 14, 2012 to Non Final Office Action dated Jan. 26, 2012", 15 pgs.
"U.S. Appl. No. 12/714,023, Restriction Requirement dated Dec. 12, 2011", 5 pgs.
"U.S. Appl. No. 12/872,663, Non Final Office Action dated Jun. 20, 2012", 11 pgs.
"U.S. Appl. No. 12/872,663, Notice of Allowance dated Nov. 15, 2012", 9 pgs.
"U.S. Appl. No. 12/872,663, Response filed May 21, 2012 to Restriction Requirement dated Apr. 27, 2012", 7 pgs.
"U.S. Appl. No. 12/872,663, Restriction Requirement dated Apr. 27, 2012", 6 pgs.
"U.S. Appl. No. 12/872,663, Supplemental Amendment filed Nov. 8, 2012", 8 pgs.
"U.S. Appl. No. 12/888,005, Non Final Office Action dated Jun. 1, 2012", 11 pgs.
"U.S. Appl. No. 12/888,005, Notice of Allowance dated Sep. 27, 2012", 6 pgs.
"U.S. Appl. No. 12/888,005, Response filed May 15, 2012 to Restriction Requirement dated Apr. 27, 2012", 7 pgs.
"U.S. Appl. No. 12/888,005, Response filed Jul. 11, 2012 to Non Final Office Action dated Jun. 1, 2012", 12 pgs.
"U.S. Appl. No. 12/888,005, Restriction Requirement dated Apr. 27, 2012", 7 pgs.
"U.S. Appl. No. 12/893,306, Examiner Interview Summary dated Dec. 18, 2014", 3 pgs.
"U.S. Appl. No. 12/893,306, Final Office Action dated Sep. 11, 2014", 8 pgs.
"U.S. Appl. No. 12/893,306, Non Final Office Action dated Feb. 26, 2014", 9 pgs.
"U.S. Appl. No. 12/893,306, Notice of Allowability dated Jul. 29, 2015", 2 pgs.
"U.S. Appl. No. 12/893,306, Notice of Allowance dated Apr. 14, 2015", 5 pgs.
"U.S. Appl. No. 12/893,306, Response filed Jan. 12, 2015 to Final Office Action dated Sep. 11, 2014", 14 pgs.
"U.S. Appl. No. 12/893,306, Response filed May 22, 2014 to Non Final Office Action dated Feb. 26, 2014", 8 pgs.
"U.S. Appl. No. 12/893,306, Response filed Nov. 4, 2013 to Restriction Requirement dated Oct. 4, 2013", 11 pgs.
"U.S. Appl. No. 12/893,306, Restriction Requirement dated Oct. 4, 2013", 11 pgs.
"U.S. Appl. No. 12/938,905, Advisory Action dated Feb. 4, 2013", 3 pgs.
"U.S. Appl. No. 12/938,905, Appeal Brief filed Feb. 28, 2013", 1 pg.
"U.S. Appl. No. 12/938,905, Appeal Brief filed Apr. 29, 2013", 26 pgs.
"U.S. Appl. No. 12/938,905, Appeal Decision dated Dec. 14, 2015", 18 pgs.
"U.S. Appl. No. 12/938,905, Examiner Interview Summary dated Jan. 30, 2013", 3 pgs.
"U.S. Appl. No. 12/938,905, Examiner Interview Summary dated Jul. 13, 2012", 3 pgs.
"U.S. Appl. No. 12/938,905, Examiner's Answer to Appeal Brief dated Jun. 24, 2013", 8 pgs.
"U.S. Appl. No. 12/938,905, Final Office Action dated Nov. 28, 2012", 11 pgs.
"U.S. Appl. No. 12/938,905, Non Final Office Action dated Jun. 4, 2012", 11 pgs.
"U.S. Appl. No. 12/938,905, Reply Brief filed Aug. 26, 2013", 12 pgs.
"U.S. Appl. No. 12/938,905, Response filed Jan. 28, 2013 to Final Office Action dated Nov. 28, 2012", 19 pgs.
"U.S. Appl. No. 12/938,905, Response filed May 14, 2012 to Restriction Requirement dated Apr. 17, 2012", 7 pgs.
"U.S. Appl. No. 12/938,905, Response filed Jul. 19, 2012 to Non Final Office Action dated Jun. 4, 2012", 20 pgs.

(56) References Cited

OTHER PUBLICATIONS

"U.S. Appl. No. 12/938,905, Response filed Oct. 8, 2012 to Restriction Requirement dated Sep. 14, 2012", 8 pgs.
"U.S. Appl. No. 12/938,905, Restriction Requirement dated Apr. 17, 2012", 8 pgs.
"U.S. Appl. No. 12/938,905, Restriction Requirement dated Sep. 14, 2012", 6 pgs.
"U.S. Appl. No. 12/938,913, Advisory Action dated Jan. 15, 2015", 3 pgs.
"U.S. Appl. No. 12/938,913, Examiner Interview Summary dated Dec. 18, 2014", 3 pgs.
"U.S. Appl. No. 12/938,913, Final Office Action dated Oct. 14, 2014", 9 pgs.
"U.S. Appl. No. 12/938,913, Non Final Office Action dated Mar. 1, 2014", 10 pgs.
"U.S. Appl. No. 12/938,913, Non Final Office Action dated Apr. 9, 2015", 8 pgs.
"U.S. Appl. No. 12/938,913, Notice of Allowance dated Nov. 12, 2015", 5 pgs.
"U.S. Appl. No. 12/938,913, Response filed Jan. 2, 2015 to Final Office Action dated Oct. 1, 2014", 10 pgs.
"U.S. Appl. No. 12/938,913, Response filed Feb. 2, 2015 to Advisory Action dated Jan. 15, 2015", 14 pgs.
"U.S. Appl. No. 12/938,913, Response filed Jun. 11, 2014 to Non Final Office Action dated Mar. 11, 2014", 9 pgs.
"U.S. Appl. No. 12/938,913, Response filed Jul. 7, 2015 to Non Final Office Action dated Apr. 9, 2015", 11 pgs.
"U.S. Appl. No. 12/938,913, Response filed Nov. 6, 2013 to Restriction Requirement dated Oct. 7, 2013", 1 pg.
"U.S. Appl. No. 12/938,913, Restriction Requirement dated Oct. 7, 2013", 7 pgs.
"U.S. Appl. No. 12/955,361, Non Final Office Action dated Mar. 27, 2013", 23 pgs.
"U.S. Appl. No. 12/955,361, Response filed Jun. 27, 2013 to Non Final Office Action dated Mar. 27, 2013", 12 pgs.
"U.S. Appl. No. 12/955,361, Notice of Allowance dated Jul. 18, 2013", 9 pgs.
"U.S. Appl. No. 12/955,361, Notice of Allowance dated Oct. 1, 2013", 4 pgs.
"U.S. Appl. No. 12/955,361, Notice of Allowance dated Oct. 24, 2013", 4 pgs.
"U.S. Appl. No. 12/955,361, Response filed Jan. 14, 2013 to Restriction Requirement dated Dec. 14, 2012", 13 pgs.
"U.S. Appl. No. 12/955,361, Restriction Requirement dated Dec. 14, 2012", 9 pgs.
"U.S. Appl. No. 12/973,214, Response filed Feb. 21, 2014 to Final Office Action dated Nov. 21, 2013", 16 pgs.
"U.S. Appl. No. 12/973,214, Examiner Interview Summary dated Jan. 24, 2014", 3 pgs.
"U.S. Appl. No. 12/973,214, Final Office Action dated Sep. 9, 2015", 10 pgs.
"U.S. Appl. No. 12/973,214, Final Office Action dated Nov. 21, 2013", 14 pgs.
"U.S. Appl. No. 12/973,214, Non Final Office Action dated Feb. 3, 2015", 14 pgs.
"U.S. Appl. No. 12/973,214, Non Final Office Action dated May 22, 2013", 11 pgs.
"U.S. Appl. No. 12/973,214, Notice of Allowance dated Jan. 11, 2016", 8 pgs.
"U.S. Appl. No. 12/973,214, Response filed Apr. 12, 2013 to Restriction Requirement dated Mar. 13, 2013", 9 pgs.
"U.S. Appl. No. 12/973,214, Response filed Jun. 3, 2015 to Non Final Office Action dated Feb. 3, 2015", 13 pgs.
"U.S. Appl. No. 12/973,214, Response filed Aug. 22, 2013 to Non Final Office Action dated May 22, 2013", 12 pgs.
"U.S. Appl. No. 12/973,214, Response filed Nov. 6, 2015 to Final Office Action dated Sep. 9, 2015", 14 pgs.
"U.S. Appl. No. 12/973,214, Restriction Requirement dated Mar. 13, 2013", 8 pgs.
"U.S. Appl. No. 12/978,069, Advisory Action dated Jun. 12, 2013", 3 pgs.
"U.S. Appl. No. 12/978,069, Examiner Interview Summary dated May 28, 2013", 3 pgs.
"U.S. Appl. No. 12/978,069, Final Office Action dated Mar. 25, 2013", 11 pgs.
"U.S. Appl. No. 12/978,069, Non Final Office Action dated Sep. 11, 2012", 11 pgs.
"U.S. Appl. No. 12/978,069, Notice of Allowance dated Jun. 21, 2013", 13 pgs.
"U.S. Appl. No. 12/978,069, Response filed May 23, 2013 to Final Office Action dated Mar. 25, 2013", 17 pgs.
"U.S. Appl. No. 12/978,069, Response filed Aug. 27, 2012 to Restriction Requirement dated Aug. 10, 2012", 8 pgs.
"U.S. Appl. No. 12/978,069, Response filed Dec. 10, 2012 to Non Final Office Action dated Sep. 11, 2012", 15 pgs.
"U.S. Appl. No. 12/978,069, Restriction Requirement dated Aug. 10, 2012", 11 pgs.
"U.S. Appl. No. 12/978,069, Supplemental Notice of Allowance dated Aug. 9, 2013", 3 pgs.
"U.S. Appl. No. 12/978,069, Supplemental Notice of Allowance dated Sep. 17, 2013", 2 pgs.
"U.S. Appl. No. 13/041,469, Non Final Office Action dated Mar. 22, 2013", 12 pgs.
"U.S. Appl. No. 13/041,469, Notice of Allowance dated Aug. 8, 2013", 6 pgs.
"U.S. Appl. No. 13/041,469, Notice of Allowance dated Oct. 3, 2013", 2 pgs.
"U.S. Appl. No. 13/041,469, Notice of Allowance dated Nov. 19, 2013", 2 pgs.
"U.S. Appl. No. 13/041,469, Response filed Jun. 18, 2013 to Non Final Office Action dated Mar. 22, 2013", 15 pgs.
"U.S. Appl. No. 13/041,469, Response filed Oct. 25, 2012 to Restriction Requirement dated Sep. 25, 2012", 1 pg.
"U.S. Appl. No. 13/041,469, Restriction Requirement dated Sep. 25, 2012", 5 pgs.
"U.S. Appl. No. 13/041,495, Appeal Brief filed Oct. 4, 2013", 39 pgs.
"U.S. Appl. No. 13/041,495, Examiner Interview Summary dated Feb. 20, 2013", 3 pgs.
"U.S. Appl. No. 13/041,495, Examiner Interview Summary dated Aug. 6, 2013", 3 pgs.
"U.S. Appl. No. 13/041,495, Final Office Action dated Jun. 18, 2013", 14 pgs.
"U.S. Appl. No. 13/041,495, Non Final Office Action dated Nov. 2, 2012", 10 pgs.
"U.S. Appl. No. 13/041,495, Non Final Office Action dated Dec. 31, 2013", 11 pgs.
"U.S. Appl. No. 13/041,495, Notice of Allowance dated Jun. 11, 2014", 5 pgs.
"U.S. Appl. No. 13/041,495, Response filed Jan. 31, 2013 to Non Final Office Action dated Nov. 2, 2012", 13 pgs.
"U.S. Appl. No. 13/041,495, Response filed Mar. 31, 2014 to Non Final Office Action dated Dec. 31, 2013", 12 pgs.
"U.S. Appl. No. 13/041,495, Response filed Oct. 8, 2012 to Restriction Requirement dated Sep. 25, 2012", 8 pgs.
"U.S. Appl. No. 13/041,495, Restriction Requirement dated Sep. 25, 2012", 7 pgs.
"U.S. Appl. No. 13/041,495, Supplemental Amendment filed Feb. 20, 2013", 15 pgs.
"U.S. Appl. No. 13/041,665, Examiner Interview Summary dated Apr. 30, 2013", 3 pgs.
"U.S. Appl. No. 13/041,665, Final Office Action dated Mar. 5, 2013", 10 pgs.
"U.S. Appl. No. 13/041,665, Non Final Office Action dated Sep. 27, 2012", 10 pgs.
"U.S. Appl. No. 13/041,665, Notice of Allowance dated May 16, 2013", 7 pgs.
"U.S. Appl. No. 13/041,665, Response filed May 3, 2013 to Final Office Action dated Mar. 5, 2013", 13 pgs.
"U.S. Appl. No. 13/041,665, Response filed Sep. 17, 2012 to Restriction Requirement dated Aug. 20, 2012", 6 pgs.

(56) References Cited

OTHER PUBLICATIONS

"U.S. Appl. No. 13/041,665, Response filed Dec. 27, 2012 to Non Final Office Action dated Sep. 27, 2012", 16 pgs.
"U.S. Appl. No. 13/041,665, Restriction Requirement dated Aug. 20, 2012", 9 pgs.
"U.S. Appl. No. 13/041,883, Advisory Action dated May 18, 2016", 3 pgs.
"U.S. Appl. No. 13/041,883, Appeal Brief filed Jul. 25, 2016", 26 pgs.
"U.S. Appl. No. 13/041,883, Examiner Interview Summary dated Oct. 27, 2014", 3 pgs.
"U.S. Appl. No. 13/041,883, Final Office Action dated Jan. 15, 2015", 10 pgs.
"U.S. Appl. No. 13/041,883, Final Office Action dated Feb. 11, 2016", 9 pgs.
"U.S. Appl. No. 13/041,883, Non Final Office Action dated Jun. 26, 2014", 8 pgs.
"U.S. Appl. No. 13/041,883, Non Final Office Action dated Aug. 13, 2015", 10 pgs.
"U.S. Appl. No. 13/041,883, Response filed Feb. 17, 2014 to Restriction Requirement dated Jan. 15, 2014", 3 pgs.
"U.S. Appl. No. 13/041,883, Response filed Apr. 7, 2016 to Final Office Action dated Feb. 11, 2016", 17 pgs.
"U.S. Appl. No. 13/041,883, Response filed May 15, 2015 to Final Office Action dated Jan. 15, 2015", 13 pgs.
"U.S. Appl. No. 13/041,883, Response filed Sep. 26, 2014 to Non Final Office Action dated Jun. 26, 2014", 12 pgs.
"U.S. Appl. No. 13/041,883, Response filed Nov. 6, 2015 to Non Final Office Action dated Aug. 13, 2015", 16 pgs.
"U.S. Appl. No. 13/041,883, Restriction Requirement dated Jan. 15, 2014", 9 pgs.
"U.S. Appl. No. 13/045,169 Applicant's Summary of Examiner Interview filed Sep. 21, 2015", 2 pgs.
"U.S. Appl. No. 13/045,169 Examiner Interview Summary dated Sep. 10, 2015", 3 pgs.
"U.S. Appl. No. 13/045,169 Final Office Action dated Dec. 3, 2015", 8 pgs.
"U.S. Appl. No. 13/045,169 Non Final Office Action dated Jun. 4, 2015", 8 pgs.
"U.S. Appl. No. 13/045,169 Non Final Office Action dated Sep. 24, 2014", 9 pgs.
"U.S. Appl. No. 13/045,169 Response filed May 15, 2014 to Restriction Requirement dated Mar. 14, 2014", 10 pgs.
"U.S. Appl. No. 13/045,169 Response filed Aug. 31, 2015 to Non Final Office Action dated Jun. 4, 2015", 14 pgs.
"U.S. Appl. No. 13/045,169, Response filed Dec. 23, 2014 to Non Final Office Action dated Sep. 24, 2014", 10 pgs.
"U.S. Appl. No. 13/045,169, Restriction Requirement dated Mar. 14, 2014", 10 pgs.
"U.S. Appl. No. 13/047,924, Examiner Interview Summary dated Jan. 21, 2015", 3 pgs.
"U.S. Appl. No. 13/047,924, Examiner Interview Summary dated Jan. 25, 2013", 3 pgs.
"U.S. Appl. No. 13/047,924, Examiner Interview Summary dated Sep. 5, 2013", 3 pgs.
"U.S. Appl. No. 13/047,924, Examiner Interview Summary dated Sep. 18, 2012", 3 pgs.
"U.S. Appl. No. 13/047,924, Final Office Action dated Apr. 3, 2015", 16 pgs.
"U.S. Appl. No. 13/047,924, Final Office Action dated Jul. 18, 2013", 14 pgs.
"U.S. Appl. No. 13/047,924, Non Final Office Action dated Sep. 21, 2012", 11 pgs.
"U.S. Appl. No. 13/047,924, Non Final Office Action dated Nov. 3, 2014", 14 pgs.
"U.S. Appl. No. 13/047,924, Response filed Feb. 3, 2015 to Non Final Office Action dated Nov. 3, 2014", 16 pgs.
"U.S. Appl. No. 13/047,924, Response filed May 1, 2013 to Restriction Requirement dated Apr. 1, 2013", 11 pgs.
"U.S. Appl. No. 13/047,924, Response filed Sep. 17, 2012 to Restriction Requirement dated Aug. 20, 2012", 9 pgs.
"U.S. Appl. No. 13/047,924, Response filed Oct. 18, 2013 to Final Office Action dated Jul. 18, 2013", 18 pgs.
"U.S. Appl. No. 13/047,924, Response filed Dec. 20, 2012 to Non Final Office Action dated Sep. 21, 2012", 19 pgs.
"U.S. Appl. No. 13/047,924, Restriction Requirement dated Apr. 1, 2013", 7 pgs.
"U.S. Appl. No. 13/047,924, Restriction Requirement dated Aug. 20, 2012", 8 pgs.
"U.S. Appl. No. 13/081,618, Examiner Interview Summary dated Feb. 5, 2013", 3 pgs.
"U.S. Appl. No. 13/081,618, Examiner Interview Summary dated Aug. 31, 2012".
"U.S. Appl. No. 13/081,618, Final Office Action dated Nov. 19, 2012", 8 pgs.
"U.S. Appl. No. 13/081,618, Non Final Office Action dated Jul. 25, 2012", 7 pgs.
"U.S. Appl. No. 13/081,618, Notice of Allowance dated Feb. 26, 2013", 9 pgs.
"U.S. Appl. No. 13/081,618, Response filed Feb. 15, 2013 to Final Office Action dated Nov. 19, 2012", 12 pgs.
"U.S. Appl. No. 13/081,618, Response filed Aug. 23, 2012 to Non Final Office Action dated Jul. 25, 2012", 10 pgs.
"U.S. Appl. No. 13/081,618, Supplemental Notice of Allowability dated Jun. 21, 2013", 2 pgs.
"U.S. Appl. No. 13/088,787, Final Office Action dated May 20, 2015", 11 pgs.
"U.S. Appl. No. 13/088,787, Non Final Office Action dated Sep. 11, 2014", 8 pgs.
"U.S. Appl. No. 13/088,787, Notice of Allowance dated Oct. 21, 2015", 6 pgs.
"U.S. Appl. No. 13/088,787, Response filed May 12, 2014 to Restriction Requirement dated Mar. 12, 2014", 10 pgs.
"U.S. Appl. No. 13/088,787, Response filed Aug. 20, 2015 to Final Office Action dated May 20, 2015", 9 pgs.
"U.S. Appl. No. 13/088,787, Response filed Dec. 10, 2014 to Non Final Office Action dated Sep. 11, 2014", 11 pgs.
"U.S. Appl. No. 13/088,787, Restriction Requirement dated Mar. 12, 2014", 9 pgs.
"U.S. Appl. No. 13/106,295, Non Final Office Action dated Jan. 24, 2013", 14 pgs.
"U.S. Appl. No. 13/106,295, Notice of Allowance dated Aug. 1, 2013", 9 pgs.
"U.S. Appl. No. 13/106,295, Response filed Apr. 16, 2013 to Non Final Office Action dated Jan. 24, 2013", 10 pgs.
"U.S. Appl. No. 13/106,295, Response filed Dec. 20, 2012 to Restriction Requirement dated Nov. 23, 2012", 1 pg.
"U.S. Appl. No. 13/106,295, Restriction Requirement dated Nov. 23, 2012", 5 pgs.
"U.S. Appl. No. 13/111,007, Non Final Office Action dated Mar. 25, 2013", 10 pgs.
"U.S. Appl. No. 13/111,007, Notice of Allowance dated Aug. 1, 2013", 8 pgs.
"U.S. Appl. No. 13/111,007, Notice of Allowance dated Oct. 4, 2013", 2 pgs.
"U.S. Appl. No. 13/111,007, Notice of Allowance dated Nov. 7, 2013", 2 pgs.
"U.S. Appl. No. 13/111,007, Response filed Jun. 20, 2013 to Non Final Office Action dated Mar. 25, 2013", 12 pgs.
"U.S. Appl. No. 13/111,007, Response filed Nov. 26, 2012 to Restriction Requirement dated Sep. 24, 2012", 13 pgs.
"U.S. Appl. No. 13/111,007, Restriction Requirement dated Sep. 24, 2012", 7 pgs.
"U.S. Appl. No. 13/303,546, Non Final Office Action dated Jun. 29, 2012", 12 pgs.
"U.S. Appl. No. 13/303,546, Notice of Allowance dated Nov. 6, 2012", 10 pgs.
"U.S. Appl. No. 13/303,546, Response filed Jun. 14, 2012 to Restriction Requirement dated May 30, 2012", 7 pgs.
"U.S. Appl. No. 13/303,546, Response filed Aug. 16, 2012 to Non Final Office Action dated Jun. 29, 2012", 11 pgs.

(56) References Cited

OTHER PUBLICATIONS

"U.S. Appl. No. 13/303,546, Restriction Requirement dated May 30, 2012", 6 pgs.
"U.S. Appl. No. 13/303,546, Supplemental Notice of Allowance dated Jan. 8, 2013", 4 pgs.
"U.S. Appl. No. 13/303,546, Supplemental Notice of Allowance dated Feb. 13, 2013", 4 pgs.
"U.S. Appl. No. 13/343,957, Non Final Office Action dated Feb. 20, 2014", 14 pgs.
"U.S. Appl. No. 13/343,957, Notice of Allowance dated Jul. 24, 2014", 7 pgs.
"U.S. Appl. No. 13/343,957, Response filed May 20, 2014 to Non Final Office Action dated Feb. 20, 2014", 14 pgs.
"U.S. Appl. No. 13/400,652, Corrected Notice of Allowance dated Feb. 1, 2016", 2 pgs.
"U.S. Appl. No. 13/400,652, Non Final Office Action dated Jun. 17, 2015", 7 pgs.
"U.S. Appl. No. 13/400,652, Notice of Allowance dated Jan. 11, 2016", 7 pgs.
"U.S. Appl. No. 13/400,652, Response filed Jan. 28, 2015 to Restriction Requirement dated Nov. 28, 2014", 17 pgs.
"U.S. Appl. No. 13/400,652, Response filed Apr. 13, 2015 to Restriction Requirement dated Feb. 13, 2015", 16 pgs.
"U.S. Appl. No. 13/400,652, Response filed Aug. 8, 2014 to Restriction Requirement dated Jun. 13, 2014", 19 pgs.
"U.S. Appl. No. 13/400,652, Response filed Sep. 16, 2015 to Non Final Office Action dated Jun. 17, 2015", 12 pgs.
"U.S. Appl. No. 13/400,652, Restriction Requirement dated Feb. 13, 2015", 8 pgs.
"U.S. Appl. No. 13/400,652, Restriction Requirement dated Jun. 13, 2014", 9 pgs.
"U.S. Appl. No. 13/400,652, Restriction Requirement dated Nov. 28, 2014", 7 pgs.
"U.S. Appl. No. 13/527,981, Advisory Action dated Jan. 20, 2016", 3 pgs.
"U.S. Appl. No. 13/527,981, Final Office Action dated Feb. 5, 2015", 22 pgs.
"U.S. Appl. No. 13/527,981, Final Office Action dated Nov. 6, 2015", 13 pgs.
"U.S. Appl. No. 13/527,981, Non Final Office Action dated Feb. 26, 2015", 10 pgs.
"U.S. Appl. No. 13/527,981, Non Final Office Action dated Jul. 28, 2016", 11 pgs.
"U.S. Appl. No. 13/527,981, Non Final Office Action dated Sep. 15, 2014", 19 pgs.
"U.S. Appl. No. 13/527,981, Response filed Jan. 6, 2016 to Final Office Action dated Nov. 6, 2015", 14 pgs.
"U.S. Appl. No. 13/527,981, Response filed May 27, 2014 to Restriction Requirement dated Mar. 27, 2014", 11 pgs.
"U.S. Appl. No. 13/527,981, Response filed Jul. 27, 2015 to Non-Final Office Action dated Feb. 26, 2015", 25 pgs.
"U.S. Appl. No. 13/527,981, Response Filed Oct. 28, 2016 to Non-Final Office Action dated Jul. 28, 2016", 15 pgs.
"U.S. Appl. No. 13/527,981, Restriction Requirement dated Mar. 27, 2014", 7 pgs.
"U.S. Appl. No. 13/572,895, Non Final Office Action dated Nov. 7, 2013", 5 pgs.
"U.S. Appl. No. 13/572,895 Notice of Allowance dated Apr. 29, 2014", 7 pgs.
"U.S. Appl. No. 13/572,895, Response filed Feb. 7, 2014 to Non Final Office Action dated Nov. 7, 2013", 13 pgs.
"U.S. Appl. No. 13/674,531 Response Filed Mar. 30, 2016 to Non-Final Office Action dated Sep. 30, 2015", 10 pgs.
"U.S. Appl. No. 13/674,531 Advisory Action dated Aug. 6, 2015", 3 pgs.
"U.S. Appl. No. 13/674,531 Final Office Action dated Apr. 29, 2015", 8 pgs.
"U.S. Appl. No. 13/674,531 Non Final Office Action dated Sep. 30, 2015", 8 pgs.
"U.S. Appl. No. 13/674,531 Non Final Office Action dated Dec. 1, 2014", 9 pgs.
"U.S. Appl. No. 13/674,531 Notice of Allowance dated Jun. 14, 2016", 16 pgs.
"U.S. Appl. No. 13/674,531 Response filed Mar. 2, 2015 to Non Final Office Action dated Dec. 1, 2014", 12 pgs.
"U.S. Appl. No. 13/674,531, Response filed Jul. 29, 2015 to Final Office Action dated Apr. 29, 2015", 12 pgs.
"U.S. Appl. No. 13/674,531, Response filed Oct. 9, 2014 to Restriction Requirement dated Sep. 24, 2014", 3 pgs.
"U.S. Appl. No. 13/674,531, Restriction Requirement dated Sep. 24, 2014", 7 pgs.
"U.S. Appl. No. 13/713,710, Notice of Allowance dated Sep. 15, 2015", 10 pgs.
"U.S. Appl. No. 13/713,710, Response filed Aug. 25, 2015 to Restriction Requirement dated Jul. 2, 2015", 7 pgs.
"U.S. Appl. No. 13/713,710, Restriction Requirement dated Jul. 2, 2015", 6 pgs.
"U.S. Appl. No. 13/744,022, Advisory Action dated Oct. 27, 2014", 3 pgs.
"U.S. Appl. No. 13/744,022, Final Office Action dated Jul. 14, 2014", 9 pgs.
"U.S. Appl. No. 13/744,022, Non Final Office Action dated Jan. 30, 2014", 20 pgs.
"U.S. Appl. No. 13/744,022, Notice of Allowance dated Nov. 28, 2014", 9 pgs.
"U.S. Appl. No. 13/744,022, Response filed Apr. 25, 2014 to Non Final Office Action dated Jan. 30, 2014", 16 pgs.
"U.S. Appl. No. 13/744,022, Response filed Oct. 8, 2014 to Final Office Action dated Jul. 14, 2014", 15 pgs.
"U.S. Appl. No. 13/766,419, Advisory Action dated May 18, 2015", 2 pgs.
"U.S. Appl. No. 13/766,419, Final Office Action dated Jan. 13, 2015", 16 pgs.
"U.S. Appl. No. 13/766,419, Non Final Office Action dated Sep. 5, 2014", 14 pgs.
"U.S. Appl. No. 13/766,419, Response filed May 12, 2015 to Final Office Action dated Jan. 13, 2015", 13 pgs.
"U.S. Appl. No. 13/766,419, Response filed Dec. 5, 2014 to Non Final Office Action dated Sep. 5, 2014", 12 pgs.
"U.S. Appl. No. 13/800,334, Examiner Interview Summary dated Jan. 29, 2015", 4 pgs.
"U.S. Appl. No. 13/800,334, Final Office Action dated Feb. 12, 2015", 11 pgs.
"U.S. Appl. No. 13/800,334, Non Final Office Action dated Sep. 24, 2015", 14 pgs.
"U.S. Appl. No. 13/800,334, Non Final Office Action dated Oct. 22, 2014", 11 pgs.
"U.S. Appl. No. 13/800,334, Non Final Office Action dated Dec. 15, 2016", 26 pgs.
"U.S. Appl. No. 13/800,334, Response filed Jan. 21, 2015 to Non Final Office Action dated Oct. 22, 2014", 12 pgs.
"U.S. Appl. No. 13/800,334, Response filed Jun. 24, 2016 to Final Office Action dated Apr. 7, 2016", 19 pgs.
"U.S. Appl. No. 13/800,334, Response filed Jul. 10, 2015 to Final Office Action dated Feb. 12, 2015", 8 pgs.
"U.S. Appl. No. 13/800,334, Response filed Dec. 16, 2015 to Non Final Office Action dated Sep. 24, 2015", 16 pgs.
"U.S. Appl. No. 13/923,827, Advisory Action dated Oct. 9, 2014", 3 pgs.
"U.S. Appl. No. 13/923,827, Examiner Interview Summary dated Sep. 29, 2014", 3 pgs.
"U.S. Appl. No. 13/923,827, Final Office Action dated Jul. 28, 2014", 11 pgs.
"U.S. Appl. No. 13/923,827, Non Final Office Action dated Apr. 10, 2014", 9 pgs.
"U.S. Appl. No. 13/923,827, Notice of Allowance dated Oct. 29, 2014", 11 pgs.
"U.S. Appl. No. 13/923,827, Response filed Jul. 10, 2014 to Non Final Office Action dated Apr. 10, 2014", 13 pgs.
"U.S. Appl. No. 13/923,827, Response filed Sep. 29, 2014 to Final Office Action dated Jul. 28, 2014", 11 pgs.

(56) References Cited

OTHER PUBLICATIONS

"U.S. Appl. No. 13/923,827, Supplemental Notice of Allowance dated Feb. 11, 2015", 2 pgs.
"U.S. Appl. No. 13/923,827, Supplemental Notice of Allowance dated Dec. 19, 2014", 3 pgs.
"U.S. Appl. No. 14/027,340, Advisory Action dated Sep. 17, 2015", 3 pgs.
"U.S. Appl. No. 14/027,340, Final Office Action dated Jul. 8, 2015", 10 pgs.
"U.S. Appl. No. 14/027,340, Non Final Office Action dated Jan. 22, 2015", 11 pgs.
"U.S. Appl. No. 14/027,340, Non Final Office Action dated Dec. 9, 2015", 10 pgs.
"U.S. Appl. No. 14/027,340, Notice of Allowance dated May 12, 2016", 7 pgs.
"U.S. Appl. No. 14/027,340, Response filed Feb. 19, 2016 to Non Final Office Action dated Dec. 9, 2015", 13 pgs.
"U.S. Appl. No. 14/027,340, Response filed May 21, 2015 to Non Final Office Action dated Jan. 22, 2015", 14 pgs.
"U.S. Appl. No. 14/027,340, Response filed Sep. 9, 2015 to Final Office Action dated Jul. 8, 2015", 15 pgs.
"U.S. Appl. No. 14/064,970, Advisory Action dated Jan. 4, 2016", 3 pgs.
"U.S. Appl. No. 14/064,970, Final Office Action dated Oct. 19, 2015", 10 pgs.
"U.S. Appl. No. 14/064,970, Non Final Office Action dated Mar. 12, 2015", 11 pgs.
"U.S. Appl. No. 14/064,970, Non Final Office Action dated Jul. 26, 2016", 12 pgs.
"U.S. Appl. No. 14/064,970, Notice of Allowance dated Jan. 27, 2017", 10 pgs.
"U.S. Appl. No. 14/064,970, Response filed Jul. 8, 2015 to Non Final Office Action dated Mar. 12, 2015", 8 pgs.
"U.S. Appl. No. 14/064,970, Response filed Oct. 26, 2016 to Non Final Office Action dated Jul. 26, 2016", 14 pgs.
"U.S. Appl. No. 14/064,970, Response filed Dec. 19, 2014 to Restriction Requirement dated Oct. 9, 2014", 11 pgs.
"U.S. Appl. No. 14/064,970, Response filed Dec. 15, 2015 to Final Office Action dated Oct. 19, 2015", 11 pgs.
"U.S. Appl. No. 14/064,970, Restriction Requirement dated Oct. 9, 2014", 9 pgs.
"U.S. Appl. No. 14/086,447, Notice of Allowance dated Aug. 12, 2016", 9 pgs.
"U.S. Appl. No. 14/086,447, Preliminary Amendment filed Jul. 29, 2016", 4 pgs.
"U.S. Appl. No. 14/086,447, Response filed May 4, 2016 to Restriction Requirement dated Apr. 6, 2016", 7 pgs.
"U.S. Appl. No. 14/086,447, Restriction Requirement dated Apr. 6, 2016", 7 pgs.
"U.S. Appl. No. 14/100,134 Response Filed Apr. 14, 2016 to Restriction Requirement dated Feb. 24, 2016", 7 pgs.
"U.S. Appl. No. 14/100,134, Notice of Allowance dated Jun. 16, 2016", 14 pgs.
"U.S. Appl. No. 14/100,134, Restriction Requirement dated Feb. 24, 2016", 5 pgs.
"U.S. Appl. No. 14/105,669, Non Final Office Action dated Jan. 11, 2016", 11 pgs.
"U.S. Appl. No. 14/105,669, Non Final Office Action dated Aug. 11, 2016", 5 pgs.
"U.S. Appl. No. 14/105,669, Notice of Allowance dated Jan. 26, 2017", 7 pgs.
"U.S. Appl. No. 14/105,669, Response filed Oct. 13, 2015 to Restriction Requirement dated Sep. 8, 2015", 7 pgs.
"U.S. Appl. No. 14/105,669, Response filed Oct. 31, 2016 to Non Final Office Action dated Aug. 11, 2016", 8 pgs.
"U.S. Appl. No. 14/105,669, Restriction Requirement dated Sep. 8, 2015", 6 pgs.
"U.S. Appl. No. 14/106,669, Response filed Apr. 11, 2016 to Non Final Office Action dated Jan. 11, 2016", 11 pgs.
"U.S. Appl. No. 14/107,316, Corrected Notice of Allowance dated Jul. 11, 2016", 2 pgs.
"U.S. Appl. No. 14/107,316, Examiner Interview Summary dated Jun. 10, 2016", 3 pgs.
"U.S. Appl. No. 14/107,316, Non Final Office Action dated Mar. 24, 2016", 16 pgs.
"U.S. Appl. No. 14/107,316, Notice of Allowance dated Jun. 28, 2016", 11 pgs.
"U.S. Appl. No. 14/107,316, Notice of Non-Compliant Amendment dated Dec. 30, 2015", 3 pgs.
"U.S. Appl. No. 14/107,316, Response filed Jan. 18, 2016 to Notice of Non-Compliant Amendment dated Dec. 30, 2015", 8 pgs.
"U.S. Appl. No. 14/107,316, Response filed Jun. 13, 2016 to Non Final Office Action dated Mar. 24, 2016", 13 pgs.
"U.S. Appl. No. 14/107,316, Response filed Dec. 16, 2015 to Restriction Requirement dated Oct. 29, 2015", 8 pgs.
"U.S. Appl. No. 14/107,316, Restriction Requirement dated Oct. 29, 2015", 8 pgs.
"U.S. Appl. No. 14/159,071, Final Office Action dated May 14, 2015", 7 pgs.
"U.S. Appl. No. 14/159,071, Non Final Office Action dated Dec. 8, 2014", 14 pgs.
"U.S. Appl. No. 14/483,214, Final Office Action dated Dec. 16, 2015", 9 pgs.
"U.S. Appl. No. 14/483,214, Non Final Office Action dated Jun. 5, 2015", 8 pgs.
"U.S. Appl. No. 14/483,214, Non Final Office Action dated Oct. 6, 2016", 12 pgs.
"U.S. Appl. No. 14/483,214, Response filed Jan. 6, 2017 to Non Final Office Action dated Oct. 6, 2016", 16 pgs.
"U.S. Appl. No. 14/483,214, Response filed Mar. 14, 2016 to Final Office Action dated Dec. 16, 2015", 15 pgs.
"U.S. Appl. No. 14/483,214, Response filed May 15, 2015 to Restriction Requirement dated Mar. 25, 2015", 2 pgs.
"U.S. Appl. No. 14/483,214, Response filed Sep. 2, 2015 to Non Final Office Action dated Jun. 5, 2015", 13 pgs.
"U.S. Appl. No. 14/483,214, Restriction Requirement dated Mar. 25, 2015", 6 pgs.
"U.S. Appl. No. 14/658,429, Final Office Action dated Aug. 29, 2016", 9 pgs.
"U.S. Appl. No. 14/658,429, Non Final Office Action dated Mar. 24, 2016", 7 pgs.
"U.S. Appl. No. 14/658,429, Response filed Nov. 21, 2016 to Final Office Action dated Aug. 29, 2016", 14 pgs.
"U.S. Appl. No. 14/658,429, Response Filed Jun. 20, 2016 to Non-Final Office Action dated Mar. 24, 2016", 12 pgs.
"U.S. Appl. No. 14/684,936, Corrected Notice of Allowance dated Sep. 22, 2016", 4 pgs.
"U.S. Appl. No. 14/684,936, Non Final Office Action dated Mar. 22, 2016", 7 pgs.
"U.S. Appl. No. 14/684,936, Notice of Allowance dated Aug. 30, 2016", 6 pgs.
"U.S. Appl. No. 14/684,936, Response filed Jun. 9, 2016 to Non Final Office Action dated Mar. 22, 2016", 8 pgs.
"U.S. Appl. No. 14/798,809, Preliminary Amendment filed Oct. 29, 2015", 7 pgs.
"U.S. Appl. No. 14/798,809, Restriction Requirement dated Jan. 4, 2017", 10 pgs.
"U.S. Appl. No. 14/812,583, Preliminary Amendment filed Jul. 29, 2015", 6 pgs.
"U.S. Appl. No. 14/812,583, Restriction Requirement dated Jan. 23, 2017", 8 pgs.
"U.S. Appl. No. 14/865,762, Preliminary Amendment filed Oct. 14, 2015", 6 pgs.
"U.S. Appl. No. 14/973,057, Non Final Office Action dated Oct. 18, 2016", 6 pgs.
"U.S. Appl. No. 14/973,057, Preliminary Amendment filed Dec. 18, 2015", 7 pgs.
"U.S. Appl. No. 14/973,057, Response filed Jan. 18, 2017 to Non Final Office Action dated Oct. 18, 2016", 8 pgs.
"U.S. Appl. No. 14/973,057, Response filed Sep. 21, 2016 to Restriction Requirement dated Jul. 29, 2016", 5 pgs.

(56) References Cited

OTHER PUBLICATIONS

"U.S. Appl. No. 14/973,057, Restriction Requirement dated Jul. 29, 2016", 8 pgs.
"U.S. Appl. No. 14/983,077, Preliminary Amendment filed Dec. 30, 2015", 6 pgs.
"U.S. Appl. No. 15/008,528, Preliminary Amendment dated Jan. 29, 2016", 8 pgs.
"U.S. Appl. No. 15/093,384, Preliminary Amendment filed Apr. 28, 2016", 5 pgs.
"U.S. Appl. No. 15/224,741, Preliminary Amendment filed Sep. 12, 2016", 8 pgs.
"U.S. Appl. No. 15/267,714, Preliminary Amendment filed Oct. 16, 2016", 7 pgs.
"U.S. Appl. No. 15/267,714, Restriction Requirement dated Jan. 5, 2017", 5 pgs.
"U.S. Appl. No. 15/352,721, Corrected Notice of Allowance dated Apr. 27, 2017", 2 pgs.
"U.S. Appl. No. 15/352,721, Notice of Allowance dated Mar. 10, 2017", 11 pgs.
"U.S. Appl. No. 15/352,721, Preliminary Amendment filed Feb. 3, 2017", 6 pgs.
"U.S. Appl. No. 12/025,414, Applicant's Summary of Examiner Interview filed Apr. 9, 2012", 4 pgs.
"U.S. Appl. No. 12/025,414, Final Office Action dated Mar. 14, 2012", 6 pgs.
"U.S. Appl. No. 12/025,414, Final Office Action dated May 1, 2012", 10 pgs.
"U.S. Appl. No. 12/025,414, Non Final Office Action dated Oct. 25, 2011", 10 pgs.
"U.S. Appl. No. 12/025,414, Notice of Allowance dated Jun. 13, 2012", 7 pgs.
"U.S. Appl. No. 12/025,414, Response filed Apr. 9, 2012 to Final Office Action dated Mar. 14, 2012", 15 pgs.
"U.S. Appl. No. 12/025,414, Response filed May 21, 2012 to Final Office Action dated May 1, 2012", 6 pgs.
"U.S. Appl. No. 12/025,414, Response filed Jul. 26, 2011 to Restriction Requirement dated Jul. 19, 2011", 8 pgs.
"U.S. Appl. No. 12/025,414, Response filed Dec. 22, 2011 to Non Final Office Action dated Oct. 25, 2011", 13 pgs.
"U.S. Appl. No. 12/025,414, Restriction Requirement dated Jul. 19, 2011", 5 pgs.
"U.S. Appl. No. 12/483,807, Final Office Action dated Nov. 4, 2011", 20 pgs.
"U.S. Appl. No. 12/872,663, Response filed Sep. 13, 2012 to Non Final Office Action dated Jun. 20, 2012", 9 pgs.
"U.S. Appl. No. 13/800,334, Final Office Action dated Apr. 6, 2016", 19 pgs.
"Ascent Total Knee System", Biomet, Inc., (Oct. 31, 1999), 16 pgs.
"Australian Application Serial No. 2013222609, First Examiner Report dated Feb. 16, 2015", 5 pgs.
"Australian Application Serial No. 2013222609, Response filed Sep. 17, 2015 to First Examiner Report dated Feb. 16, 2015", 17 pgs.
"C2a-Taper™ Ceramic-on-Ceramic Articulation", Surgical Technique, Biomet Orthopedics, (2007), 20 pgs.
"Comprehensive® Reverse Shoulder System", Biomet Orthopedics brochure, (2009), 8 pgs.
"Comprehensive® Reverse Shoulder System Surgical Technique", Biomet Orthopedics, (2009-2012), 48 pgs.
"Comprehensive® Reverse Shoulder System Technical Design Features", Biomet Orthopedics, (2009), 3 pgs.
"Comprehensive® Shoulder System Surgical Technique", Biomet Orthopedics brochure, (2007), 1-53.
"Comprehensive® Total Shoulder System", Biomet Orthopedics brochure, (2011), 4 pgs.
"Customized Patient Instruments, Patient specific instruments for patient specific needs", DePuy Orthopaedics, Inc., (2008), 14 pgs.
"Customized Patient Instruments, Primary Cruciate Retaining Surgical Technique for use with the Sigma® Knee System Utilizing Specialist® 2 Instrumentation", DePuy Orthopaedics, Inc., (2008), 1-23.
"Discovery® Elbow System", Biomet Orthopedics, Inc., (Nov. 30, 2007), 3 pgs.
"Discovery® Elbow System Surgical Technique", Biomet Orthopedics, Inc., (Dec. 31, 2008), 1-25.
"DURALOC® Cementless Acetabular Reconstruction", Surgical Technique brochure, DePuy International Ltd., (2007), 10 pgs.
"European Application Serial 13710642.3, Communication Pursuant to Article 94(3) EPC dated Nov. 6, 2015", 3 pgs.
"European Application Serial 13710642.3, Intention to grant dated Jun. 17, 2016", 7 pgs.
"European Application Serial 13710642.3, Response filed Mar. 16, 2016 to Communication Pursuant to Article 94(3) EPC dated Nov. 6, 2015", 8 pgs.
"European Application Serial No. 07809326.7, Examination Notification Art. 94(3) dated Jan. 22, 2015", 6 pgs.
"European Application Serial No. 07809326.7, Extended European Search Report dated Nov. 15, 2011", 6 pgs.
"European Application Serial No. 07809326.7, Office Action dated Jan. 28, 2009", 2 pgs.
"European Application Serial No. 07809326.7, Office Action dated Dec. 2, 2011", 1 pg.
"European Application Serial No. 07809326.7, Response filed Jun. 6, 2012 to Extended European Search Report dated Nov. 15, 2011", 6 pgs.
"European Application Serial No. 07809326.7, Response filed Jul. 31, 2015 to Examination Notification Art. 94(3) dated Jan. 22, 2015", 10 pgs.
"European Application Serial No. 09731923.0, Communication Pursuant to Article 94(3) EPC dated Nov. 29, 2016", 5 pgs.
"European Application Serial No. 09731923.0, Examination Notification Art. 94(3) dated Feb. 10, 2015", 7 pgs.
"European Application Serial No. 09731923.0, Office Action dated Feb. 3, 2011", 2 pgs.
"European Application Serial No. 09731923.0, Response filed Aug. 20, 2015 to Examination Notification Art. 94(3) dated Feb. 10, 2015", 11 pgs.
"European Application Serial No. 09732174.9, Communication Pursuant to Article 94(3) EPC dated Mar. 3, 2016", 4 pgs.
"European Application Serial No. 09732174.9, Communication Pursuant to Article 94(3) EPC dated Oct. 17, 2016", 4 pgs.
"European Application Serial No. 09732174.9, Examination Notification Art. 94(3) dated Mar. 7, 2014", 5 pgs.
"European Application Serial No. 09732174.9, Office Action dated Feb. 3, 2011", 2 pgs.
"European Application Serial No. 09732174.9, Response filed Jul. 13, 2016 to Communication Pursuant to Article 94(3) EPC dated Mar. 3, 2016", 12 pgs.
"European Application Serial No. 09732174.9, Response filed Jul. 14, 2014 to Examination Notification Art. 94(3) dated Mar. 7, 2014", 6 pgs.
"European Application Serial No. 09792468.2, Communication Pursuant to Article 94(3) EPC dated Jun. 7, 2016", 4 pgs.
"European Application Serial No. 09792468.2, Examination Notification Art. 94(3) dated Jan. 29, 2015", 5 pgs.
"European Application Serial No. 09792468.2, Office Action dated Jul. 8, 2011", 2 pgs.
"European Application Serial No. 09792468.2, Response filed Jan. 9, 2012 to Office Action dated Jul. 8, 2011", 11 pgs.
"European Application Serial No. 09792468.2, Response filed May 29, 2015 to Examination Notification Art. 94(3) dated Jan. 29, 2015", 8 pgs.
"European Application Serial No. 09792468.2, Response filed Sep. 28, 2016 to Communication Pursuant to Article 94(3) EPC dated Jun. 7, 2016", 21 pgs.
"European Application Serial No. 10705064.3, Communication Pursuant to Article 94(3) EPC dated Dec. 8, 2015", 4 pgs.
"European Application Serial No. 10705064.3, Examination Notification Art. 94(3) dated Feb. 4, 2015", 6 pgs.

(56) References Cited

OTHER PUBLICATIONS

"European Application Serial No. 10705064.3, Office Action dated Nov. 22, 2011", 2 pgs.
"European Application Serial No. 10705064.3, Response filed Apr. 18, 2016 to Communication Pursuant to Article 94(3) EPC dated Dec. 8, 2015", 8 pgs.
"European Application Serial No. 10705064.3, Response filed Aug. 14, 2015 to Examination Notification Art. 94(3) dated Feb. 4, 2015", 9 pgs.
"European Application Serial No. 10705951.1, Communication Pursuant to Article 94(3) EPC dated Jan. 22, 2013", 7 pgs.
"European Application Serial No. 10705951.1, Office Action dated Oct. 7, 2011", 2 pgs.
"European Application Serial No. 10705951.1, Response filed May 23, 2013 to Communication Pursuant to Article 94(3) EPC dated Jan. 22, 2013", 8 pgs.
"European Application Serial No. 12156937.0, Decision of Grant dated May 4, 2015", 2 pgs.
"European Application Serial No. 12156937.0, Examination Notification Art. 94(3) dated Dec. 11, 2013", 5 pgs.
"European Application Serial No. 12156937.0, Extended European Search Report dated Sep. 6, 2012", 9 pgs.
"European Application Serial No. 12156937.0, Response filed Apr. 16, 2013 to Extended European Search Report dated Sep. 6, 2012", 9 pgs.
"European Application Serial No. 12156937.0, Response filed Apr. 17, 2014 to Examination Notification Art. 94(3) dated Dec. 11, 2013", 15 pgs.
"European Application Serial No. 12724475.4, Communication Pursuant to Article 94(3) EPC dated Aug. 31, 2016", 5 pgs.
"European Application Serial No. 12724475.4, Examination Notification Art. 94(3) dated Nov. 24, 2014", 7 pgs.
"European Application Serial No. 12724475.4, Office Action dated Jan. 21, 2014", 2 pgs.
"European Application Serial No. 12724475.4, Response filed Jan. 10, 2017 to Communication Pursuant to Article 94(3) EPC dated Aug. 31, 2016", 17 pgs.
"European Application Serial No. 12724475.4, Response filed Apr. 15, 2015 to Examination Notification Art. 94(3) dated Nov. 24, 2014", 9 pgs.
"European Application Serial No. 13710642.3, Amendment dated Sep. 1, 2014", 7 pgs.
"European Application Serial No. 13710642.3, Office Action dated Oct. 10, 2014", 2 pgs.
"Great Britain Application Serial No. 1116054.6, Search Report dated Dec. 21, 2011", 4 pgs.
"Hand Instruments", High Performance, Precision Series brochure by Arthrotek, copyright, (2000), 3 pgs.
"Hipsextant Instructions of Use", Surgical Planning Associates, Inc., (2011), 19 pgs.
"International Application Serial No. PCT/EP2010/061630, International Search Report dated Nov. 30, 2010", 3 pgs.
"International Application Serial No. PCT/GB2007/003737, International Preliminary Report on Patentability dated Apr. 7, 2009", 8 pgs.
"International Application Serial No. PCT/GB2007/003737, Written Opinion dated Jan. 25, 2008", 7 pgs.
"International Application Serial No. PCT/US2007/013223, International Preliminary Report on Patentability dated Dec. 24, 2008", 5 pgs.
"International Application Serial No. PCT/US2007/013223, International Search Report dated Nov. 26, 2007", 3 pgs.
"International Application Serial No. PCT/US2007/013223, Written Opinion dated Nov. 26, 2007", 4 pgs.
"International Application Serial No. PCT/US2009/039507, International Preliminary Report on Patentability dated Oct. 28, 2010", 9 pgs.
"International Application Serial No. PCT/US2009/039507, International Search Report dated Jul. 14, 2009", 6 pgs.
"International Application Serial No. PCT/US2009/039507, Written Opinion dated Jul. 14, 2009", 7 pgs.
"International Application Serial No. PCT/US2009/039578, International Preliminary Report on Patentability dated Oct. 28, 2010", 9 pgs.
"International Application Serial No. PCT/US2009/039578, International Search Report dated Jul. 31, 2009", 6 pgs.
"International Application Serial No. PCT/US2009/039578, Written Opinion dated Jul. 31, 2009", 7 pgs.
"International Application Serial No. PCT/US2009/056670, International Preliminary Report on Patentability dated Mar. 31, 2011", 12 pgs.
"International Application Serial No. PCT/US2009/056670, International Search Report dated Mar. 2, 2010", 7 pgs.
"International Application Serial No. PCT/US2009/056670, Invitation to Pay Additional Fees and Partial Search Report dated Nov. 26, 2009".
"International Application Serial No. PCT/US2009/056670, Written Opinion dated Mar. 2, 2010", 10 pgs.
"International Application Serial No. PCT/US2009/061434, International Preliminary Report on Patentability dated May 11, 2011", 6 pgs.
"International Application Serial No. PCT/US2009/061434, International Search Report dated Feb. 2, 2010", 4 pgs.
"International Application Serial No. PCT/US2009/061434, Written Opinion dated Feb. 2, 2010", 4 pgs.
"International Application Serial No. PCT/US2010/024073, International Preliminary Report on Patentability dated Aug. 25, 2011", 8 pgs.
"International Application Serial No. PCT/US2010/024073, International Search Report dated Jun. 4, 2010", 4 pgs.
"International Application Serial No. PCT/US2010/024073, Written Opinion dated Jun. 4, 2010", 6 pgs.
"International Application Serial No. PCT/US2010/024579, International Preliminary Report on Patentability dated Sep. 1, 2011", 7 pgs.
"International Application Serial No. PCT/US2010/024579, International Search Report dated Apr. 22, 2010", 3 pgs.
"International Application Serial No. PCT/US2010/024579, Written Opinion dated Apr. 22, 2010", 5 pgs.
"International Application Serial No. PCT/US2010/024584, International Preliminary Report on Patentability dated Sep. 1, 2011", 8 pgs.
"International Application Serial No. PCT/US2010/024584, International Search Report dated Aug. 19, 2010", 6 pgs.
"International Application Serial No. PCT/US2010/024584, Written Opinion dated Aug. 19, 2010", 6 pgs.
"International Application Serial No. PCT/US2010/028325, International Preliminary Report on Patentability dated Oct. 6, 2011", 8 pgs.
"International Application Serial No. PCT/US2010/028325, International Search Report dated Jun. 11, 2010", 6 pgs.
"International Application Serial No. PCT/US2010/028325, Written Opinion dated Jun. 11, 2010", 6 pgs.
"International Application Serial No. PCT/US2010/038177, International Preliminary Report on Patentability dated Dec. 22, 2011", 10 pgs.
"International Application Serial No. PCT/US2010/038177, International Search Report dated Aug. 24, 2010", 4 pgs.
"International Application Serial No. PCT/US2010/038177, Written Opinion dated Aug. 24, 2010", 8 pgs.
"International Application Serial No. PCT/US2010/038845, International Preliminary Report on Patentability dated Jan. 5, 2012", 9 pgs.
"International Application Serial No. PCT/US2010/038845, International Search Report dated Oct. 5, 2010", 4 pgs.
"International Application Serial No. PCT/US2010/038845, Written Opinion dated Oct. 5, 2010", 7 pgs.
"International Application Serial No. PCT/US2010/050701, International Preliminary Report on Patentability dated Apr. 12, 2012", 10 pgs.
"International Application Serial No. PCT/US2010/050701, International Search Report dated Dec. 7, 2010", 6 pgs.

(56) References Cited

OTHER PUBLICATIONS

"International Application Serial No. PCT/US2010/050701, Written Opinion dated Dec. 7, 2010", 8 pgs.
"International Application Serial No. PCT/US2011/026333, International Preliminary Report on Patentability dated Sep. 7, 2012", 10 pgs.
"International Application Serial No. PCT/US2011/026333, International Search Report dated Aug. 9, 2011", 6 pgs.
"International Application Serial No. PCT/US2011/026333, Invitation to Pay Additional Fees dated May 3, 2011".
"International Application Serial No. PCT/US2011/026333, Written Opinion dated Aug. 9, 2011", 8 pgs.
"International Application Serial No. PCT/US2011/026412, International Preliminary Report on Patentability dated Sep. 30, 2012", 8 pgs.
"International Application Serial No. PCT/US2011/026412, International Search Report dated May 9, 2011", 5 pgs.
"International Application Serial No. PCT/US2011/026412, Written Opinion dated May 9, 2011", 6 pgs.
"International Application Serial No. PCT/US2011/057300, International Preliminary Report on Patentability dated May 16, 2013", 11 pgs.
"International Application Serial No. PCT/US2011/057300, International Search Report dated Mar. 5, 2012", 7 pgs.
"International Application Serial No. PCT/US2011/057300, Written Opinion dated Mar. 5, 2012", 9 pgs.
"International Application Serial No. PCT/US2012/026356, International Preliminary Report on Patentability dated Sep. 6, 2013", 8 pgs.
"International Application Serial No. PCT/US2012/026356, International Search Report dated May 8, 2012", 5 pgs.
"International Application Serial No. PCT/US2012/026356, Written Opinion dated May 8, 2012", 6 pgs.
"International Application Serial No. PCT/US2012/038351, International Search Report dated Jul. 12, 2012", 6 pgs.
"International Application Serial No. PCT/US2012/038351, International Preliminary Report on Patentability dated Nov. 28, 2013", 9 pgs.
"International Application Serial No. PCT/US2012/038351, Written Opinion dated Jul. 6, 2012", 8 pgs.
"International Application Serial No. PCT/US2012/041893, International Search Report dated Oct. 23, 2012", 5 pgs.
"International Application Serial No. PCT/US2012/042081, International Preliminary Report on Patentability dated Jan. 3, 2014", 7 pgs.
"International Application Serial No. PCT/US2012/042081, Written Opinion dated Sep. 5, 2012", 6 pgs.
"International Application Serial No. PCT/US2012/052853, International Preliminary Report on Patentability dated Mar. 13, 2014", 14 pgs.
"International Application Serial No. PCT/US2012/052853, International Search Report dated Nov. 15, 2012", 6 pgs.
"International Application Serial No. PCT/US2012/052853, Written Opinion dated Nov. 15, 2012", 12 pgs.
"International Application Serial No. PCT/US2012/059189, International Preliminary Report on Patentability dated Apr. 24, 2014", 10 pgs.
"International Application Serial No. PCT/US2012/059189, International Search Report dated Dec. 18, 2012", 6 pgs.
"International Application Serial No. PCT/US2012/059189, Written Opinion dated Dec. 18, 2012", 9 pgs.
"International Application Serial No. PCT/US2012/060842, International Preliminary Report on Patentability dated May 8, 2014", 7 pgs.
"International Application Serial No. PCT/US2012/060842, International Search Report dated Feb. 6, 2013", 4 pgs.
"International Application Serial No. PCT/US2012/060842, Written Opinion dated Feb. 6, 2013", 5 pgs.
"International Application Serial No. PCT/US2012/060848, International Preliminary Report on Patentability dated May 8, 2014", 11 pgs.
"International Application Serial No. PCT/US2012/060848, International Search Report dated Apr. 12, 2013", 6 pgs.
"International Application Serial No. PCT/US2012/060848, Invitation to Pay Additional Fees dated Feb. 6, 2013".
"International Application Serial No. PCT/US2012/060848, Written Opinion dated Apr. 12, 2013", 9 pgs.
"International Application Serial No. PCT/US2012/060853, International Preliminary Report on Patentability dated May 8, 2014", 11 pgs.
"International Application Serial No. PCT/US2012/060853, Invitation to Pay Additional Fees dated Feb. 7, 2013", 4 pgs.
"International Application Serial No. PCT/US2012/060853, Written Opinion dated Apr. 9, 2013", 9 pgs.
"International Application Serial No. PCT/US2012/060854, International Preliminary Report on Patentability dated May 8, 2014", 8 pgs.
"International Application Serial No. PCT/US2012/060854, International Search Report dated Feb. 6, 2013", 4 pgs.
"International Application Serial No. PCT/US2012/060854, Written Opinion dated Feb. 6, 2013", 6 pgs.
"International Application Serial No. PCT/US2013/026875, International Preliminary Report on Patentability dated Sep. 4, 2014", 9 pgs.
"International Application Serial No. PCT/US2013/026875, International Search Report dated Jun. 7, 2013", 5 pgs.
"International Application Serial No. PCT/US2013/026875, Written Opinion dated Jun. 7, 2013", 8 pgs.
"International Application Serial No. PCT/US2013/057097, International Preliminary Report on Patentability dated Mar. 12, 2015", 10 pgs.
"International Application Serial No. PCT/US2013/057097, International Search Report dated Oct. 14, 2013", 6 pgs.
"International Application Serial No. PCT/US2013/057097, Written Opinion dated Oct. 14, 2013", 9 pgs.
"International Application Serial No. PCT/US2013/067505, International Preliminary Report on Patentability dated May 14, 2015", 13 pgs.
"International Application Serial No. PCT/US2013/067505, International Search Report dated Apr. 14, 2014", 5 pgs.
"International Application Serial No. PCT/US2013/067505, Invitation to Pay Additional Fees dated Feb. 6, 2014", 6 pgs.
"International Application Serial No. PCT/US2013/067505, Written Opinion dated Apr. 14, 2014", 11 pgs.
"International Application Serial No. PCT/US2013/074288, International Preliminary Report on Patentability dated Jun. 25, 2015", 13 pgs.
"International Application Serial No. PCT/US2013/074288, International Search Report dated May 23, 2014", 7 pgs.
"International Application Serial No. PCT/US2013/074288, Written Opinion dated May 23, 2014", 11 pgs.
"International Application Serial No. PCT/US2014/022000, International Search Report dated Jun. 24, 2014", 3 pgs.
"International Application Serial No. PCT/US2014/022000, Written Opinion dated Jun. 24, 2014", 5 pgs.
"International Application Serial No. PCT/US2014/023655, International Search Report dated Jul. 10, 2014", 4 pgs.
"International Application Serial No. PCT/US2014/023655, Written Opinion dated Jul. 10, 2014", 6 pgs.
"International Application Serial No. PCT/US2014/068131, International Search Report dated May 8, 2015", 5 pgs.
"International Application Serial No. PCT/US2014/068131, Written Opinion dated May 8, 2015", 9 pgs.
"International Application Serial No. PCT/US2015/039561, International Preliminary Report on Patentability dated Jan. 19, 2017", 8 pgs.
"International Application Serial No. PCT/US2015/039561, International Search Report dated Sep. 14, 2015", 5 pgs.
"International Application Serial No. PCT/US2015/039561, Written Opinion dated Sep. 14, 2015", 6 pgs.

(56) References Cited

OTHER PUBLICATIONS

"Is Subchondroplasty® Right for Me?", [Online] retrieved from the internet: <http://www.subchondroplast}'..com/about subchondroplast}'./is subchondroplasty right for >, (Jul. 1, 2013), 1 pg.
"Japanese Application Serial No. 2011-505080, Appeal Decision dated Jun. 24, 2015", (W/ English Translation), 3 pgs.
"Japanese Application Serial No. 2011-505080, Decision of Refusal dated Nov. 27, 2013", (W/ English Translation), 4 pgs.
"Japanese Application Serial No. 2011-505080, Office Action dated Feb. 25, 2015", (W/ English Translation), 2 pgs.
"Japanese Application SerialNo. 2011-505080, Office Action dated Apr. 3, 2013", (W/ English Translation), 6 pgs.
"Japanese Application Serial No. 2011-505080, Response filed Mar. 27, 2014 to Decision of Refusal dated Nov. 27, 2013", (W/ English Translation), 12 pgs.
"Japanese Application Serial No. 2011-505080, Response filed May 25, 2015 to Office Action dated Feb. 25, 2015", No English Translation, 6 pgs.
"Japanese Application Serial No. 2011-505080, Response filed Jul. 3, 2013 to Office Action dated Apr. 3, 2013", (W/ English Translation), 11 pgs.
"Japanese Application Serial No. 2011-527885, Office Action dated Aug. 27, 2013", (English Translation), 8 pgs.
"Japanese Application Serial No. 2011-527885, Response filed Nov. 26, 2013 to Office Action dated Aug. 27, 2013", (W/ English Translation of Claims), 9 pgs.
"Japanese Application Serial No. 2013-537691, Office Action dated Feb. 10, 2015", No English Translation, 3 pgs.
"Japanese Application Serial No. 2013-537691, Office Action dated Apr. 15, 2014", (W/ English Translation), 2 pgs.
"Japanese Application Serial No. 2013-537691, Office Action dated Aug. 19, 2014", (W/ English Translation), 4 pgs.
"Japanese Application Serial No. 2013-537691, Response filed Jul. 5, 2014 to Office Action dated Apr. 15, 2014", No English Translation, 7 pgs.
"Japanese Application Serial No. 2013-537691, Response filed Dec. 19, 2014 to Office Action dated Aug. 19, 2014", No English Translation, 8 pgs.
"Japanese Application Serial No. 2014-257600, Examiners Decision of Final Refusal dated Dec. 20, 2016", (W/ English Translation), 2 pgs.
"Japanese Application Serial No. 2014-257600, Office Action dated May 24, 2016", (W/ English Translation), 5 pgs.
"Japanese Application Serial No. 2014-257600, Office Action dated Oct. 27, 2015", (W/ English Translation), 6 pgs.
"Japanese Application Serial No. 2014-257600, Response filed Jan. 20, 2016 to Office Action dated Oct. 27, 2015", (W/ English Translation of Claims), 5 pgs.
"Japanese Application Serial No. 2014-257600, Voluntary Amendment filed Dec. 19, 2014", No English Translation, 16 pgs.
"Japanese Application Serial No. 2014-511538, Office Action dated Apr. 7, 2015", (W/ English Translation), 5 pgs.
"Japanese Application Serial No. 2014-511538, Office Action dated Nov. 17, 2015", W/ English Translation, 5 pgs.
"Japanese Application Serial No. 2014-511538, Response filed Feb. 17, 2016 to Office Action dated Nov. 17, 2015", (W/ English Translation of Claims), 9 pgs.
"Japanese Application Serial No. 2014-511538, Response filed Jul. 6, 2015 to Office Action dated Apr. 7, 2015", No English Translation, 6 pgs.
"Japanese Application Serial No. 2014-558800, Office Action dated Sep. 1, 2015", (W/ English Translation), 8 pgs.
"Japanese Application Serial No. 2014-558800, Response filed Dec. 1, 2015 to Office Action dated Sep. 1, 2015", (W/ English Translation), 9 pgs.
"Japanese Application Serial No. 2014511538, Office Action dated Apr. 7, 2015", (W/ English Translation), 8 pgs.
"Knee tensor combined with laser femoral head locator", Research Disclosure, No. 507, (Jul. 2006), 903.
"Insall/Burstein II Modular Knee System", Zimmer, Inc., (1989), 20 pgs.
"Magnum™, M2a-Magnum™ Operative Technique", brochure. Biomet UK Ltd., (2008), 14 pgs.
"MAX-Ti™ Modular Protrusio Cage", Surgical Technique brochure. Biomet Orthopedics, Inc., (2003), 10 pgs.
"MAX-Ti™ Modular Protrusio Cage", Surgical Technique brochure. Biomet Orthopedics, Inc., (2006), 12 pgs.
"Method for constructing an allograft sleeve", Research Disclosure, No. 476, (Dec. 2003), 1294.
"Minimally Invasive Solution Technique—Instrumentation", The M/G Unicompartmental Knee, (2001), 4 pgs.
"MIS Minimally Invasive Solution, The M/G Unicompartmental Knee Minimally Invasive Surgical Technique", Zimmer, Inc. Nexgen Complete Knee Solution, 97-5791-02, (Aug. 14, 2008), 27 pgs.
"Nex Gen Complete Knee Solution—Intramedually Instrumentation Surgical Technique", NexGen Cruciate Retaining & Legacy Posterior Stablized Knee, (1994), 37 pgs.
"Nexgen Complete Knee Solution", Extramedullary/Intramedullary Tibial Resector: Surgical Technique, Zimmer, Inc. 97-5997-02 Rev 1, (2000), 26 pgs.
"NexGen Complete Knee Solution—Multi-Reference 4-in-1 Femoral Instrumentation—Anterior Reference Surgical Technique", (Aug. 1, 2001), 17 pgs.
"NexGen System Complete Knee Solution—Design Rationale", (date unknown), 26 pgs.
"Orthopaedic Salvage System Femoral/Tibial Augmentation", Biomet Orthopedics, Inc., Product Brochure, (2003, 2004), 12 pgs.
"OSS™ Orthopaedic Salvage System, Femoral/Tibial Augmentation", Biomet Orthopedics, Inc.,, (Mar. 31, 2004), 1-8.
"Oxford® Partial Knee", Biomet, (Feb. 2011), 8 pgs.
"Oxford® Partial Knee Microplasty® Instrumentation Surgical Technique", Biomet, (May 2011), 1-54.
"PAR 5™ Protrusio Acetabular Reconstruction System", Biomet Orthopedics, Inc., (2006), 12 pgs.
"Patient Matched PMI Implants, C.A.M.R.A. 3-D Imaging", Brochure, Biomet, Inc., Form Y-BMI-191/013191, (1991), 6 pgs.
"Proximal Tibial Replacement (MOST)", Zimmer MOST Options System Surgical Technique, (2005), 84 pgs.
"Regenerex® Porous Titanium Construct", Biomet brochure, (2011), 12 pgs.
"Regenerex® Tibial Cone Augment, Surgical Technique Addendum to the Vanguard® SSK Revision System", brochure. Biomet® Orthopedics., (Mar. 31, 2010), 1-8.
"Scorpio Single Axis Total Knee System—Passport Total Knee Instruments", Suri:iical TechniQue by Srvker Howmedica Osteonics, (2000), 54 pgs.
"Signature™ Hip Technology Personalized Patient Care brochure", Biomet® Orthopedics., (2013), 8 pgs.
"Signature™ Personalized Patient Care", Surgical Technique Acetabular Guide System brochure, Biomet® Orthopedics, (2013), 1-13.
"Signature™ Personalized Patient Care, Surgical Technique Addendum to the Vanguard Knee System", Biomet® Orthopedics Brochure, (May 15, 2009), 1-8.
"Simple Instruments Surgical Technique for the Knee", Biomet, Inc., (2000), 4 pgs.
"Subchondroplasty", [Online] retrieved from the internet: <http://www.subchondroplasty.com/>, (Jul. 1, 2013), 1 pg.
"Surgical Navigation for Total Knee Arthroplasty—Believed to have been presented at the American Academy of Orthopedic Surgeons", (Feb. 2001), 24 pgs.
"Surgical Technique for the Maxim®, Ascent™ and Vanguard™ Total Knee Systems", Microplasty™ minimally invasive knee instruments brochure, (Feb. 29, 2004), 15 pgs.
"Surgical Technique—Nexgen Complete Knee Solution for the Legacy Knee LPS-Flex Fixed Bearing Knee", Zimmer, Inc., (2004, 2007), 12 pgs.
"Taperloc Complete Hip System Surgical Technique", Biomet: Brochure 2012 REV061512, (2011), 12 pgS.
"The AGC Revision Knee System Surgical Technique", Biomet, Inc., (1997), 14 pgs.

(56) References Cited

OTHER PUBLICATIONS

"The Fudger™—The Ultimate Weapon in the Femoral Referencing War", Biomet, Inc., 2 pgs.
"The Oxford® Partial Knee Surgical Technique", Biomet, (Feb. 2010), 1-38.
"TruMatch™ Personalized knee replacement solutions", SIGMA® DePuy Orthopaedics, Inc, tri-fold brochure, (2009), 2 pgs.
"United Kingdom Application Serial No. 0619534.1, Search Report dated Dec. 18, 2006", (dated Dec. 8, 2006), 1 pg.
"United Kingdom Application Serial No. 1116054.6, Office Action dated Aug. 12, 2016", 2 pgs.
"United Kingdom Application Serial No. 1116054.6, Response filed Oct. 11, 2016 to Office Action dated Aug. 12, 2016", 12 pgs.
"United Kingdom Application Serial No. 11160546, First Examination Report dated Jun. 6, 2016", 4 pgs.
"United Kingdom Application Serial No. 1207103.1, Amendment filed Apr. 13, 2012", 9 pgs.
"United Kingdom Application Serial No. 1207103.1, Office Action dated May 14, 2015", 3 pgs.
"United Kingdom Application Serial No. 1207103.1, Office Action dated Oct. 6, 2015", 2 pgs.
"United Kingdom Application Serial No. 1207103.1, Response filed Sep. 14, 2015 to Office Action dated May 14, 2015", 22 pgs.
"United Kingdom Application Serial No. 1216577.5, Office Action dated Oct. 20, 2016", 4 pgs.
"United Kingdom Application Serial No. 1216577.5, Office Action dated Oct. 29, 2015", 4 pgs.
"United Kingdom Application Serial No. 1216577.5, Response filed Feb. 24, 2016 to Office Action dated Oct. 29, 2015", 27 pgs.
"United Kingdom Application Serial No. 1216577.5, Response filed Oct. 25, 2016 to Office Action dated Oct. 20, 2016", 24 pgs.
"United Kingdom Application Serial No. 1308746.5, Office Action dated Oct. 14, 2016", 5 pgs.
"United Kingdom Application Serial No. 1516672.1, Combined Search and Examination Report dated Oct. 22, 2015", 5 pgs.
"United Kingdom Application Serial No. 1516672.1, Office Action dated Mar. 7, 2016", 3 pgs.
"United Kingdom Application Serial No. 1516672.1, Response filed Feb. 22, 2016 to Combined Search and Examination Report dated Oct. 22, 2015", (English Translation of Claims), 37 pgs.
"United Kingdom Application Serial No. 1516672.1, Response filed Apr. 13, 2016 to Office Action dated Mar. 7, 2016", 13 pgs.
"Vanguard Complete Knee System", Biomet Othopedics, Vanguard, System Summary, (2011), 8 pgs.
"Vanguard® PFR Partial Knee Patellofemoral Replacement System", Surgical Technique, Biomet Orthopaedics (Aug. 31, 2010), 1-25.
"Vision Acetabular Surgical TechniQue", Biomet Orthopedics, Inc brochure, (2001), 16 pgs.
"What is Subchondroplasty", [Online]. Retrieved from the Internet: <http://www.subchondroplasty.com/about subchondroplasty/what is subchondroplasty.>, (Jul. 1, 2013), 2 pgs.
"Zimmer MIS Multi-Reference 4-in-1 Femoral Instrumentation Surgical Technique", Zimmer, Inc., (2003, 2008, 2009), 48 pgs.
"Zimmer® UniSpacer® Knee System", Zimmer, Inc., (2005), 4 pgs.
Biomet, "The Oxford® Partial Knee System Surgical Technique", Biomet: Manual of the Surgical Technique, (Feb. 2010), 44 pgs.
Birnbaum, Klaus M. D, "Computer-Assisted Orthopedic Surgery With Individual Templates and Comparison to Conventional Method", SPINE vol. 26, No. 4, Lippincott Williams & Wilkins, Inc., (2001), 365-370.
Botha, Charl P, "Technical Report: DeVIDE—The Delft Visualisation and Image processing Development Environment", (May 31, 2006), 1-49.
Clohisy, John C, et al., "Periacetabular Osteotomy in the Treatment of Severe Acetabular Dysplasia", The Journal of Bone & Joint Surgery, vol. 87-A • No. 2, (2005), 7 pgs.
Cohen, Zohara A, et al., "Knee cartilage topography, thickness, and contact areas from MRI: in-vitro calibration and in-vivo measurements", Journal of the OsteoArthritis Research Society International. Osteoarthritis and Cartilage, vol. 7; No. 1, (1999), 95-109.
Deakon, "Posterior Cruciate Ligament Reconstruction Technique Using the Modular ACL/PCL Guide Rationale and Surgical Technique", Arthrotek®, a Biomet Company, (2003), 6 pgs.
Eckhoff, Donald G, et al., "Three-Dimensional Mechanics, Kinematics, and Morphology of the Knee Viewed in Virtual Reality", The Journal of Bone & Joint Surgery, vol. 81, (Dec. 4, 2005), 71-80.
Farr, J, et al., "Anteromedial Tibial Tubercle Osteotomy (Fulkerson Osteotomy)", Re-print from V. Sanchis-Alfonso (ed), Anterior Knee Pain and patellar Instability, DOI: 10.1007/978-0-85729-507-1_40, © Springer-Verlag London Limited, (2011), 9 pgs.
Farr, J, et al., "Surgical Technique for Anteromedialization of the Tibial Tubercle with the Tracker™ AMZ Guide System", Sports Medicine and Arthroscopy Review, vol. 2, No. 3, (1994), 12 pgs.
Fortin, Thomas, et al., "Precise Dental Implant Placement in Bone Using Surgical Guides in Conjunction with Medical Imaging Techniques", Journal of Oral Implantology, Clinical, vol. 26, No. 4, (2000), 300-303.
Friedman, R J, et al., "The Use of Computerized Tomography in the Measurement of Glenoid Version", Journal of Bone & Joint Surgery Am. (JBJS) 1992;74, (Aug. 1992), 1032-1037.
Genant, H K, et al., "Advanced CT bone imaging in osteoporosis", Rheumatology, 47, (2008), 8 pgs.
Guldberg, et al., "3D Imaging of Tissue Integration with Porous Biomaterials", Biomaterials, 29, (Oct. 2008), 3757-3761.
Haaker, R G, et al., "Minimal-invasive navigiert implantierte unikondylare Knieendoprothese", Orthopade 2006 35: Spinger Medizin Verlag, (Sep. 13, 2006), 1073-1079.
Hafez, M A, et al., "Computer-assisted Total Knee Arthroplasty Using Patient-specific Templating", Clinical Orthopaedics and Related Research, No. 444 Lippincott Williams & Wilkins, (2006), 184-192.
Hazan, Eric J, "Computer-Assisted Orthopaedic Surgery, A New Paradigm", Techniques in Orthopaedics® vol. 18, No. 2 (2003), 221-229.
Hitt, Kirby, et al., "Anthropometric Measurements of the Human Knee: Correlation to the Sizing of Current Knee Arthroplasty Systems", The Journal of Bone & Joint Surgery, (2003), 114-122.
Hutmacher, Dietmar W, "Scaffolds in tissue engineering bone and cartilage", Biomaterials, 21(24), (2000), 2529-2543.
Kaus, Michael R, "Automated Segmentation of MR Images of Brain Tumors", Radiology, vol. 218, No. 2 (2001), 586-591.
Kelly, Todd C, "Role of Navigation in Total Hip Arthroplasty", The Journal of Bone & Joint Surgery(2009) vol. 91-A, Supplement 1, (2009), 153-8.
Keys, Graham W., "Reduced Invasive Approach for Oxford II Medial Unicompartmental Knee Replacement—a Preliminary Study", The Knee, (1999), 193-196.
Klein, M, "Robot assisted insertion of craniofacial implants—clinical experience", CARS 2001, Elsevier Science B.V., (2001), 133-138.
Lombardi, Adolph, et al., "Patient-Specific Approach in Total Knee Arthroplasty", Knee Orthopedics, ORTHOSuperSite, [Online]. Retrieved from the Internet: <http://www.orthosupersite.com/view.aspx?rid=31419,>, (Sep. 1, 2008), 5 pgs.
Lynch, John A, et al., "Cartilage segmentation of 3D MRI scans of the osteoarthritic knee combining user knowledge and active contours", Medical Imaging 2000: Image Processing SPIE vol. 3979, (2000), 925-935.
Masatoshi, Naito, et al., "Curved Periacetabular Osteotomy for Treatment of Dysplastic Hip", Clinical Orthopaedics and Related Research, (Apr. 2005), 129-135.
Miller, et al., "Unicompartmental Knee System", The Miller/Galante Advantage; Zimmer, 11 pgs.
Miller, Nancy H, et al., "Long-term Results of the Dial Osteotomy in the Treatment of High-grade Acetabular Dysplasia", Clinical Orthopaedics and Related Research, (2005), 115-123.
Murphy, S B, et al., "The Hip Sextant: Navigation of Acetabular Component Orientation Using a Mechanical Instrument", (2009), 1 pg.
Nicholls, Paul M. D, "Trauma Grand Rounds PMI (Patient-Matched Implants)", Biomet Orthopedics, Inc.,, (Feb. 29, 2000), 1 pg.

(56) References Cited

OTHER PUBLICATIONS

Overhoff, H M, et al., "Total Knee Arthroplasty: Coordinate System Definition and Planning based on 3-D Ultrasound Image Volumes", CARS 2001, Elsevier Science B.V., (2001), 283-288.

Patsch, J M, et al., "Noninvasive imaging of bone microarchitecture", Annals of the NY Academy of Sciences, (2011), 77-87.

Portheine, F, "CT-basierte Planung und DISOS-Schablonennavigation in der Kniegelenkendoprothetik", Navigation und Robotic in der Gelenk—und Wirbelsaulenchiruqie, Kapitel 32, Springer Verlag, (2003), 262-269.

Portheine, F, et al., "Entwicklung eines klinischen Demonstrators fur die computerunterstutzte Orthopadische Chirurgie mit CT-Bildbasierten Individualschablonen, Bildverarbeitung fur die Medizin", English version: FIP ID 752773, (1998), 5 pgs.

Portheine, K, "Development of a clinical demonstrator for computer assisted orthopedic surgery with CT-image based individual templates", Computer Assisted Radiology and Surgery Elsevier Science B.V., English Version of FIP ID 752770, (1997), 944-949.

Radermacher, K, et al., "Computer Integrated Orthopaedic Surgery: Connection of Planning and Execution in Surgical Intervention", Computer-integrated surgery: technology and clinical applications, (1996), 451-463.

Radermacher, K, et al., "CT Image-Based Planning and Execution of Interventions in Orthopedic Surgery Using Individual Templates, Experimental Results and Aspects of Clinical Applications", Computer Assisted Orthopedic Surgery (CAOS), Hogrefe & Huber Publishers, (1995), 42-52.

Radermacher, K, et al., "Image Guided Orthopedic Surgery Using Individual Templates", Springer Berlin/Heidelberg, CVRMed-MRCAS'97, vol. 1205, (1997), 606-615.

Radermacher, K, et al., "Technique for Better Execution of CT Scan Planned Orthopedic Surgery on Bone Structures", British Library—"The world's knowledge" 2nd Congress of ISCAS Conference, (Jun. 1995), 933-938.

Radermacher, Klaus, et al., "Computer Assisted Orthopaedic Surgery with Image Based Individual Templates", Clinical Orthopaedics and Related Research No. 354, Lippincott Williams & Wilkins, (Sep. 1998), 28-38.

Schuller-Gotzburg, P, et al., "3D-Implantatplanung und Stereolithographie-Implantatbohrschablonen", Stomatologie 101.3, (May 2004), 55-59.

Sharp, Michael S, "Patient-Specific, Resurfacing Bi-Compartmental Arthuroplasty Futuretech", Orthopaedic Product News, (Apr. 2008), 12-15.

Sisto, Domenick J, et al., "Custom Patellofemoral Arthroplasty of the Knee Surgical Technique", Journal of Bone and Joint Surgery, vol. 89-A, (2006), 214-225.

Slamin, John, et al., "Do You Have This Implant in My Size?", MDT Medical Design Technology, [Online]. Retrieved from the Internet: <http://www.mdtmag.com/scripts/ShowPR.asp-?PUBCODE=046&ACCT=0007796& ISSUE . . . >, (Jul. 31, 2008), 3 pgs.

Steinwachs, Matthias Reinhard, "Cartilage Repair—Autologous Chondrocyte Transplantation and Autologous Matrix-induced Chondrogenesis", European Musculoskeletal Review, (2006), 65-68.

Subburaj, K, et al., "Automated 3D Geometric Reasoning in Computer Assisted Joint Reconstructive Surgery", IEEE International Conference on Automation Science and Engineering, (2009), 367-372.

Thoma, W, et al., "Endoprothetischen Versorgung des Kniegelenks auf der Basis eines 3D-computertomographischen Subtraktionverfahrens", Topic: Computer-aided orthopedic surgery. Orthopedist 2000 29: Springer Verlag W/ Original German Document, (2000), 641-644.

Tripp, et al., "A Nondestructive Prescreening Method for Bone Collagen Content Using Micro-Computed Tomography", Radiocarbon, vol. 52, (2010), 612-619.

Yasunaga, Yuji, et al., "Rotational Acetabular Osteotomy for Advanced Osteoarthritis Secondary to Dysplasia of the Hip. Surgical Technique", The Journal of Bone & Joint Surgery, (2007), 11 pgs.

U.S. Appl. No. 15/130,4145, filed Apr. 15, 2016, Patient-Specific Acetabular Guides and Associated Instruments.

"U.S. Appl. No. 12/255,945, Appeal Decision dated Feb. 27, 2017", 12 pgs.

"U.S. Appl. No. 12/255,945, Notice of Allowance dated May 5, 2017", 7 pgs.

"U.S. Appl. No. 12/371,096, Appeal Decision dated Jun. 23, 2017", 10 pgs.

"U.S. Appl. No. 13/041,883, Examiner's Answer dated Mar. 8, 2017", 8 pgs.

"U.S. Appl. No. 13/041,883, Reply Brief Filed May 2, 2017 to Examiner's Answer dated Mar. 8, 2017", 8 pgs.

"U.S. Appl. No. 13/527,981, Examiner Interview Summary dated Apr. 24, 2017", 5 pgs.

"U.S. Appl. No. 13/527,981, Final Office Action dated Feb. 8, 2017", 17 pgs.

"U.S. Appl. No. 13/527,981, Non Final Office Action dated Jun. 22, 2017", 6 pgs.

"U.S. Appl. No. 13/527,981, Response filed May 8, 2017 to Final Office Action dated Feb. 8, 2017", 18 pgs.

"U.S. Appl. No. 13/800,334, Final Office Action dated Jun. 15, 2017", 22 pgs.

"U.S. Appl. No. 13/800,334, Response filed Mar. 15, 2017 to Non Final Office Action dated Dec. 15, 2016", 16 pgs.

"U.S. Appl. No. 14/064,970, Notice of Allowability dated Feb. 10, 2017", 2 pgs.

"U.S. Appl. No. 14/064,970, Notice of Allowability dated Feb. 17, 2017", 2 pgs.

"U.S. Appl. No. 14/327,234, Notice of Allowance dated Jun. 22, 2017", 12 pgs.

"U.S. Appl. No. 14/327,234, Response filed May 17, 2017 to Restriction Requriement dated Apr. 6, 2017", 8 pgs.

"U.S. Appl. No. 14/327,234, Restriction Requirement dated Apr. 6, 2017", 7 pgs.

"U.S. Appl. No. 14/483,214, Examiner Interview Summary dated Apr. 12, 2017", 3 pgs.

"U.S. Appl. No. 14/483,214, Non Final Office Action dated May 2, 2017", 10 pgs.

"U.S. Appl. No. 14/658,429, Final Office Action dated Jun. 15, 2017", 7 pgs.

"U.S. Appl. No. 14/658,429, Non Final Office Action dated Feb. 23, 2017", 6 pgs.

"U.S. Appl. No. 14/658,429, Response Filed May 19, 2017 to Non-Final Office Action dated Feb. 23, 2017", 15 pgs.

"U.S. Appl. No. 14/798,809, Non Final Office Action dated Jun. 28, 2017", 7 pgs.

"U.S. Appl. No. 14/798,809, Response filed Apr. 3, 2017 to Restriction Requirement dated Jan. 4, 2017", 8 pgs.

"U.S. Appl. No. 14/812,583, Non Final Office Action dated May 9, 2017", 14 pgs.

"U.S. Appl. No. 14/812,583, Response filed Mar. 16, 2017 to Restriction Requirement dated Jan. 23, 2017", 6 pgs.

"U.S. Appl. No. 14/865,762, Non Final Office Action dated Jun. 13, 2017", 13 pgs.

"U.S. Appl. No. 14/865,762, Response filed May 17, 2017 to Restrictiion Requirement dated Apr. 13, 2017", 8 pgs.

"U.S. Appl. No. 14/865,762, Restriction Requirement dated Apr. 13, 2017", 6 pgs.

"U.S. Appl. No. 14/973,057, Corrected Notice of Allowance dated May 30, 2017", 2 pgs.

"U.S. Appl. No. 14/973,057, Final Office Action dated Feb. 13, 2017", 7 pgs.

"U.S. Appl. No. 14/973,057, Notice of Allowance dated Apr. 27, 2017", 7 pgs.

"U.S. Appl. No. 14/973,057, Response filed Apr. 5, 2017 to Final Office Action dated Feb. 13, 2017", 9 pgs.

"U.S. Appl. No. 15/130,414, Preliminary Amendment filed Mar. 9, 2017", 6 pgs.

(56) References Cited

OTHER PUBLICATIONS

"U.S. Appl. No. 15/267,714, Non Final Office Action dated May 10, 2017", 23 pgs.

"U.S. Appl. No. 15/267,714, Response filed Feb. 28, 2017 to Restriction Requirement dated Jan. 5, 2017", 8 pgs.

"U.S. Appl. No. 15/495,432, Preliminary Amendment filed May 17, 2017", 8 pgs.

"European Application Serial No. 09731923.0, Response filed Apr. 10, 2017 to Communication Pursuant to Article 94(3) EPC dated Nov. 29, 2016", 18 pgs.

"European Application Serial No. 09732174.9, Response filed Feb. 22, 2017 to Communication Pursuant to Article 94(3) EPC dated Oct. 17, 2016", 6 pgs.

"European Application Serial No. 16179349.2, Extended European Search Report dated Mar. 22, 2017", 9 pgs.

\* cited by examiner

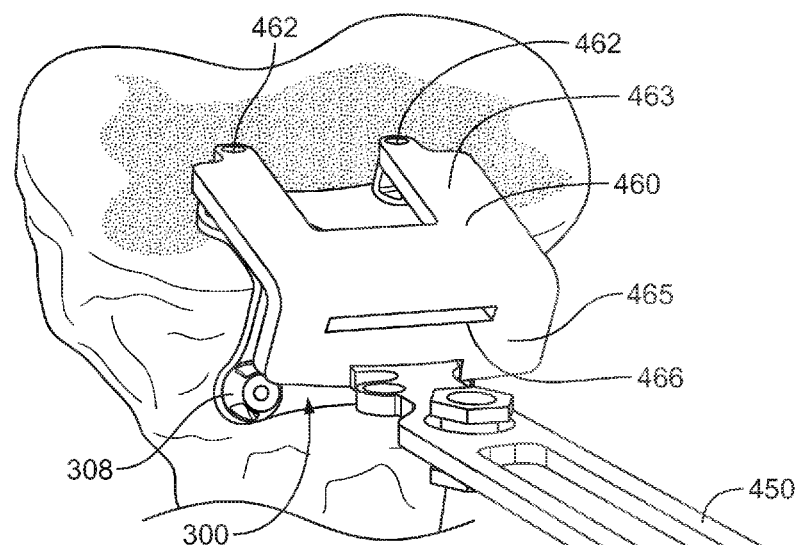
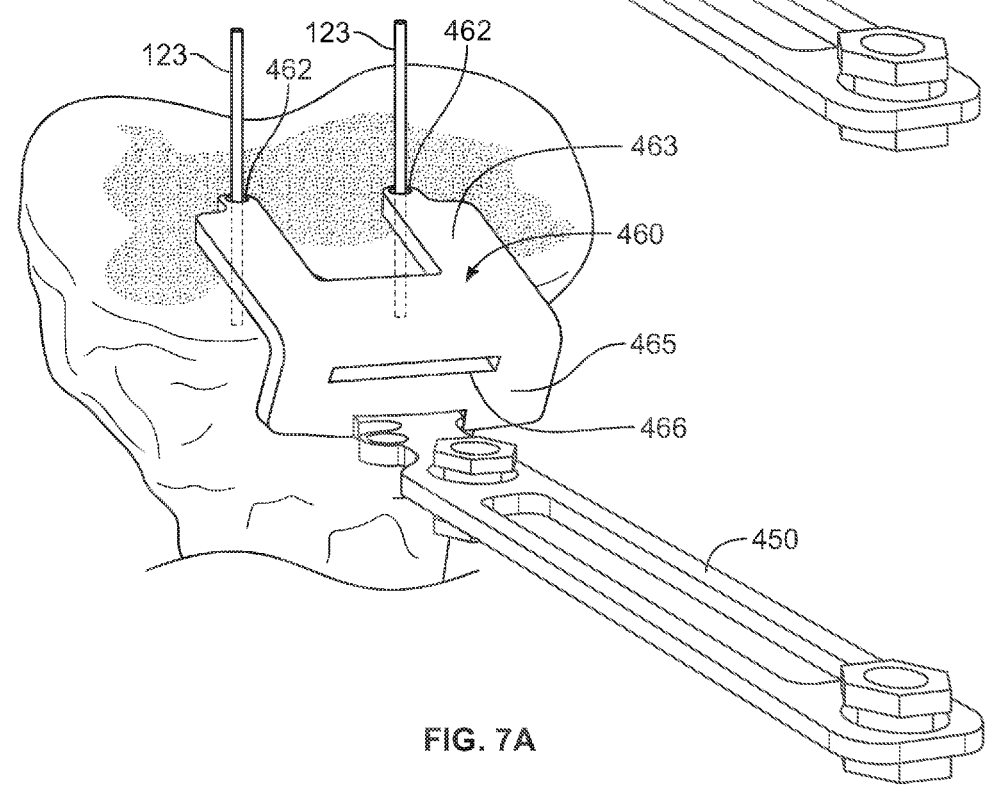
FIG. 7
FIG. 7A

PATIENT-SPECIFIC ORTHOPEDIC INSTRUMENTS

CROSS-REFERENCE TO RELATED APPLICATIONS

This application is a divisional of U.S. application Ser. No. 12/995,361 filed on Nov. 29, 2010, which is a continuation-in-part of (1.) U.S. application Ser. No. 12/938,905 filed on Nov. 3, 2010; and (2.) U.S. application Ser. No. 12/938,913 filed on Nov. 3, 2010; which is a continuation-in-part of U.S. application Ser. No. 12/893,306 filed on Sep. 29, 2010, which is a continuation-in-part of U.S. application Ser. No. 12/888,005 filed on Sep. 22, 2010, now U.S. Pat. No. 8,377,066 issued on Feb. 19, 2013, which is a continuation-in-part of U.S. application Ser. No. 12/714,023 filed on Feb. 26, 2010, now U.S. Pat. No. 8,241,293 issued on Aug. 14, 2012, which is continuation-in-part of: (1.) U.S. application Ser. No. 12/571,969 filed on Oct. 1, 2009, which is a continuation-in-part of U.S. application Ser. No. 12/486,992 filed on Jun. 18, 2009, and (2.) U.S. application Ser. No. 12/389,901 filed on Feb. 20, 2009, now U.S. Pat. No. 8,133,234 issued on Mar. 13, 2012, which is a continuation-in-part of U.S. application Ser. No. 12/211,407 filed on Sep. 16, 2008, which is a continuation-in-part of U.S. application Ser. No. 12/039,849 filed on Feb. 29, 2008, now U.S. Pat. No. 8,282,646 issued on Oct. 9, 2012, which: (1) claims the benefit of U.S. Provisional Application No. 60/953,620 filed on Aug. 2, 2007, U.S. Provisional Application No. 60/947,813 filed on Jul. 3, 2007, U.S. Provisional Application No. 60/911,297 filed on Apr. 12, 2007, and U.S. Provisional Application No. 60/892,349 filed on Mar. 1, 2007; (2) is a continuation-in-part U.S. application Ser. No. 11/756,057 filed on May 31, 2007, now U.S. Pat. No. 8,092,465 issued on Jan. 10, 2012, which claims the benefit of U.S. Provisional Application No. 60/812,694 filed on Jun. 9, 2006; (3) is a continuation-in-part of U.S. application Ser. No. 11/971,390 filed on Jan. 9, 2008, now U.S. Pat. No. 8,070,752 issued on Dec. 6, 2011, which is a continuation-in-part of U.S. application Ser. No. 11/363,548 filed on Feb. 27, 2006, now U.S. Pat. No. 7,780,672 issued on Aug. 24, 2010; and (4) is a continuation-in-part of U.S. application Ser. No. 12/025,414 filed on Feb. 4, 2008, now U.S. Pat. No. 8,298,237 issued on Oct. 30, 2012, which claims the benefit of U.S. Provisional Application No. 60/953,637 filed on Aug. 2, 2007.

This application is a continuation-in-part of U.S. application Ser. No. 12/995,361 filed on Nov. 29, 2010, which is a continuation-in-part of U.S. application Ser. No. 12/872,663 filed on Aug. 31, 2010, now U.S. Pat. No. 8,407,067 issued on Mar. 26, 2013, which claims the benefit of U.S. Provisional Application No. 61/310,752 filed on Mar. 5, 2010.

This application is a continuation-in-part of U.S. application Ser. No. 12/995,361 filed on Nov. 29, 2010, which is a continuation-in-part of U.S. application Ser. No. 12/483,807 filed on Jun. 12, 2009, now U.S. Pat. No. 8,473,305 issued on Jun. 25, 2013, which is a continuation-in-part of U.S. application Ser. No. 12/371,096 filed on Feb. 13, 2009, which is a continuation-in-part of U.S. application Ser. No. 12/103,824 filed on Apr. 16, 2008, now abandoned, which claims the benefit of U.S. Provisional Application No. 60/912,178 filed on Apr. 17, 2007.

This application is a continuation-in-part of U.S. application Ser. No. 12/995,361 filed on Nov. 29, 2010, which is a continuation-in-part of U.S. application Ser. No. 12/103,834 filed on Apr. 16, 2008, now U.S. Pat. No. 7,967,868 issued on Jun. 28, 2011, which claims the benefit of U.S. Provisional Application No. 60/912,178 filed on Apr. 17, 2007.

The disclosures of the above applications are incorporated herein by reference.

INTRODUCTION

The present teachings provide various patient-specific alignment and resection guides and associated instruments for knee arthroplasty.

SUMMARY

The present teachings provide an orthopedic device that includes a patient-specific alignment guide operable for preparing a bone of a patient for resection during joint arthroplasty. The alignment guide includes a patient-specific bone engagement surface complementary to a surface of the bone of the patient and imaged from a bone scan of the patient. The alignment guide includes a plurality of guiding bores and a plurality of alignment pins received through corresponding guiding bores r attaching the alignment guide to the bone. The alignment pins are resorbable and can be sawn or cut off during a resection of the bone.

The present teachings also provide an orthopedic device that includes a patient-specific tibial alignment guide operable for preparing a tibia of a patient for resection during joint arthroplasty. The tibial alignment guide includes a first portion engageable with a proximal surface of the tibia and a second portion engageable with an anterior surface of the tibia. The first portion defines first and second proximal guiding bores and an opening between the first and second proximal guiding bores. The second portion defines first and second anterior guiding bores and an elongated slot for guiding a blade for resecting the tibia. The tibial alignment guide also includes a patient-specific bone engagement surface defined by the first and second portions and complementary to the proximal and anterior surface of the tibia. The orthopedic device further includes a plurality of alignment pins receivable through respective proximal and anterior guiding bores for attaching the alignment guide to the tibia. The alignment pins are resorbable and can be sawn or cut off during resection of the tibia.

The present teachings also provide a method of preparing a distal femur for a knee joint implant. The method includes mounting a patient-specific bone engagement surface of a femoral alignment guide on a complementary surface of a distal femur a patient. The method also includes inserting first and second resorbable anterior alignment pins into an anterior surface of the distal femur through corresponding first and second anterior guiding bores of the femoral alignment guide, and inserting first and second resorbable distal alignment pins into a distal surface of the distal femur through corresponding first and second distal guiding bores of the femoral alignment guide. The method further includes supporting a distal cutting guide on the first and second anterior alignment pins, passing a cutting blade through a cutting slot of the cutting guide, and resecting the distal femur with the cutting blade by cutting through the alignment guide and the first and second distal alignment pins to form a resected distal surface.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein:

FIG. 7 is an environmental perspective view of a patient-specific alignment/resection guide of FIG. 6 shown with a guiding tool;

FIG. 7A is an environmental perspective view a guiding tool according to the present teachings;

DESCRIPTION OF VARIOUS ASPECTS

Figure 1:
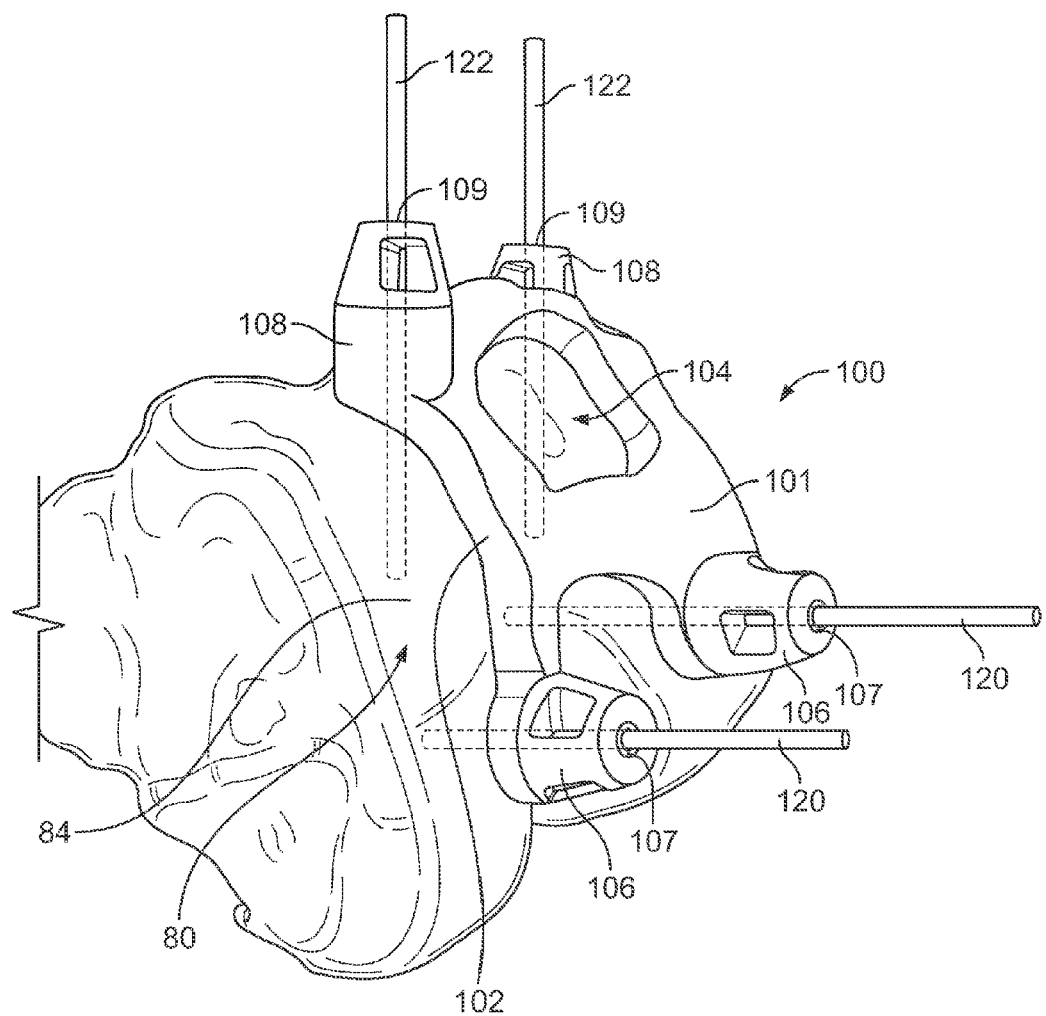
FIG. 1 is an environmental perspective view of a patient-specific alignment guide with resorbable alignment pins according to the present teachings.

The following description is merely exemplary in nature and is in no way intended to limit the present teachings, applications, or uses.

The present teachings generally provide various patient-specific alignment and resection guides and other associated instruments for use in orthopedic surgery, such as, for example, in joint replacement or revision surgery. The patient-specific guides can be used either with conventional or patient-specific implant components and can be prepared with computer-assisted image methods. Computer modeling for obtaining three-dimensional (3-D) images of the patient's anatomy using MRI or CT scans of the patient's anatomy, the patient-specific prosthesis components, and the patient-specific guides and templates can be designed using various CAD programs and/or software available, for example, by Materialise USA, Ann Arbor, Mich.

Patient-specific alignment guides and implants are generally configured to match the anatomy of a specific patient. The patient-specific alignment guides are generally formed using computer modeling based on the patient's 3-D anatomic image and have an engagement surface that is made to conformingly contact and match a three-dimensional image of the patient's bone surface (with or without cartilage or other soft tissue) in only one position, by the computer methods discussed above. The patient-specific alignment guides are designed and prepared preoperatively using anatomic landmarks, such as osteophytes, for example, and can be mounted intra-operatively without any registration or other guidance based on their unique patient-specific surface guided by the patient's anatomic landmarks.

The patient-specific alignment guides can include custom-made guiding formations, such as, for example, guiding bores or cannulated guiding posts or cannulated guiding extensions or receptacles that can be used for supporting or guiding other instruments, such as drill guides, reamers, cutters, cutting guides and cutting blocks or for inserting pins or other fasteners according to a surgeon-approved pre-operative plan for performing various resections as indicated for an arthroplasty, joint replacement, resurfacing or other procedure for the specific patient.

The patient-specific guides can also include resection or cutting formations, such as cutting slots or cutting edges or planes guiding a cutting blade to perform bone resections directly through the patient-specific cutting guide. The patient-specific guides can be used in minimally invasive surgery. Various alignment/resection guides and preoperative planning procedures are disclosed in commonly assigned and co-pending U.S. patent application Ser. No. 11/756,057, filed on May 31, 2007; U.S. patent application Ser. No. 12/211,407, filed Sep. 16, 2008; U.S. patent application Ser. No. 11/971,390, filed on Jan. 9, 2008, U.S. patent application Ser. No. 11/363,548, filed on Feb. 27, 2006; and U.S. patent application Ser. No. 12/025,414, filed Feb. 4, 2008. The disclosures of the above applications are incorporated herein by reference.

As disclosed, for example, in the above-referenced U.S. patent application Ser. No. 11/756,057, filed on May 31, 2007, in the preoperative planning stage for a joint replacement or revision procedure, an MRI scan or a series of CT scans of the relevant anatomy of the patient, such as, for example, the entire leg of the joint to be reconstructed, can be performed at a medical facility or doctor's office. The scan data obtained can be sent to a manufacturer. The scan data can be used to construct a three-dimensional image of the joint and provide an initial implant fitting and alignment in a computer file form or other computer representation. The initial implant fitting and alignment can be obtained using are alignment method, such as alignment protocols used by individual surgeons.

The outcome of the initial fitting is an initial surgical plan that can be printed or provided in electronic form with corresponding viewing software. The initial surgical plan can be surgeon-specific, when using surgeon-specific alignment protocols. The initial surgical plan, in a computer/digital five form associated with interactive software, can be sent to the surgeon, or other medical practitioner, for review. The surgeon can incrementally manipulate the position of images of various implant components in an interactive image of the joint. Additionally, the surgeon can select or modify resection planes, types of implants and orientations of implant insertion. After the surgeon modifies and/or approves the surgical plan, the surgeon can send the final, approved plan to the manufacturer.

After the surgical plan is approved by the surgeon, patient-specific alignment/resection guides can be designed using a CAD program or other imaging software, such as the software provided by Materialise, for example, according to the surgical plan. Computer instructions of tool paths for machining the patient-specific alignment guides can be generated and stored in a tool path data file. The tool path can be provided as input to a CNC mill or other automated machining system, and the alignment guides can be machined from polymer, ceramic, metal or other suitable material, and sterilized. The sterilized alignment guides can be shipped to the surgeon or medical facility, for use during the surgical procedure. Various patient-specific knee alignment guides and associated methods are disclosed in the commonly assigned U.S. application Ser. No. 11/756,057, filed on May 31, 2007 (published as 2007/0288030 on Dec. 13, 2007), which is incorporated herein by reference, and are now commercially available from Biomet Manufacturing Corp., Warsaw, Ind. in its Signature™ series.

The various patient-specific alignment guides can be made of any biocompatible material, including, polymer, ceramic, metal or combinations thereof. The patient-specific alignment guides can be disposable and can be combined or used with reusable non patient-specific cutting and guiding components.

Referring to FIG. 1 an exemplary patient-specific femoral alignment guide 100 according to the present teachings is shown mounted on the corresponding patient's distal femur 80. The femoral alignment guide 100 can have a lightweight body 101 with a patient-specific engagement surface 102 that is complementary and made to closely conform and mate with a portion of the anterior-distal surface 84 of the patient's femur 80 based on the pre-operative plan, as described above. The femoral alignment guide 100 can include a window/opening 104 and first and second distal guiding formations 106 defining guiding bores 107 for guiding corresponding distal alignment pins 120. The femoral alignment guide 100 can also include first and second anterior guiding formations 108 defining guiding bores 109 for guiding corresponding anterior alignment pins 122.

In the instruments and surgical techniques used with the patient-specific alignment guides discussed in the commonly assigned and referenced above U.S. application Ser. No. 11/756,057, filed on May 31, 2007, the distal alignment pins may be spring drill pins or other fasteners made of non-resorbable metallic biocompatible materials. Similarly, the anterior pins are metallic trochar pins or other non-resorbable fasteners. After distal and anterior holes are drilled through the bone for the corresponding distal and anterior alignment pins using the alignment guide, the alignment guide is removed. The anterior alignment pins are guided through the anterior holes and a distal cutting block is mounted on the anterior alignment pins to make a distal resection as designed in the pre-operative plan. Similarly, a four-in-one or other cutting block is mounted over the distal alignment pins to make the remaining the resections of the distal femur. Alternatively, the distal alignment pins can be removed and a cutting block having fixed or removable pins attached thereto can be mounted on the femur by placing the pins of the cutting block into separate distal holes prepared using the alignment guide or into the distal holes from which the distal pins were removed. In this manner, the distal and anterior holes and the corresponding distal and anterior alignment pins are reference elements for referencing correctly the placement of the various cutting blocks and the corresponding resections. All the alignment pins are then removed and the prosthetic components are implanted.

Figure 2:
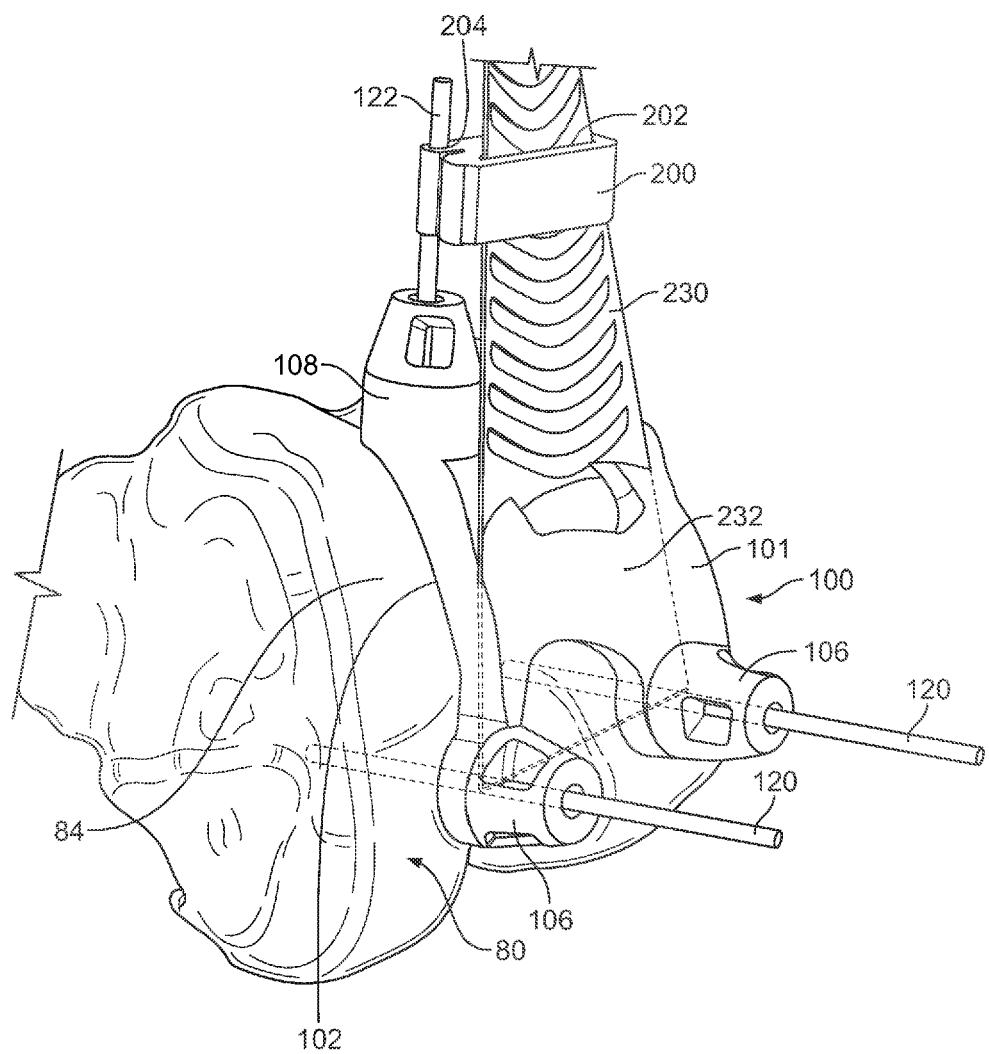
FIG. 2 is an environmental perspective view of a patient-specific alignment guide with resorbable alignment pins shown cut through during a distal resection according to the present teachings.

In contrast to the above method and according to the present teachings, the distal and anterior alignment pins are made of resorbable materials, such as polymers, and can be sawn or cut off during resection. The portions remaining in the bone can be gradually resorbed, such that the step of removing the alignment pins is eliminated. Referring to FIG. 2, for example, a distal cutting block 200 can be mounted over the anterior alignment pins 122 (only one is visible in the view of FIG. 2), which can pass through corresponding openings 204 of the distal cutting block 200, while the femoral alignment guide 100 is still nested on the distal femur 80. The alignment guide 100 is disposable and made of polymeric material that can also be sawn or cut off. The distal cutting block 200 includes a cutting slot or other cutting guiding formation 202. A cutting blade 230 is guided through the cutting slot 202 and can make the distal resection of the femur 80 sawing through the alignment guide 100 and the resorbable distal alignment pins 120 to create a resected distal surface 82 shown in FIG. 3.

Figure 3:
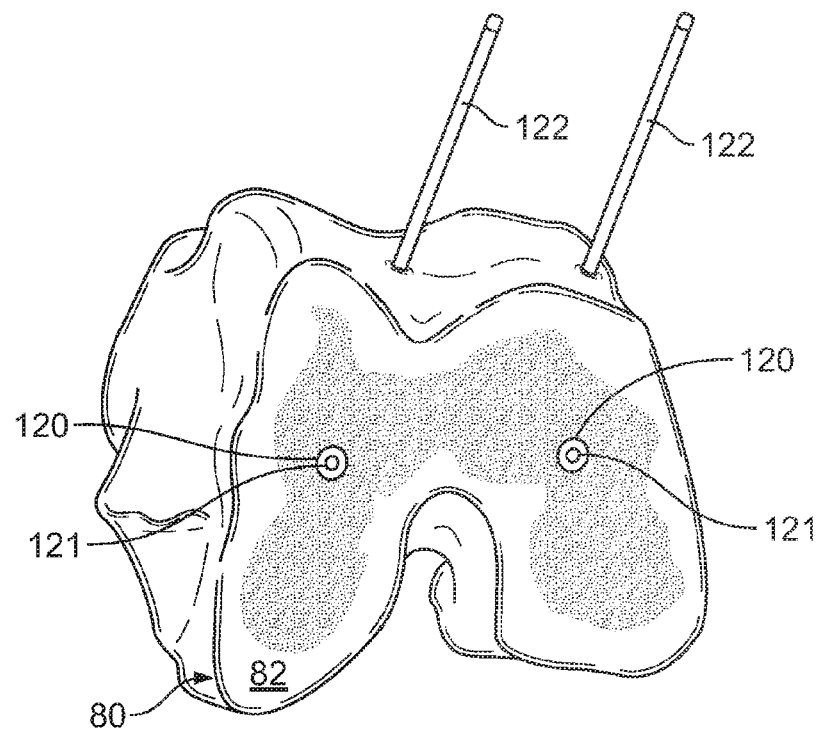
FIG. 3 is an environmental perspective view illustrating the cut-off cannulated alignment pins after a distal resection of the femur according to the present teachings.
Figure 4:
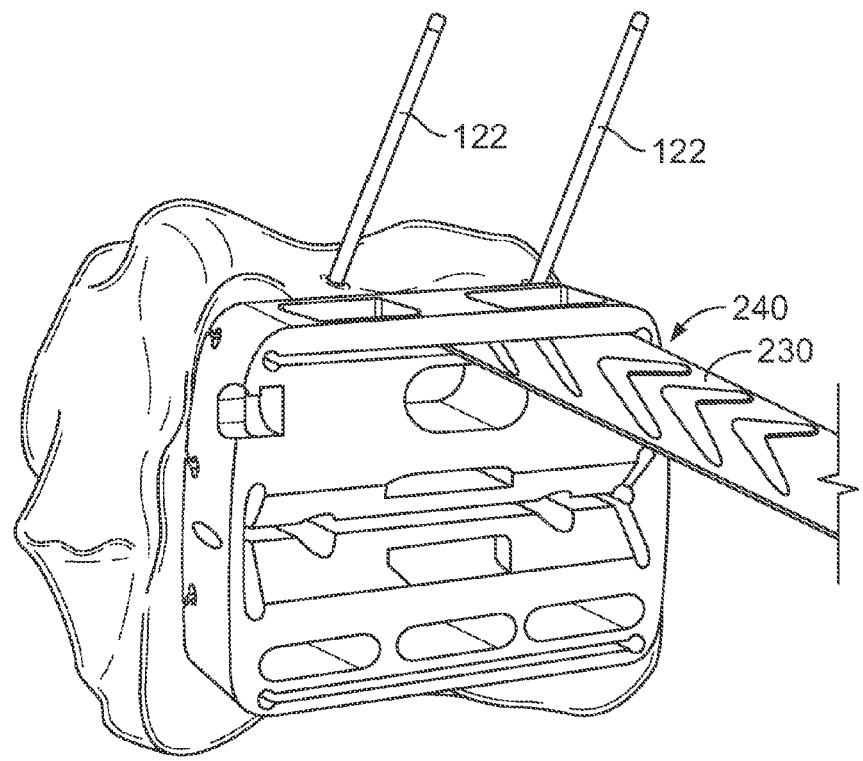
FIG. 4 is an environmental view of a cutting guide mounted on the cut-off cannulated alignment pins of FIG. 3.
Figure 4A:
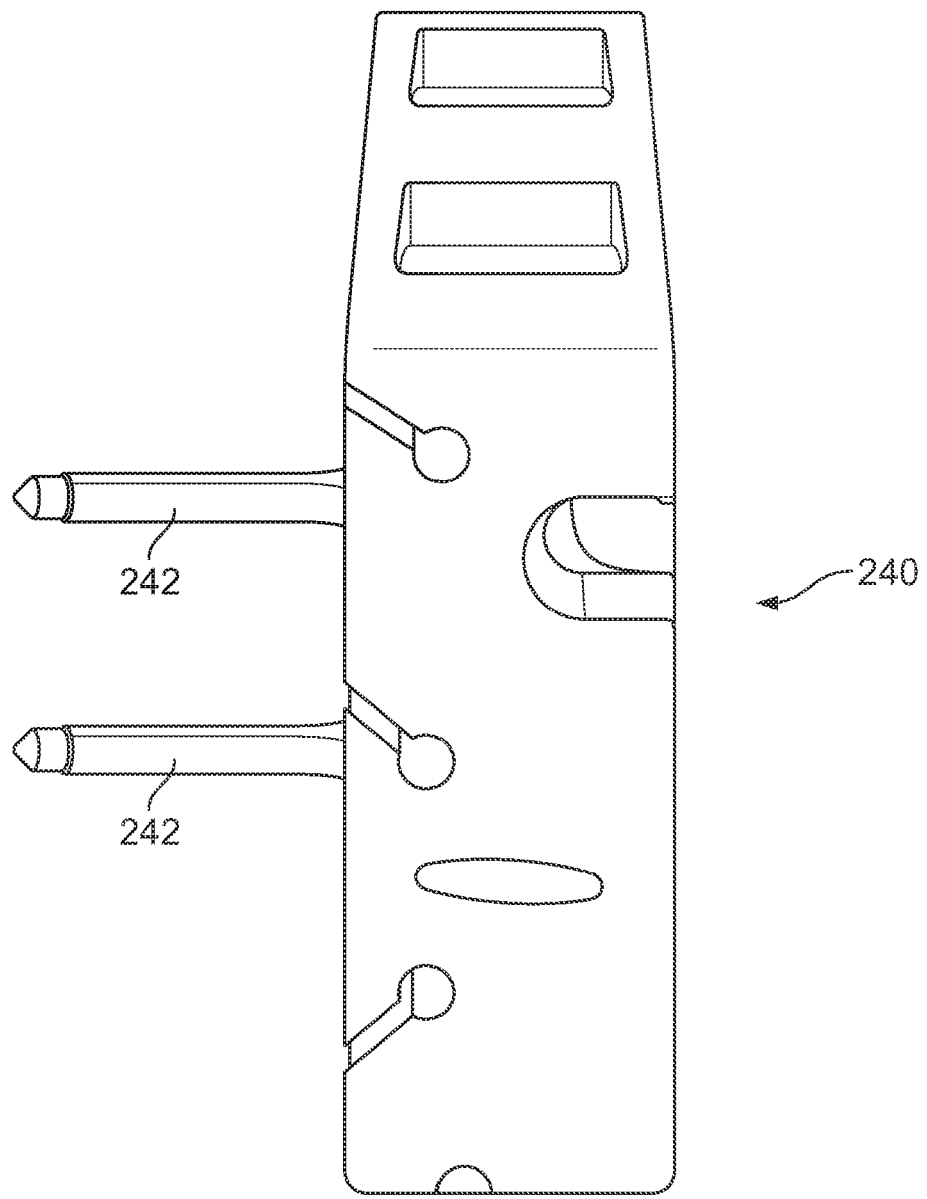
FIG. 4A is a side view of the cutting guide of FIG. 4.

The resorbable distal alignment pins 120 can be cannulated having an inner bore 121 sized for receiving corresponding pins 242 coupled to a 4-in-1 cutting block 240 for making anterior, posterior and chamfer cuts, as shown in FIGS. 3, 4 and 4A. In this respect, the bores 121 reference the location for the cutting block 240. The anterior alignment pins 122 can be also sawn-off or cut-off while making the anterior cut. Alternatively, non-resorbable cannulated distal alignment pins, which are mounted in corresponding pre-drilled holes, can be used for mounting the 4-in-1 cutting block 240 on the resected distal femur 82. In other embodiments, the pins of the 4-in-1 cutting block 240 can be cannulated and slide over non-cannulated distal alignment pins 120. It will be appreciated that when using non-resorbable alignment pins, the alignment pins that are not used to support and guide the cutting block can be removed prior to resection to avoid interference with the resection.

Figure 5:
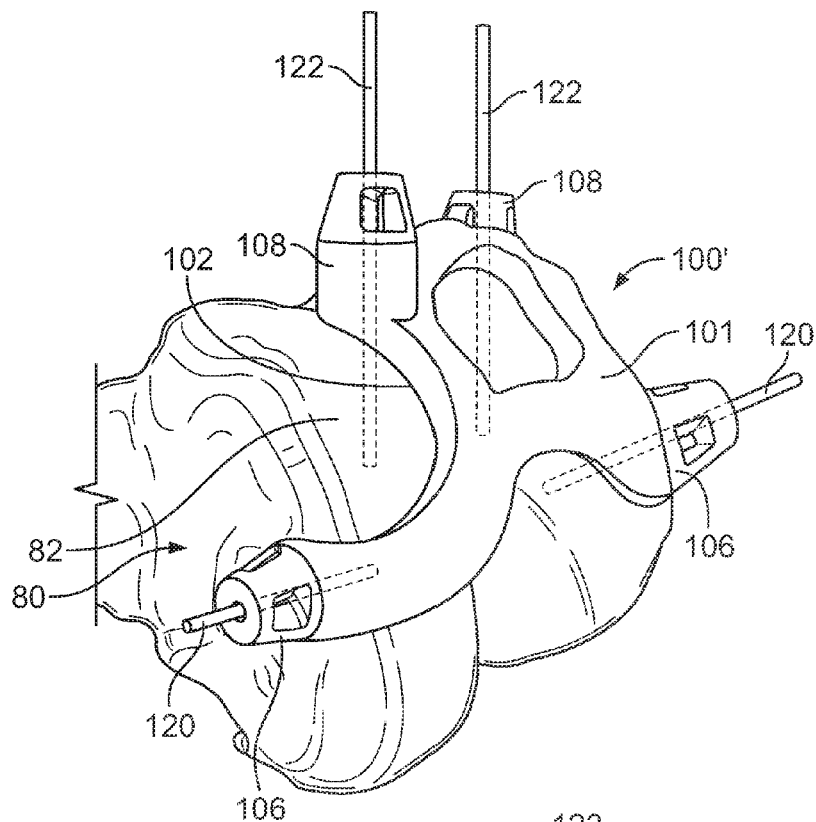
FIG. 5 is an environmental perspective view of a patient-specific alignment guide according to the present teachings.

In an alternative embodiment illustrated in FIG. 5, the first and second distal guiding formations 106 of a femoral alignment guide 100' are positioned obliquely, i.e., not perpendicularly relative to the surface of the medial and lateral condyles, such that the distal alignment pins 120 do not obstruct the distal cut and need not be cut through or removed. The femoral alignment guide 100' can remain on the distal femur 80 and can be cut through when the distal resection is made, as discussed above in connection with FIG. 2. The distal alignment pins 120 can also be made of resorbable material that can be sawn or cut off.

Figure 6:
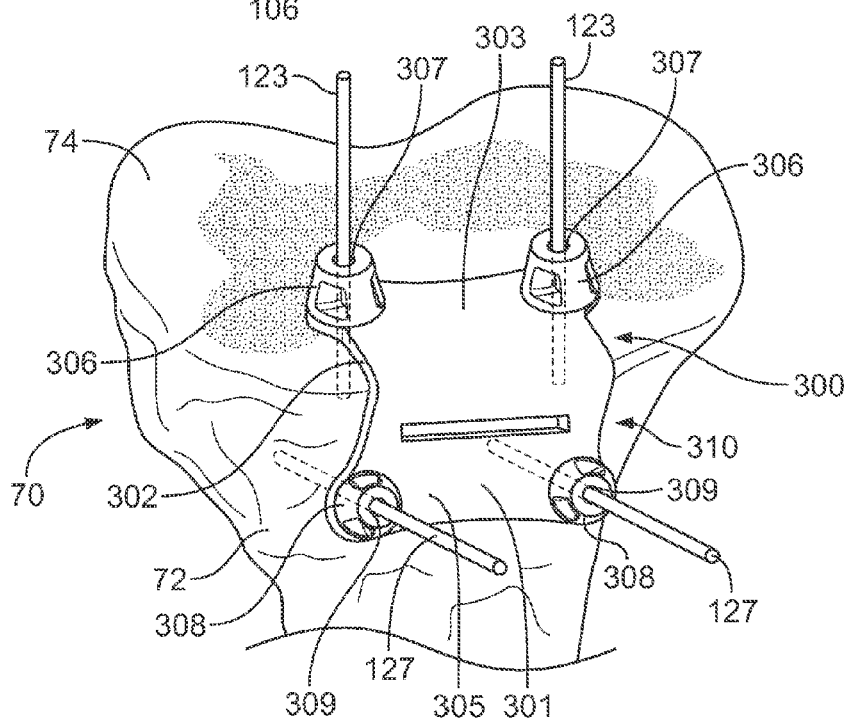
FIG. 6 is an environmental perspective view of a patient-specific alignment/resection guide according to the present teachings.

Referring to FIG. 6, a representative tibial alignment/resection guide 300 is illustrated according to the present teachings. The tibial alignment guide 300 can include a body 301 having a proximal portion 303, an anterior portion 305 and a patient-specific bone engagement surface 302 complementary and made to closely conform and mate with a portion of the anterior surface 72 and proximal surface 74 of the patient's tibia 70 in only one position based on the pre-operative plan. The tibial alignment guide 300 can include first and second proximal guiding formations 306 defining guiding bores 307 for corresponding proximal alignment pins or other fasteners 123. The tibial alignment/resection guide 300 can also include first and second anterior guiding formations 308 defining guiding bores 309 for corresponding anterior alignment pins or other fasteners 127. As discussed above in connection with alignment guides in general and the femoral alignment guide 100 in particular, the tibial alignment guide 300 can be used to drill reference holes for the corresponding proximal and anterior alignment pins 123, 127, which can then be re-inserted as needed for each resection and corresponding resection block after the tibial alignment/resection guide 300 is removed. When using resorbable alignment pins, the alignment pins can remain and be sawn or cut off during resection. In the embodiment illustrated in FIG. 6, the tibial alignment/ resection guide 300 can include a resection guiding slot 310 for guiding a tibial resection according to the pre-operative plan for the patient. The tibial alignment/resection guide 300 can be optionally used as a resection guide for resecting the tibia 70 through the guiding slot 310 with a blade or other resection tool while the tibial alignment/resection guide 300 is mounted en the tibia 70.

Referring to FIG. 7, when a tibial alignment/resection guide 300 that is disposable and lightweight is used for making a resection, a metal or other more rigid guide tool 460 can be optionally used by the surgeon for providing additional rigidity and stability for the surgeon while guiding a resection blade 230 (shown in FIG. 2). The guide tool 460 can include an anterior portion 465 having an elongated slot 466, and a proximal portion 463 having first and second apertures 462 that can fit over the proximal guiding formations 306 of the alignment guide 300 and/or the corresponding alignment pins 123, as shown in FIG. 7A. The elongated slot 466 is aligned with the resection guiding slot 310 of the tibial alignment/resection guide 300 when the first and second apertures 462 are aligned over the proximal guiding formations 306. The guide tool 460 can also include a handle 450, which can be integrally or removably coupled to the guide tool 460. Referring to FIG. 7A, the guide tool 460 can also be used over the proximal alignment pins 123, after the tibial alignment/resection guide 300 is removed. Because the proximal alignment pins 123 have been placed through the tibial alignment/resection guide 300, the proximal alignment pins 123 correctly reference the guide tool 460 and the elongated slot 466 of the guide tool 460 for guiding the tibia resection according to the pre-operative plan. A similar guide tool can be configured to be used over the anterior alignment formations 308.

Figure 8A:
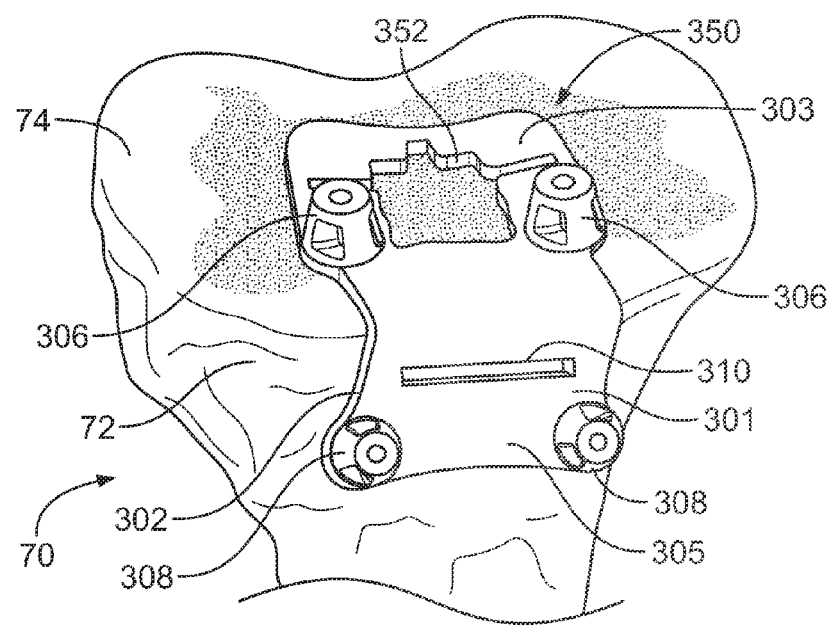
FIG. 8A is an environmental perspective view of a patient-specific tibial alignment/resection guide including a tool opening according to the present teachings.
Figure 8B:
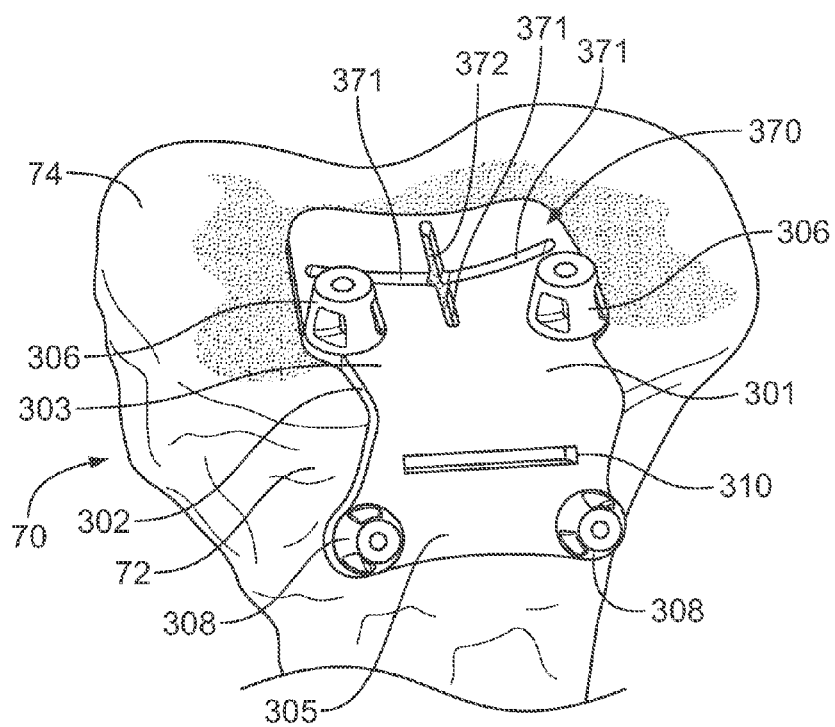
FIG. 8B is an environmental perspective view of a patient-specific alignment/resection guide including a tibial punch opening according to the present teachings.

Referring to FIGS. 8A and 8B, tibial alignment/resection guides 350, 370, similar in other respects with the tibial alignment/resection guide 300, can include corresponding proximal openings 352, 372 between the proximal alignment formations 306. The openings 352, 372 can be shaped for guiding various instruments. Referring to FIG. 8B, for example, the proximal opening 372 includes a plurality of fin-shaped slots 371 configured in the shape a punch mask for guiding a finned stem punch through the proximal surface 74 of the tibia 70 along the direction of the intramedullary canal axis in preparation for a tibial stem implant.

Figure 9A:
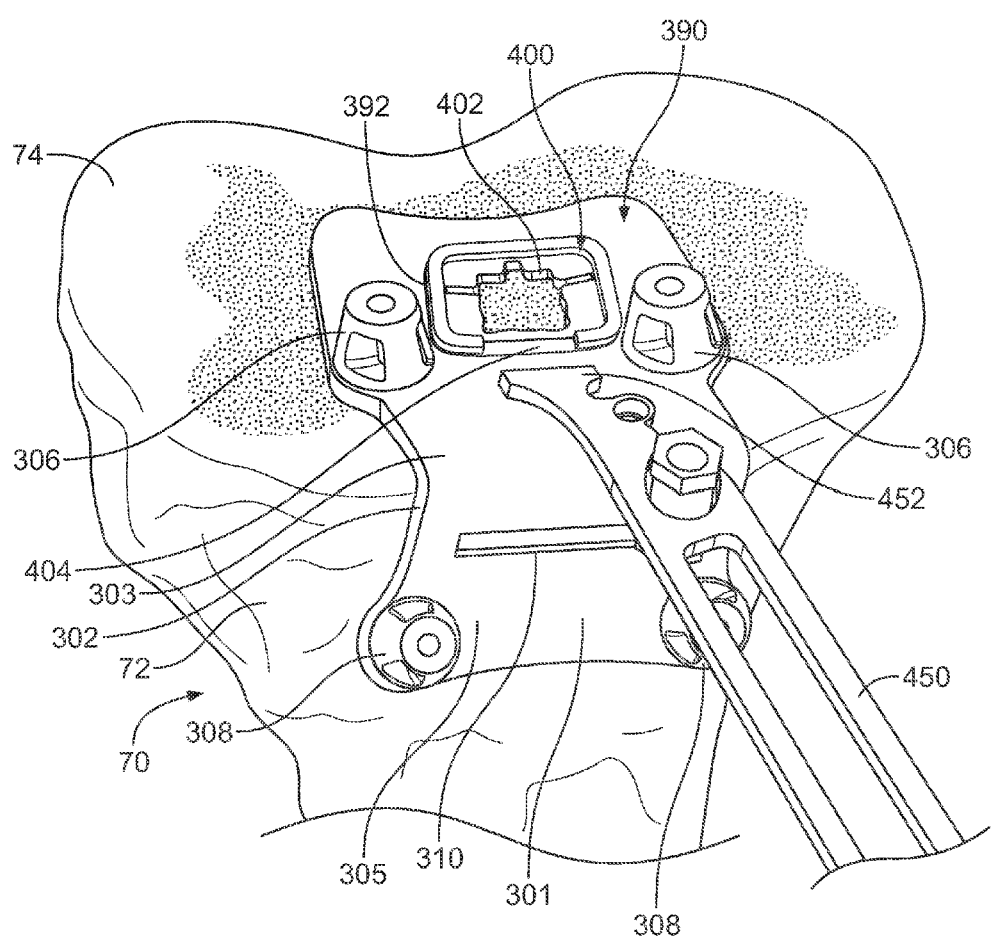
FIG. 9A is an environmental perspective view of a patient-specific tibial alignment/resection guide including an insert according to the present teachings.
Figure 9B:
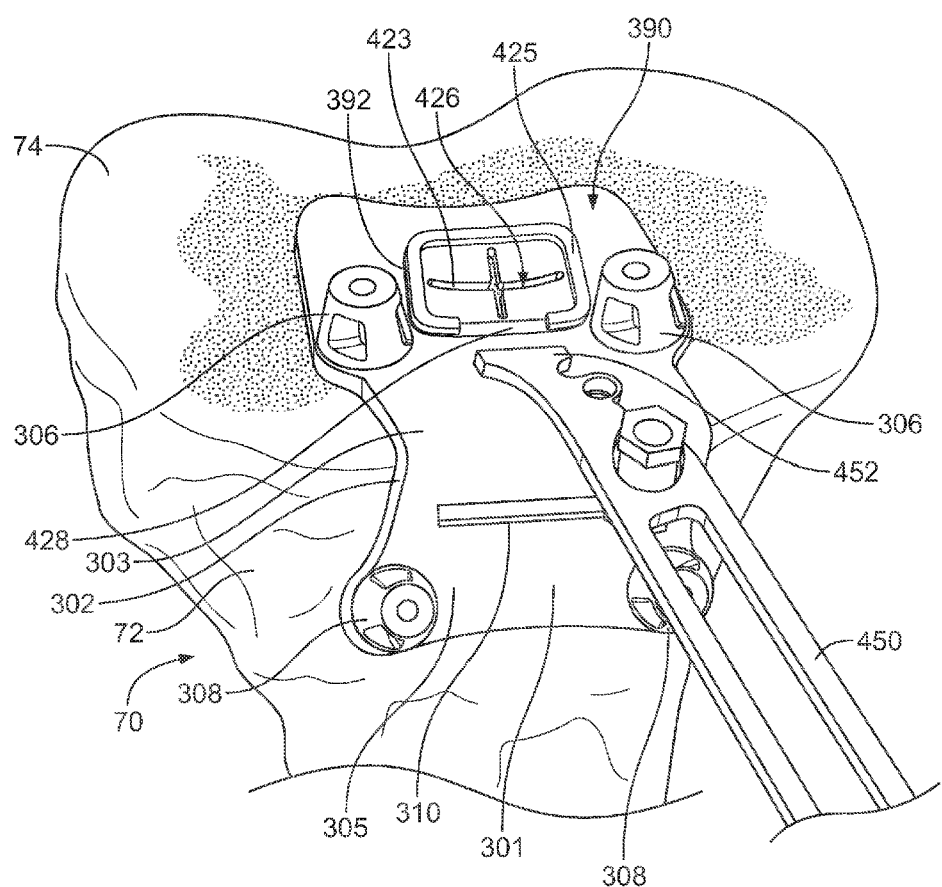
FIG. 9B is an environmental perspective view of a patient-specific alignment/resection guide including a tibial punch insert according to the present teachings.

Referring to FIGS. 9A and 9B, a tibial alignment/resection guide 390, can include an opening 392 for receiving a removable insert 400 or 425 that is made of a more rigid material, such as, for example, metal or metal alloy. The inserts 400, 425 can be simply placed in the opening or removably coupled by a snap-fit engagement or by a frictional or other mechanical coupling. The inserts 400, 425 can include a corresponding opening 402, 426 shaped for guiding an instrument. The opening 426 of the insert 425, for example, includes a plurality of fin-shaped slots 423 shaped to guide a finned stem punch along the intramedullary canal axis in preparation for a tibial stem implant. Each of the inserts 400, 425 can be used with a modular handle 450 that can be removably coupled with the corresponding insert by a tongue- and groove, dovetail or other coupling arrangement between a distal portion 452 of the handle 450 and a mating portion 404 or 428 of the corresponding insert 400, 425 (details not shown). A plurality of inserts can be provided for selective use by the surgeon in terms of preference or in combination with various punches and corresponding tibial stems.

The various alignment/resection guides described above (100, 100', 300, 350, 370, 390) can be made of biocompatible polymeric or other plastic materials and are disposable. The alignment/resection guides can be cut through while making various resection cuts. The various alignment pins can be metallic or resorbable. Resorbable pins can be cut off or sawn off or broken off by hand with portions remaining in the bone and resorbed over time. The various alignment/resection guides can also be frangible along score lines or either intentionally weakened portions of the alignment/resection guides. Alternatively, the alignment/resection guides can have modularly coupled portions that can be optionally removed, for example, before performing a resection. Additional details for alignment/resection guides with frangible and/or modularly coupled portions are disclosed in commonly assigned and co-pending patent application Ser. No. 12/571,969, filed Oct. 1, 2009 and published as 2010-0087829 on Apr. 8, 2010, the disclosures of which are incorporated herein by reference.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the present teachings without departing from the essential scope thereof. One skilled in the art will readily recognize from such discussion, and from the accompanying drawings and claims, that various changes, modifications and variations can be made therein without departing from the spirit and scope of the present teachings as defined in the following claims.

What is claimed is:

1. An orthopedic system comprising:
a patient-specific alignment guide operable for preparing a bone of a patient during joint arthroplasty, the alignment guide including a patient-specific bone engagement surface configured to be complementary to a surface of the bone of the patient, the alignment guide including a plurality of guiding bores;
a plurality of alignment members receivable through corresponding guiding bores for attaching the alignment guide to the bone;
a cutting block; and
one or more pins, wherein a one of the plurality of alignment members or the one or more pins are cannulated and configured to receive the other of the plurality of alignment members or the one or more pins to mount the cutting block into a desired position relative to the bone.

2. The system of claim 1, wherein the alignment members are configured to be cut off during a first resection of the bone.

3. The system of claim 2, wherein the first resection is to a distal portion of the bone.

4. The system of claim 3, wherein the cutting block is configured to facilitate a second resection of the bone.

5. The system of claim 4, wherein the second resection is to an anterior portion of the bone.

6. The system of claim 4, wherein the alignment members are configured to be cut off during the second resection of the bone.

7. The system of claim 4, wherein the alignment members are configured to be further cut off during both the first resection of the bone and the second resection of the bone.

8. The system of claim 2, wherein the cutting block patient-specific alignment guide is configured with a slot configured to facilitate the first resection.

9. The system of claim 2, wherein the alignment members are configured to be cut off during the first resection of the bone.

10. The system of claim 2, wherein the first resection cuts through the patient-specific alignment guide.

11. The system of claim 1, wherein the alignment members are resorbable.

12. The system of claim 1, wherein the patient-specific alignment guide comprises a tibial alignment guide and the bone comprises a tibia, the tibial alignment guide including:
a first portion engageable with a proximal surface of the tibia, the first portion defining a first and a second of the corresponding guiding bores and an opening between the first and the second of the corresponding guiding bores; and
a second portion engageable with an anterior surface of the tibia, the second portion defining a third and a fourth of the corresponding guiding bores.

13. The system of claim 1, wherein the plurality of guiding bores includes a pair of oblique guiding bores oriented at an oblique angle relative to a surface of the distal femur.

14. The system of claim 1, wherein the patient-specific alignment guide comprises a femoral alignment guide and the bone comprises a femur, the femoral alignment guide including:
a first portion engageable with a distal surface of a femur, the first portion defining a first and a second of the corresponding guiding bores; and
a second portion engageable with an anterior surface of the tibia, the second portion defining a third and a fourth of the corresponding guiding bores.

15. The system of claim 14, wherein the femoral alignment guide is configured to be cut through during a resection of the femur.

16. The system of claim 14, wherein the cutting block comprises at least one of a distal cutting block mountable to at least a first of the plurality of alignment members and a 4-in-1 cut guide mountable to at least a second of the plurality of alignment members.

17. The system of claim 1, wherein the patient-specific alignment guide is configured to be cut through during a resection of the bone.

18. An orthopedic system comprising: a patient-specific alignment guide operable for preparing a bone of a patient during joint arthroplasty, the alignment guide including a patient-specific bone engagement surface configured to be complementary to a surface of the bone of the patient, the alignment guide including a plurality of guiding bores; a plurality of alignment members receivable through corresponding guiding bores for attaching the alignment guide to the bone; a cutting block mountable to one or more of the plurality of alignment members and configured to guide a first resection of the bone by cutting through the alignment guide; and one or more pins, wherein a one of the plurality of alignment members or the one or more pins are cannulated and configured to receive the other of the plurality of alignment members or the one or more pins to mount the cutting block into a desired position relative to the bone.

19. The system of claim 18, the cutting block comprises at least one of a distal cutting block mountable to at least a first of the plurality of alignment members and a 4-in-1 cut guide mountable to at least a second of the plurality of alignment members.

* * * * *